(12) United States Patent
Renninger et al.

(10) Patent No.: US 7,935,156 B2
(45) Date of Patent: May 3, 2011

(54) JET FUEL COMPOSITIONS AND METHODS OF MAKING AND USING SAME

(75) Inventors: Neil Stephen Renninger, Oakland, CA (US); Jason A. Ryder, Oakland, CA (US); Karl J. Fisher, Petaluma, CA (US)

(73) Assignee: Amyris Biotechnologies, Inc., Emeryville, CA (US)

( * ) Notice: Subject to any disclaimer, the term of this patent is extended or adjusted under 35 U.S.C. 154(b) by 820 days.

(21) Appl. No.: 11/986,485

(22) Filed: Nov. 20, 2007

(65) Prior Publication Data

US 2010/0281846 A1    Nov. 11, 2010

Related U.S. Application Data

(60) Provisional application No. 60/860,853, filed on Nov. 21, 2006, provisional application No. 60/951,236, filed on Jul. 23, 2007.

(51) Int. Cl.
*C10L 1/10* (2006.01)

(52) U.S. Cl. .................................. 44/300; 585/1; 585/14

(58) Field of Classification Search ..................... 44/300; 585/1, 14

See application file for complete search history.

(56) References Cited

U.S. PATENT DOCUMENTS

| | | | |
|---|---|---|---|
| 1,903,255 A * | 3/1933 | Busch .............................. | 585/14 |
| 2,712,479 A | 7/1955 | Fox et al. | |
| 3,441,497 A | 4/1969 | Walter et al. | |
| 4,242,100 A | 12/1980 | Parker et al. | |
| 4,818,250 A | 4/1989 | Whitworth | |
| 4,915,707 A | 4/1990 | Whitworth | |
| 5,186,722 A | 2/1993 | Cantrell et al. | |
| 5,501,713 A | 3/1996 | Wilkins, Jr. | |
| 5,559,085 A | 9/1996 | Duncan, Jr. | |
| 2002/0005010 A1 | 1/2002 | Rosenbaum | |
| 2004/0063143 A1 | 4/2004 | Cheng et al. | |

FOREIGN PATENT DOCUMENTS

WO    WO 2007/005944 A2    1/2007

OTHER PUBLICATIONS

PCT ISA/US International Search Report, dated Nov. 4, 2008, for International Application No. PCT/US2007/24270, filed Nov. 20, 2007.
U.S. Appl. No. 11/986,484, filed Nov. 20, 2007, Renninger et al.
Imada et al., "Flavin-Catalyzed Generation of Diimide: An Environmentally Friendly Method for the Aerobic Hydrogenation of Olefins," J. Am. Chem. Soc., 127:14544-14545 (2005).
Soltes et al., "Hydroprocessing of Biomass Tars for Liquid Engine Fuels," Progress in Biomass Conversion, 5:1-68 (1984).
Van Camp et al., "Thermal Cracking of Kerosine," Industrial & Engineering Chemistry Process Design and Development, 23(1):155-162 (1984).
May 26, 2010, International Preliminary Report on Patentability.

\* cited by examiner

*Primary Examiner* — Cephia D Toomer
(74) *Attorney, Agent, or Firm* — Jones Day

(57) ABSTRACT

Provided herein are, among other things, jet fuel compositions and methods of making and using the same. In some embodiments, the fuel compositions comprise at least a fuel component readily and efficiently produced, at least in part, from a microorganism. In certain embodiments, the fuel compositions provided herein comprise a high concentration of at least a bioengineered fuel component. In further embodiments, the fuel compositions provided herein comprise limonane.

26 Claims, 10 Drawing Sheets

| Property | Units | | Jet A | ASTM Test Method | Jet A (Base Fuel) | AMJ-300 (vol.% in Jet A) | | | AMJ-310 (vol.% in Jet A) | | |
|---|---|---|---|---|---|---|---|---|---|---|---|
| | | | | | | 20 | 50 | 100 | 20 | 50 | 100 |
| COMPOSITION | | | | | | | | | | | |
| Appearance | | | C & B | D4176-2 | C & B | C & B | C & B | C & B | C & B | C & B | C & B |
| Acidity | total mg KOH/g | max. | 0.10 | D3242 | 0.005 | 0.005 | 0.008 | 0.009 | 0.008 | 0.013 | 0.027 |
| Aromatics | vol.% | max. | 25 | D1319 | 16.9 | 14.8 | 7.0 | 1.4 | 16.5 | 17.9 | 15.6 |
| Sulfur | total mass % | max. | 0.30 | D4294 | 0.0685 | 0.0561 | 0.0344 | <0.0150 | 0.0542 | 0.0357 | <0.0150 |
| Sulfur, mercaptan | mass % | max. | 0.003 | D3227 | 0.0019 | 0.0014 | 0.0009 | <0.0001 | 0.0014 | 0.0009 | <0.0001 |
| VOLATILITY | | | | | | | | | | | |
| 1. Physical Distillation | | | | | | | | | | | |
| Distillation temperature | | | | | | | | | | | |
| Initial boiling point, temperature | °C | | | D86 | 153 | 157 | 161 | 154 | 161 | 163 | 168 |
| 10% recovered, temperature | °C | max. | 205 | D86 | 176 | 172 | 169 | 168 | 173 | 170 | 168 |
| 50% recovered, temperature | °C | report | | D86 | 209 | 197 | 181 | 168 | 197 | 181 | 168 |
| 90% recovered, temperature | °C | report | | D86 | 252 | 246 | 237 | 168 | 247 | 237 | 169 |
| Final boiling point, temperature | °C | max. | 300 | D86 | 284 | 281 | 273 | 193 | 282 | 272 | 201 |
| Distillation recovery | vol.% | | | D86 | 97.6 | 98.5 | 98.6 | 98.5 | 97.0 | 98.3 | 98.9 |
| Distillation residue | vol.% | max. | 1.5 | D86 | 1.4 | 1.2 | 1.1 | 1.0 | 1.3 | 1.2 | 0.7 |
| Distillation loss | vol.% | max. | 1.5 | D86 | 1.0 | 0.3 | 0.3 | 0.5 | 0.6 | 0.5 | 0.4 |
| Flash Point | °C | min. | 38 | D86 | 43 | 43 | 43 | 43 | 43 | 43 | 43 |
| Density at 15°C | kg/m³ | range | 775 – 840 | D4052 | 811.0 | 809.1 | 806.4 | 800.9 | 810.3 | 810.5 | 809.6 |
| FLUIDITY | | | | | | | | | | | |
| Freezing point | °C | max. | -40 | D2386 | -47 | -50.5 | -57 | <-70 | -50.5 | -57 | <-70 |
| Viscosity at -20°C | mm²/s | max. | 8.0 | D445 | 5.162 | 4.166 | 3.690 | 2.849 | 4.0242 | 3.326 | 2.592 |
| COMBUSTION | | | | | | | | | | | |
| Net heat of combustion | MJ/kg | min. | 42.8 | D3338 | 43.4192 | 43.1687 | 43.3383 | 43.4125 | 43.0242 | 43.1342 | 43.8123 |
| Smoke Point | mm | min. | 18 | D1322 | 21 | 21 | 26 | 30 | 22 | 21 | 21 |
| Naphthalenes, vol. | vol.% | max. | 3 | D1840 | 2.46 | 1.94 | 1.24 | <0.01 | 2.09 | 1.42 | <0.01 |
| CORROSION | | | | | | | | | | | |
| Copper strip, 2 h at 100°C | | | No. 1 | D130 | 1A | 1B | 1A | 1A | 1B | 1B | 1B |
| THERMAL STABILITY | | | | | | | | | | | |
| JFTOT | | | | | | | | | | | |
| Temperature | °C | | | D3241 | 260 | 260 | 260 | 260 | 260 | 260 | 260 |
| Tube deposits less than | | | <3 | D3241 | <1 | <1 | <1 | <1 | <1 | <1 | <1 |
| Filter pressure drop/test time (150 min) | mm Hg/min | max. | 25 | D3241 | <1 | <1 | <1 | <1 | <1 | <1 | <1 |
| Spent fuel | mL | | No Peacock or Abnormal Color Deposits | | 495 | 445 | 475 | 480 | 460 | 440 | 440 |
| CONTAMINANTS | | | | | | | | | | | |
| Existent gum | mg/100mL | max. | 7 | D381 | 1 | <1 | 2 | 4 | 1 | 2 | 2 |
| Water reaction: | | | | | | | | | | | |
| Interface rating (Interface/Separation) | | | 1b | D1094 | 1b/2 | 1b/3 | 1b/2 | 1b/3 | 1b/2 | 1b/2 | 1b/2 |
| Change in volume | mL | max. | | D1094 | 0 | 0 | 0 | 0 | 0 | 0 | 0 |
| Microseparometer (MSEP-A) | | | | | | | | | | | |
| Without electrical conductivity additive | Rating | min. | 85 | D3948 | 99 | 99 | 99 | 99 | 98 | 98 | 99 |
| With electrical conductivity additive | Rating | min. | 70 | | | | | | | | |
| ADDITIVES | | | | | | | | | | | |
| Electrical conductivity | pS/m | | | D2624 | 4 | 2 | 5 | 8 | 3 | 2 | 2 |

FIG. 8

US 7,935,156 B2

SEQUENCE LISTING

```
<160> NUMBER OF SEQ ID NOS: 92

<210> SEQ ID NO 1
<211> LENGTH: 4247
<212> TYPE: DNA
<213> ORGANISM: Artificial Sequence
<220> FEATURE:
<223> OTHER INFORMATION: MevT66 operon

<400> SEQUENCE: 1
gaattcaaag gaggaaaata aaatgaagaa ctgtgtgatt gtttctgcgg tccgcacggc      60
gatcggcagc tttaacggct ctttagcgag cacctctgca atcgatctgg gtgcgacggt     120
cattaaggcc gccattgaac gcgccaaaat cgacagccag cacgttgatg aggtgatcat     180
gggcaatgtg ttacaagccg gcctgggtca aacccagcg cgtcaagcac tgttaaaatc     240
tggtctggcc gagaccgtgt gtggcttcac cgtcaataag gtttgcggct ctggcctgaa     300
gagcgtggcc ctggcagcac aagcgattca agccggtcag gcacaaagca tcgttgcggg     360
tggcatggag aacatgtctc tggcgccgta cttattagat gccaaagccc gcagcggtta     420
tcgcctgggc gatggtcagg tgtacgacgt catcttacgc gatggcttaa tgtgcgcgac     480
```

```
ccacggttac cacatgggta ttacggccga aaacgtggcg aaagaatacg gcattacgcg    540
cgagatgcag gatgaattag cactgcactc tcagcgcaaa gcagcagccg cgatcgagtc    600
tggtgcgttt acggcggaaa tcgtgccagt taacgtggtc acgcgcaaga gacgttcgt    660 tttcagccag gacgagttcc cgaaggcaaa cagcaccgcg gaggcttag gtgccttacg    720 cccagccttt gacaaagcgg gcacggtcac cgccggtaat gcgagcggca tcaatgatgg    780
tgcagcggca ctggtcatca tggaagagag cgccgcatta gcagcgggtc tgaccccatt    840
agcgcgcatt aaatcttatg ccagcggcgg cgtcccacca gccctgatgg gcatgggtcc    900
ggtcccagcc acgcaaaaag ccctgcaatt agcgggcctg caactggccg acattgatct    960
gatcgaggcg aacgaggcgt ttgcagcgca gttcctggcg gtgggtaaga atctgggctt   1020
cgacagcgag aaagtcaatg tgaacggtgg cgcgattgcg ttaggccatc cgattggtgc   1080
aagcggcgca cgcatcttag tgacgttact gcacgccatg caggcacgcg acaagacctt   1140
aggcctggcg accttatgta ttggtggcgg tcaaggtatc gccatggtga tcgaacgcct   1200
gaactgaaga tctaggagga aagcaaaatg aaactgagca ccaagctgtg ctggtgtggc   1260
atcaagggtc gcctgcgccc acaaaagcag caacagctgc acaacacgaa cctgcaaatg   1320
accgagctga aaagcagaa gacggccgag caaaagaccc gcccgcagaa cgttggcatc   1380
aagggcatcc agatttatat cccgacgcag tgtgtcaacc aatctgagct ggagaaattc   1440
gatggcgtca gccagggtaa gtacaccatc ggcctgggcc agaccaacat gagcttcgtg   1500
aacgaccgtg aggacatcta ttctatgagc ctgacggtgc tgtctaagct gatcaagagc   1560
tacaacatcg acacgaataa gatcggtcgt ctggaggtgg gtacggagac gctgattgac   1620
aagagcaaaa gcgtgaagtc tgtcttaatg cagctgttcg gcgagaacac ggatgtcgag   1680
ggtatcgaca ccctgaacgc gtgttacggc ggcaccaacg cactgttcaa tagcctgaac   1740
tggattgaga gcaacgcctg ggatggccgc gatgcgatcg tcgtgtgcgg cgatatcgcc   1800
atctatgaca agggtgcggc acgtccgacc ggcggtgcag gcaccgttgc gatgtggatt   1860
ggcccggacg caccaattgt cttcgattct gtccgcgcgt cttacatgga gcacgcctac   1920
gacttttaca gccggacttc cacgagcgaa tacccgtacg tggacggcca cttctctctg   1980
acctgctatg tgaaggcgct ggaccaggtt tataagtctt atagcaaaaa ggcgatttct   2040
aagggcctgg tcagcgaccc ggcaggcagc gacgccctga acgtgctgaa gtatttcgac   2100
tacaacgtgt tccatgtccc gacctgcaaa ttagtgacca aatcttatgg ccgcctgtta   2160
tataatgatt tccgtgccaa cccgcagctg ttcccggagg ttgacgccga gctggcgacg   2220
cgtgattacg acgagagcct gaccgacaag aacatcgaga agaccttcgt caacgtcgcg   2280
aagccgttcc acaaagagcg tgtggcccaa agcctgatcg tcccgaccaa cacgggcaac   2340
atgtataccg cgtctgtcta cgcggcattc gcgagcctgc tgaattacgt cggttctgac   2400
gacctgcagg gcaagcgcgt tggcctgttc agctacggta gcggcttagc ggccagcctg   2460
tatagctgca aaattgtcgg cgacgtccag cacatcatca aggagctgga catcaccaac   2520
aagctggcga gcgcatcac cgagacgccg aaagattacg aggcagcgat cgagttacgc   2580
gagaatgcgc atctgaagaa gaacttcaag ccgcaaggta gcatcgagca cctgcagagc   2640
ggcgtctact acctgacgaa cattgacgac aagttccgcc gttcttatga cgtcaaaaag   2700
taactagtag gaggaaaaca tcatggtgct gacgaacaaa accgtcatta gcggcagcaa   2760
ggtgaagtct ctgagcagcg cccaaagctc tagcagcggc ccgtctagca gcagcgagga   2820
ggacgacagc cgtgacattg agtctctgga caagaagatc cgcccgctgg aggagttaga   2880
```

-continued

```
ggccctgctg agcagcggca acaccaagca gctgaagaac aaggaagttg cagcgctggt    2940
gatccacggt aagctgccac tgtatgcgct ggaaaagaaa ctgggcgata cgacgcgtgc    3000
ggtcgcggtg cgtcgcaaag ccttaagcat cttagcggag ccccggtgt tagccagcga     3060 ccgcctgccg tacaagaact acgactacga ccgcgtgttt ggcgcgtgct gcgagaatgt    3120
cattggctac atgccgttac cggttggtgt gatcggcccg ctggtcattg atggcacgag    3180
ctatcacatt ccaatggcga ccacggaagg ttgcttagtc gccagcgcca tgcgtggctg    3240
taaggcgatt aacgccggcg gtggcgcgac gaccgtgtta accaaggatg gtatgacgcg    3300
cggtccggtc gtccgcttcc caacgctgaa gcgcagcggc gcgtgtaaga tttggctgga    3360
ttctgaggag ggccaaaacg cgatcaagaa agccttcaac tctacgagcc gtttcgcgcg    3420
tttacagcat atccagacct gcctggccgg cgacctgctg ttcatgcgct ccgcaccac     3480 cacgggcgat gcgatgggca tgaacatgat cagcaagggc gtcgaatata gcctgaaaca    3540
aatggtggaa gaatatggct gggaggacat ggaggttgtc tctgtgagcg gcaactattg    3600
caccgacaag aagccggcag ccattaactg gattgagggt cgcggcaaaa gcgtcgtggc    3660
agaagcgacc atcccaggcg acgtggtccg taaggttctg aagagcgacg tcagcgccct    3720
ggttgagtta aatatcgcga aaaacctggt cggcagcgcg atggcgggca gcgtgggtgg    3780 cttaacgca catgcagcga atctggttac ggcggttttc ttagccttag gtcaggaccc     3840
agcccaaaat gtcgagagca gcaactgcat taccttaatg aaagaggttg acggtgacct    3900
gcgcatcagc gtttctatgc cgtctatcga ggtcggcacg atcggcggcg caccgtttt    3960 agaaccgcaa ggtgcgatgc tggatctgct gggcgtgcgc ggcccacatg caacggcccc    4020
aggcaccaat gcccgccaac tggcccgtat cgtggcctgc gcggttctgg cgggtgagct    4080
gagcctgtgc gccgcattag ccgcgggcca tttagttcaa tctcacatga cccacaaccg    4140
caagccggca gaaccaacca agccaaataa cctggacgca accgacatta accgtctgaa    4200
ggatggcagc gtcacgtgca ttaaaagctg agcatgctac taagctt              4247
```

<210> SEQ ID NO 2
<211> LENGTH: 1117
<212> TYPE: DNA
<213> ORGANISM: Artificial Sequence
<220> FEATURE:
<223> OTHER INFORMATION: geranyl diphosphate synthase of Arabidopsis thaliana, codon-optimized for expression in Escherichia coli and with flanking NotI and SacI restriction sites

<400> SEQUENCE: 2

```
gcggccgcgg aaaaggaggc cggccggcat gctgctgtct aataaactgc gtgaaatggt     60
tctggctgaa gtacctaaac tggcctccgc agcagaatat tcttcaagc gtggcgttca    120 gggcaaacag ttccgtagca ccatcctgct gctgatggct accgccctgg acgtgcgtgt    180
cccggaagcc ctgatcggcg aatccaccga catcgtgacc tctgaactgc gtgttcgtca    240
gcgtggtatc gcggaaatca ccgaaatgat ccacgttgcg tctctgctgc acgacgatgt    300
gctggacgat gcagacaccc gtcgtggtgt tggttccctg aacgtggtga tgggtaacaa    360
aatgagcgtg ctggcaggcg actttctgct gtctcgcgcc tgtggtgctc tggctgcgct    420
gaagaacacc gaggtagtgg cactgctggc gactgccgta gagcacctgg ttaccggcga    480
aacgatggaa attacttctt ccaccgaaca gcgttactcc atggactact acatgcagaa    540
gacttactat aaaaccgcgt ccctgattag caactcttgt aaagcagtag cagtactgac    600
tggccaaact gcagaagtag cggtgctggc tttcgagtac ggtcgtaacc tgggtctggc    660
```

```
tttccagctg atcgatgaca tcctggactt tactggtacc agcgcaagcc tgggtaaagg    720
ttccctgtct gacattcgtc acggcgttat caccgctccg attctgttcg cgatggaaga    780
attcccgcag ctgcgtgaag ttgttgacca ggttgaaaaa gacccgcgta acgtcgatat    840
cgcactggaa tacctgggca aatccaaagg tatccaacgc gcgcgtgaac tggctatgga    900
gcacgccaac ctggcagcag cagcaattgg ctctctgccg gaaaccgaca cgaagatgt    960 taaacgcagc cgtcgtgcac tgatcgacct gactcatcgt gtaatcaccc gcaacaaata   1020
agattgagtg atgttcctga gcatccacca gaacattccg cactttatct gtcgtattct   1080
gctggtgcaa ttcgtaagcc gctgataata ggagctc                             1117

<210> SEQ ID NO 3
<211> LENGTH: 5050
<212> TYPE: DNA
<213> ORGANISM: Artificial Sequence
<220> FEATURE:
<223> OTHER INFORMATION: ERG20-PGAL-tHMGR insert of pAM489

<400> SEQUENCE: 3
gtttaaacta ctattagctg aattgccact gctatcgttg ttagtggcgt tagtgcttgc     60
attcaaagac atggagggcg ttattacgcc ggagctcctc gacagcagat ctgatgactg    120
gtcaatatat ttttgcattg aggctctgtt tggaattata ttttgagatg acccatctaa    180
tgtactggta tcaccagatt tcatgtcgtt ttttaaagcg gctgcttgag tcttagcaat    240
agcgtcacca tctggtgaat cctttgaagg aaccactgac gaaggtttgg acagtgacga    300
agaggatctt tcctgctttg aattagtcgc gctgggagca gatgacgagt tggtggagct    360
gggggcagga ttgctggccg tcgtgggtcc tgaatgggtc cttggctggt ccatctctat    420
tctgaaaacg gaagaggagt agggaatatt actggctgaa aataagtctt gaatgaacgt    480
atacgcgtat atttctacca atctctcaac actgagtaat ggtagttata agaaagagac    540
cgagttaggg acagttagag gcggtggaga tattccttat ggcatgtctg gcgatgataa    600
aacttttcaa acggcagccc cgatctaaaa gagctgacac ccgggagtta tgacaattac    660
aacaacagaa ttctttctat atatgcacga acttgtaata tggaagaaat tatgacgtac    720
aaactataaa gtaaatattt tacgtaacac atggtgctgt tgtgcttctt tttcaagaga    780
ataccaatga cgtatgacta agtttaggat ttaatgcagg tgacggaccc atctttcaaa    840
cgatttatat cagtggcgtc caaattgtta ggttttgttg gttcagcagg tttcctgttg    900
tgggtcatat gactttgaac caaatggccg gctgctaggg cagcacataa ggataattca    960
cctgccaaga cggcacaggc aactattctt gctaattgac gtgcgttggt accaggagcg   1020
gtagcatgtg ggcctcttac acctaataag tccaacatgg caccttgtgg ttctagaaca   1080
gtaccaccac cgatggtacc tacttcgatg gatggcatgg atacggaaat tctcaaatca   1140
ccgtccactt ctttcatcaa tgttatacag ttggaacttt cgacattttg tgcaggatct   1200
tgtcctaatg ccaagaaaac agctgtcact aaattagctg catgtgcgtt aaatccacca   1260
acagacccag ccattgcaga tccaaccaaa ttcttagcaa tgttcaactc aaccaatgcg   1320
gaaacatcac ttttttaacac ttttctgaca acatcaccag gaatagtagc ttctgcgacg   1380
acactcttac cacgaccttc gatccagttg atggcagctg gttttttgtc ggtacagtag   1440
ttaccagaaa cggagacaac ctccatatct tcccagccat actcttctac catttgcttt   1500
aatgagtatt cgacacccctt agaaatcata ttcatacccca ttgcgtcacc agtagttgtt   1560
ctaaatctca tgaagagtaa atctcctgct agacaagttt gaatatgttg cagacgtgca   1620
```

```
aatcttgatg tagagttaaa agcttttta attgcgtttt gtccctcttc tgagtctaac    1680
catatcttac aggcaccaga tcttttcaaa gttgggaaac ggactactgg gcctcttgtc    1740
ataccatcct tagttaaaac agttgttgca ccaccgccag cattgattgc cttacagcca    1800
cgcatggcag aagctaccaa acaaccctct gtagttgcca ttggtatatg ataagatgta    1860
ccatcgataa ccaaggggcc tataacacca acgggcaaag gcatgtaacc tataacattt    1920
tcacaacaag cgccaaatac gcggtcgtag tcataatttt tatatggtaa acgatcagat    1980
gctaatacag gagcttctgc caaaattgaa agagccttcc tacgtaccgc aaccgctctc    2040
gtagtatcac ctaattttt ctccaaagcg tacaaaggta acttaccgtg aataaccaag    2100
gcagcgacct ctttgttctt caattgtttt gtatttccac tacttaataa tgcttctaat    2160
tcttctaaag gacgtatttt cttatccaag ctttcaatat cgcgggaatc atcttcctca    2220
ctagatgatg aaggtcctga tgagctcgat tgcgcagatg ataaactttt gactttcgat    2280
ccagaaatga ctgttttatt ggttaaaact ggtgtagaag cctttttgtac aggagcagta    2340
aaagacttct tggtgacttc agtcttcacc aattggtctg cagccattat agtttttct    2400
ccttgacgtt aaagtataga ggtatattaa caattttttg ttgatacttt tatgacatttt    2460
gaataagaag taatacaaac cgaaaatgtt gaaagtatta gttaaagtgg ttatgcagct    2520
tttgcattta tatatctgtt aatagatcaa aaatcatcgc ttcgctgatt aattccccca    2580
gaaataaggc taaaaaacta atcgcattat tatcctatgg ttgttaattt gattcgttga    2640
tttgaaggtt tgtggggcca ggttactgcc aatttttcct cttcataacc ataaaagcta    2700
gtattgtaga atctttattg ttcggagcag tgcggcgcga ggcacatctg cgtttcagga    2760
acgcgaccgg tgaagaccag gacgcacgga ggagagtctt ccgtcggagg gctgtcgccc    2820
gctcggcggc ttctaatccg tacttcaata tagcaatgag cagttaagcg tattactgaa    2880
agttccaaag agaaggtttt tttaggctaa gataatgggg ctctttacat ttccacaaca    2940
tataagtaag attagatatg gatatgtata tggtggtatt gccatgtaat atgattatta    3000
aacttctttg cgtccatcca aaaaaaagt aagaattttt gaaaattcaa tataaatggc    3060
ttcagaaaaa gaaattagga gagagagatt cttgaacgtt ttccctaaat tagtagagga    3120
attgaacgca tcgcttttgg cttacggtat gcctaaggaa gcatgtgact ggtatgccca    3180
ctcattgaac tacaacactc caggcggtaa gctaaataga ggtttgtccg ttgtggacac    3240
gtatgctatt ctctccaaca agaccgttga acaattgggg caagaagaat acgaaaaggt    3300
tgccattcta ggttggtgca ttgagttgtt gcaggcttac ttcttggtcg ccatgatgat    3360
gatggacaag tccattacca gaagaggcca accatgttgg tacaaggttc ctgaagttgg    3420
ggaaattgcc atcaatgacg cattcatgtt agaggctgct atctacaagc ttttgaaatc    3480
tcacttcaga aacgaaaaat actacataga tatcaccgaa ttgttccatg aggtcacctt    3540
ccaaaccgaa ttgggccaat tgatggactt aatcactgca cctgaagaca agtcgactt    3600
gagtaagttc tccctaaaga agcactcctt catagttact ttcaagactg cttactattc    3660
tttctacttg cctgtcgcat tggccatgta cgttgccggt atcacggatg aaaaggattt    3720
gaaacaagcc agagatgtct tgattccatt gggtgaatac ttccaaattc aagatgacta    3780
cttagactgc ttcggtaccc cagaacagat cggtaagatc ggtacagata tccaagataa    3840
caaatgttct tgggtaatca acaaggcatt ggaacttgct tccgcagaac aaagaaagac    3900
tttagacgaa aattacggta agaaggactc agtcgcagaa gccaaatgca aaagattttt    3960
caatgacttg aaaattgaac agctatacca cgaatatgaa gagtctattg ccaaggattt    4020
```

```
gaaggccaaa atttctcagg tcgatgagtc tcgtggcttc aaagctgatg tcttaactgc    4080
gttcttgaac aaagtttaca agagaagcaa atagaactaa cgctaatcga taaaacatta    4140
gatttcaaac tagataagga ccatgtataa gaactatata cttccaatat aatatagtat    4200
aagcttaaag atagtatctc tcgatctacc gttccacgtg actagtccaa ggattttttt    4260
taacccggga tatatgtgta ctttgcagtt atgacgccag atggcagtag tggaagatat    4320
tctttattga aaaatagctt gtcaccttac gtacaatctt gatccggagc ttttcttttt    4380
ttgccgatta agaattcggt cgaaaaaaga aaaggagagg gccaagaggg agggcattgg    4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaaggaaaa tttcaagtct tgtaaaagca    4680
tataaaaata gttcaggcac tccgaaatac ttggttggcg tgtttcgtaa tcaacctaag    4740
gaggatgttt tggctctggt caatgattac ggcattgata tcgtccaact gcatggagat    4800
gagtcgtggc aagaatacca agagttcctc ggtttgccag ttattaaaag actcgtattt    4860
ccaaaagact gcaacatact actcagtgca gcttcacaga aacctcattc gtttattccc    4920
ttgtttgatt cagaagcagg tgggacaggt gaacttttgg attggaactc gatttctgac    4980
tgggttggaa ggcaagagag ccccgaaagc ttacatttta tgttagctgg tggactgacg    5040
ccgtttaaac                                                           5050

<210> SEQ ID NO 4
<211> LENGTH: 5488
<212> TYPE: DNA
<213> ORGANISM: Artificial Sequence
<220> FEATURE:
<223> OTHER INFORMATION: ERG13-PGAL-tHMGR insert of pAM491

<400> SEQUENCE: 4
gtttaaactt gctaaattcg agtgaaacac aggaagacca gaaaatcctc atttcatcca      60
tattaacaat aatttcaaat gtttatttgc attatttgaa actagggaag acaagcaacg     120
aaacgttttt gaaaattttg agtattttca ataaatttgt agaggactca gatattgaaa     180
aaaagctaca gcaattaata cttgataaga agagtattga gaagggcaac ggttcatcat     240
ctcatggatc tgcacatgaa caaacaccag agtcaaacga cgttgaaatt gaggctactg     300
cgccaattga tgacaataca gacgatgata acaaaccgaa gttatctgat gtagaaaagg     360
attaaagatg ctaagagata gtgatgatat tcataaaata atgtaattct atatatgtta     420
attacctttt ttgcgaggca tatttatggt gaaggataag ttttgaccat caaagaaggt     480
taatgtggct gtggtttcag ggtccatacc cggagttat gacaattaca acaacagaat     540
tctttctata tatgcacgaa cttgtaatat ggaagaaatt atgacgtaca aactataaag     600
taaatatttt acgtaacaca tggtgctgtt gtgcttcttt ttcaagagaa taccaatgac     660
gtatgactaa gttaggatt taatgcaggt gacggaccca tctttcaaac gatttatatc     720
agtggcgtcc aaattgttag gttttgttgg ttcagcaggt ttcctgttgt gggtcatatg     780
actttgaacc aaatggccgg ctgctagggc agcacataag gataattcac ctgccaagac     840
ggcacaggca actattcttg ctaattgacg tgcgttggta ccaggagcgg tagcatgtgg     900
gcctcttaca cctaataagt ccaacatggc accttgtggt tctagaacag taccaccacc     960 gatggtaccct acttcgatgg atggcatgga tacggaaatt ctcaaatcac cgtccacttc    1020
```

```
tttcatcaat gttatacagt tggaactttc gacattttgt gcaggatctt gtcctaatgc    1080
caagaaaaca gctgtcacta aattagctgc atgtgcgtta aatccaccaa cagacccagc    1140
cattgcagat ccaaccaaat tcttagcaat gttcaactca accaatgcgg aaacatcact    1200
ttttaacact tttctgacaa catcaccagg aatagtagct tctgcgacga cactcttacc    1260
acgaccttcg atccagttga tggcagctgg ttttttgtcg gtacagtagt taccagaaac    1320
ggagacaacc tccatatctt cccagccata ctcttctacc atttgcttta atgagtattc    1380 gacacccctta gaaatcatat tcatacccat tgcgtcacca gtagttgttc taaatctcat    1440
gaagagtaaa tctcctgcta gacaagtttg aatatgttgc agacgtgcaa atcttgatgt    1500
agagttaaaa gctttttaa ttgcgttttg ccctcttct gagtctaacc atatcttaca    1560
ggcaccagat ctttcaaag ttgggaaacg gactactggg cctcttgtca taccatcctt    1620
agttaaaaca gttgttgcac caccgccagc attgattgcc ttacagccac gcatggcaga    1680
agctaccaaa caaccctctg tagttgccat tggtatatga taagatgtac catcgataac    1740 caagggggcct ataacaccaa cgggcaaagg catgtaacct ataacatttt cacaacaagc    1800
gccaaatacg cggtcgtagt cataattttt atatggtaaa cgatcagatg ctaatacagg    1860
agcttctgcc aaaattgaaa gagccttcct acgtaccgca accgctctcg tagtatcacc    1920
taattttttc tccaaagcgt acaaaggtaa cttaccgtga ataaccaagg cagcgacctc    1980
tttgttcttc aattgttttg tatttccact acttaataat gcttctaatt cttctaaagg    2040
acgtattttc ttatccaagc tttcaatatc gcgggaatca tcttcctcac tagatgatga    2100
aggtcctgat gagctcgatt gcgcagatga taaacttttg actttcgatc cagaaatgac    2160
tgttttattg gttaaaactg gtgtagaagc cttttgtaca ggagcagtaa aagacttctt    2220
ggtgacttca gtcttcacca attggtctgc agccattata gttttttctc cttgacgtta    2280
aagtatagag gtatattaac aattttttgt tgatactttt atgacatttg aataagaagt    2340
aatacaaacc gaaaatgttg aaagtattag ttaaagtggt tatgcagctt ttgcatttat    2400
atatctgtta atagatcaaa aatcatcgct tcgctgatta attacccag aaataaggct    2460 aaaaaactaa tcgcattatt atcctatggt tgttaatttg attcgttgat ttgaaggttt    2520
gtggggccag ttactgcca attttcctc ttcataacca taaaagctag tattgtagaa    2580
tctttattgt tcggagcagt gcggcgcgag gcacatctgc gtttcaggaa cgcgaccggt    2640
gaagaccagg acgcacggag gagagtcttc cgtcggaggg ctgtcgcccg ctcggcggct    2700
tctaatccgt acttcaatat agcaatgagc agttaagcgt attactgaaa gttccaaaga    2760
gaaggttttt ttaggctaag ataatggggc tctttacatt tccacaacat ataagtaaga    2820
ttagatatgg atatgtatat ggtggtattg ccatgtaata tgattattaa acttctttgc    2880
gtccatccaa aaaaaagta agaattttg aaaattcaat ataatgaaa ctctcaacta    2940 aactttgttg gtgtggtatt aaaggaagac ttaggccgca aaagcaacaa caattacaca    3000
atacaaactt gcaaatgact gaactaaaaa aacaaaagac cgctgaacaa aaaaccagac    3060
ctcaaaatgt cggtattaaa ggtatccaaa tttacatccc aactcaatgt gtcaaccaat    3120
ctgagctaga gaaatttgat ggcgtttctc aaggtaaata cacaattggt ctgggccaaa    3180
ccaacatgtc ttttgtcaat gacagagaag atatctactc gatgtcccta actgttttgt    3240
ctaagttgat caagagttac aacatcgaca ccaacaaaat tggtagatta gaagtcggta    3300
ctgaaactct gattgacaag tccaagtctg tcaagtctgt cttgatgcaa ttgtttggtg    3360
aaaacactga cgtcgaaggt attgacacgc ttaatgcctg ttacggtggt accaacgcgt    3420
```

```
tgttcaactc tttgaactgg attgaatcta acgcatggga tggtagagac gccattgtag    3480
tttgcggtga tattgccatc tacgataagg gtgccgcaag accaaccggt ggtgccggta    3540
ctgttgctat gtggatcggt cctgatgctc aattgtatt tgactctgta agagcttctt     3600
acatggaaca cgcctacgat ttttacaagc cagatttcac cagcgaatat ccttacgtcg    3660
atggtcattt ttcattaact tgttacgtca aggctcttga tcaagtttac aagagttatt    3720
ccaagaaggc tatttctaaa gggttggtta gcgatcccgc tggttcggat gctttgaacg    3780
ttttgaaata tttcgactac aacgttttcc atgttccaac ctgtaaattg gtcacaaaat    3840
catacggtag attactatat aacgatttca gagccaatcc tcaattgttc ccagaagttg    3900
acgccgaatt agctactcgc gattatgacg aatctttaac cgataagaac attgaaaaaa    3960
cttttgttaa tgttgctaag ccattccaca agagagagt tgcccaatct ttgattgttc      4020
caacaaacac aggtaacatg tacaccgcat ctgtttatgc cgcctttgca tctctattaa    4080
actatgttgg atctgacgac ttacaaggca agcgtgttgg tttatttct tacggttccg     4140
gtttagctgc atctctatat tcttgcaaaa ttgttggtga cgtccaacat attatcaagg    4200
aattagatat tactaacaaa ttagccaaga gaatcaccga aactccaaag gattacgaag    4260
ctgccatcga attgagagaa aatgcccatt tgaagaagaa cttcaaacct caaggttcca    4320
ttgagcattt gcaaagtggt gtttactact tgaccaacat cgatgacaaa tttagaagat    4380
cttacgatgt taaaaaataa tcttccccca tcgattgcat cttgctgaac cccttcata     4440
aatgctttat tttttttggca gcctgctttt tttagctctc atttaataga gtagttttt    4500
aatctatata ctaggaaaac tcttatttta ataacaatga tatatatata cccgggaagc    4560
ttttcaattc atcttttttt ttttttgttct tttttttgat tccggtttct ttgaaatttt    4620
tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaaacctg caggaaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actggagtta    4920
gttgaagcat taggtcccaa aatttgttta ctaaaaacac atgtggatat cttgactgat    4980
ttttccatgg agggcacagt taagccgcta aaggcattat ccgccaagta caatttttta    5040
ctcttcgaag acagaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaggaacc tagaggcctt     5220
ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                       5488
```

<210> SEQ ID NO 5
<211> LENGTH: 4933
<212> TYPE: DNA
<213> ORGANISM: Artificial Sequence
<220> FEATURE:
<223> OTHER INFORMATION: IDI1-PGAL-tHMGR insert of pAM493

<400> SEQUENCE: 5

```
gtttaaacta ctcagtatat taagtttcga attgaagggc gaactcttat tcgaagtcgg      60
agtcaccaca acacttccgc ccatactctc cgaatcctcg tttcctaaag taagtttact     120
tccacttgta ggcctattat taatgatatc tgaataatcc tctattaggg ttggatcatt     180
cagtagcgcg tgcgattgaa aggagtccat gcccgacgtc gacgtgatta gcgaaggcgc     240
gtaaccattg tcatgtctag cagctataga actaacctcc ttgacaccac ttgcggaagt     300
ctcatcaaca tgctcttcct tattactcat tctcttacca agcagagaat gttatctaaa     360
aactacgtgt atttcacctc tttctcgact tgaacacgtc caactcctta agtactacca     420
cagccaggaa agaatggatc cagttctaca cgatagcaaa gcagaaaaca caaccagcgt     480 accccctgtag aagcttcttt gtttacagca cttgatccat gtagccatac tcgaaatttc     540
aactcatctg aaacttttcc tgaaggttga aaaagaatgc cataagggtc acccgaagct     600
tattcacgcc cgggagttat gacaattaca acaacagaat tctttctata tatgcacgaa     660
cttgtaatat ggaagaaatt atgacgtaca aactataaag taaatatttt acgtaacaca     720
tggtgctgtt gtgcttcttt ttcaagagaa taccaatgac gtatgactaa gtttaggatt     780
taatgcaggt gacggaccca tctttcaaac gatttatatc agtggcgtcc aaattgttag     840
gttttgttgg ttcagcaggt ttcctgttgt gggtcatatg actttgaacc aaatggccgg     900
ctgctagggc agcacataag gataattcac ctgccaagac ggcacaggca actattcttg     960
ctaattgacg tgcgttggta ccaggagcgg tagcatgtgg gcctcttaca cctaataagt    1020
ccaacatggc accttgtggt tctagaacag taccaccacc gatggtacct acttcgatgg    1080
atggcatgga tacggaaatt ctcaaatcac cgtccacttc tttcatcaat gttatacagt    1140
tggaactttc gacattttgt gcaggatctt gtcctaatgc caagaaaaca gctgtcacta    1200
aattagctgc atgtgcgtta aatccaccaa cagacccagc cattgcagat ccaaccaaat    1260
tcttagcaat gttcaactca accaatgcgg aaacatcact ttttaacact tttctgacaa    1320
catcaccagg aatagtagct tctgcgacga cactcttacc acgaccttcg atccagttga    1380
tggcagctgg tttttttgtcg gtacagtagt taccagaaac ggagacaacc tccatatctt    1440
cccagccata ctcttctacc atttgcttta atgagtattc gacaccctta gaaatcatat    1500
tcatacccat tgcgtcacca gtagttgttc taaatctcat gaagagtaaa tctcctgcta    1560
gacaagtttg aatatgttgc agacgtgcaa atcttgatgt agagttaaaa gcttttttaa    1620
ttgcgttttg tccctcttct gagtctaacc atatcttaca ggcaccagat cttttcaaag    1680
ttgggaaacg gactactggg cctcttgtca taccatcctt agttaaaaca gttgttgcac    1740
caccgccagc attgattgcc ttacagccac gcatggcaga agctaccaaa caaccctctg    1800
tagttgccat tggtatatga taagatgtac catcgataac caaggggcct ataacaccaa    1860
cgggcaaagg catgtaacct ataacatttt cacaacaagc gccaaatacg cggtcgtagt    1920
cataattttt tatatggtaaa cgatcagatg ctaatacagg agcttctgcc aaaattgaaa    1980
gagccttcct acgtaccgca accgctctcg tagtatcacc taatttttc tccaaagcgt     2040 acaaaggtaa cttaccgtga ataaccaagg cagccgacct tttgttcttc aattgttttg    2100
tatttccact acttaataat gcttctaatt cttctaaagg acgtattttc ttatccaagc    2160
tttcaatatc gcgggaatca tcttcctcac tagatgatga aggtcctgat gagctcgatt    2220
gcgcagatga taaacttttg actttcgatc cagaaatgac tgttttattg gttaaaactg    2280
gtgtagaagc cttttgtaca ggagcagtaa aagacttctt ggtgacttca gttttccaca    2340
attggtctgc agccattata gttttttctc cttgacgtta aagtatagag gtatattaac    2400
```

```
aattttttgt tgatacttttt atgacatttg aataagaagt aatacaaacc gaaaatgttg    2460
aaagtattag ttaaagtggt tatgcagctt ttgcatttat atatctgtta atagatcaaa    2520
aatcatcgct tcgctgatta attacccag  aaataaggct aaaaaactaa tcgcattatt    2580
atcctatggt tgttaatttg attcgttgat ttgaaggttt gtggggccag gttactgcca    2640
atttttcctc ttcataacca taaaagctag tattgtagaa tctttattgt tcggagcagt    2700
gcggcgcgag gcacatctgc gtttcaggaa cgcgaccggt gaagaccagg acgcacggag    2760
gagagtcttc cgtcggaggg ctgtcgcccg ctcggcggct tctaatccgt acttcaatat    2820
agcaatgagc agttaagcgt attactgaaa gttccaaaga gaaggttttt ttaggctaag    2880 ataatgggc  tctttacatt tccacaacat ataagtaaga ttagatatgg atatgtatat    2940
ggtggtattg ccatgtaata tgattattaa acttctttgc gtccatccaa aaaaaaagta    3000 agaattttg  aaaattcaat ataaatgact gccgacaaca atagtatgcc ccatggtgca    3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aaaggggttta ctacatcgtg cattctccgt ctttattttc    3360
aatgaacaag gtgaattact tttacaacaa agagccactg aaaaaataac tttccctgat    3420
ctttggacta acacatgctg ctctcatcca ctatgtattg atgacgaatt aggtttgaag    3480
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660
ttttataaga tcaacgctaa agaaaacttg actgtcaacc caaacgtcaa tgaagttaga    3720
gacttcaaat gggtttcacc aaatgatttg aaaactatgt ttgctgaccc aagttacaag    3780
tttacgcctt ggtttaagat tatttgcgag aattacttat tcaactggtg ggagcaatta    3840
gatgaccttt ctgaagtgga aaatgacagg caaattcata gaatgctata acaacgcgtc    3900
aataatatag gctacataaa aatcataata actttgttat catagcaaaa tgtgatataa    3960
aacgtttcat ttcacctgaa aaatagtaaa aataggcgac aaaaatcctt agtaatatgt    4020
aaactttatt ttctttattt acccgggagt cagtctgact cttgcgagag atgaggatgt    4080
aataatacta atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
ttgaccaaac tgtcagagtt ctggttcaag ttcctgtcca acgatgttcg taatcatttg    4500
gtcgacatcg ccccaggtaa gactatttc  gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
```

-continued

| | |
|---|---|
| gcccaggccg ctgagctggt gggtgaagat ttgtcacgta gagtggcaga actggctgta | 4860 |
| aaactgtact ccaagtgcaa agattatgct aaggagaagg gcatcatcat cgcagacact | 4920 |
| aaattgttta aac | 4933 |

<210> SEQ ID NO 6
<211> LENGTH: 6408
<212> TYPE: DNA
<213> ORGANISM: Artificial Sequence
<220> FEATURE:
<223> OTHER INFORMATION: ERG10-PGAL-ERG12 insert of pAM495

<400> SEQUENCE: 6

| | |
|---|---|
| gtttaaacta ttgtgagggt cagttatttc atccagatat aacccgagag gaaacttctt | 60 |
| agcgtctgtt ttcgtaccat aaggcagttc atgaggtata ttttcgttat tgaagcccag | 120 |
| ctcgtgaatg cttaatgctg ctgaactggt gtccatgtcg cctaggtacg caatctccac | 180 |
| aggctgcaaa ggttttgtct caagagcaat gttattgtgc accccgtaat tggtcaacaa | 240 |
| gtttaatctg tgcttgtcca ccagctctgt cgtaaccttc agttcatcga ctatctgaag | 300 |
| aaatttacta ggaatagtgc catggtacag caaccgagaa tggcaatttc tactcgggtt | 360 |
| cagcaacgct gcataaacgc tgttggtgcc gtagacatat tcgaagatag gattatcatt | 420 |
| cataagtttc agagcaatgt ccttattctg gaacttggat ttatggctct tttggtttaa | 480 |
| tttcgcctga ttcttgatct cctttagctt ctcgacgtgg gccttttttct tgccatatgg | 540 |
| atccgctgca cggtcctgtt ccctagcatg tacgtgagcg tatttccttt taaaccacga | 600 |
| cgctttgtct tcattcaacg tttcccattg ttttttttcta ctattgcttt gctgtgggaa | 660 |
| aaacttatcg aaagatgacg acttttttctt aattctcgtt ttaagagctt ggtgagcgct | 720 |
| aggagtcact gccaggtatc gtttgaacac ggcattagtc agggaagtca taacacagtc | 780 |
| cttcccgca atttcttttt tctattactc ttggcctcct ctagtacact ctatatttt | 840 |
| ttatgcctcg gtaatgattt tcatttttt ttttttcacc tagcggatga ctctttttt | 900 |
| ttcttagcga ttggcattat cacataatga attatacatt atataaagta atgtgatttc | 960 |
| ttcgaagaat atactaaagt ttagcttgcc tcgtccccgc cgggtcaccc ggccagcgac | 1020 |
| atggaggccc agaatacccct ccttgacagt cttgacgtgc gcagctcagg ggcatgatgt | 1080 |
| gactgtcgcc cgtacattta gcccatacat ccccatgtat aatcatttgc atccatacat | 1140 |
| tttgatggcc gcacggcgcg aagcaaaaat tacggctcct cgctgcagac ctgcgagcag | 1200 |
| ggaaacgctc ccctcacaga cgcgttgaat tgtcccacg ccgcgcccct gtagagaaat | 1260 |
| ataaaaggtt aggatttgcc actgaggttc ttctttcata tacttccttt taaaatcttg | 1320 |
| ctaggataca gttctcacat cacatccgaa cataaacaac catggcagaa ccagcccaaa | 1380 |
| aaaagcaaaa acaaactgtt caggagcgca aggcgtttat ctcccgtatc actaatgaaa | 1440 |
| ctaaaattca atcgctatt tcgctgaatg gtggttatat tcaaataaaa gattcgattc | 1500 |
| ttcctgcaaa gaaggatgac gatgtagctt cccaagctac tcagtcacag gtcatcgata | 1560 |
| ttcacacagg tgttggcttt ttggatcata tgatccatgc gttggcaaaa cactctctgg tt | 1620 |
| ggtctcttat tgttgaatgt attggtgacc tgcacattga cgatcaccat actaccgaag | 1680 |
| attgcggtat cgcattaggg caagcgttca aagaagcaat gggtgctgtc cgtggtgtaa | 1740 |
| aaagattcgg tactgggttc gcaccattgg atgaggcgct atcacgtgcc gtagtcgatt | 1800 |
| tatcagtag accatttgct gtaatcgacc ttgattgaa gagagagatg attggtgatt | 1860 |
| tatccactga aatgattcca cactttttgg aaagtttcgc ggaggcggcc agaattactt | 1920 |

```
tgcatgttga ttgtctgaga ggtttcaacg atcaccacag aagtgagagt gcgttcaagg    1980
ctttggctgt tgccataaga gaagctattt ctagcaatgg caccaatgac gttccctcaa    2040
ccaaaggtgt tttgatgtga agtactgaca ataaaaagat tcttgttttc aagaacttgt    2100
catttgtata gttttttttat attgtagttg ttctatttta atcaaatgtt agcgtgattt    2160 atatttttt tcgcctcgac atcatctgcc cagatgcgaa gttaagtgcg cagaaagtaa    2220
tatcatgcgt caatcgtatg tgaatgctgg tcgctatact gctgtcgatt cgatactaac    2280
gccgccatcc acccgggatg gtctgcttaa atttcattct gtcttcgaaa gctgaattga    2340
tactacgaaa aattttttttt tgtttctctt tctatcttta ttacataaaa cttcatacac    2400
agttaagatt aaaaacaact aataaataat gcctatcgca aattagctta tgaagtccat    2460
ggtaaattcg tgtttcctgg caataataga tcgtcaattt gttgctttgt ggtagtttta    2520
ttttcaaata attggaatac tagggatttg attttaagat cttattcaa attttttgcg    2580 cttaacaaac agcagccagt cccacccaag tctgtttcaa atgtctcgta actaaaatca    2640
tcttgcaatt tcttttttgaa actgtcaatt tgctcttgag taatgtctct tcgtaacaaa    2700
gtcaaagagc aaccgccgcc accagcaccg gtaagttttg tggagccaat tctcaaatca    2760
tcgctcagat ttttaataag ttctaatcca ggatgagaaa caccgattga gacaagcagt    2820
ccatgattta ttcttatcaa ttccaatagt tgttcataca gttcattatt agtttctaca    2880
gcctcgtcat cggtgccttt acatttactt aacttagtca tgatctctaa gccttgtagg    2940
gcacattcac cctggcatc tagaattggc ttcataactt caggaaattt ctcggtgacc    3000
aacacacgaa cgcgagcaac aagatctttt gtagaccttg gaattctagt ataggttagg    3060
atcattggaa tggctgggaa atcatctaag aacttaaaat tgtttgtgtt tattgttcca    3120
ttatgtgagt cttttttcaaa tagcagggca ttaccataag tggccacagc gttatctatt    3180
cctgaagggg taccgtgaat acacttttca cctatgaagg cccattgatt cactatatgc    3240
ttatcgtttt ctgacagctt ttccaagtca ttagatccta ttaacccccc caagtaggcc    3300
atagctaagg ccagtgatac agaaatagag gcgcttgagc ccaacccagc accgatgggt    3360
aaagtagact ttaaagaaaa cttaatattc ttggcatggg ggcataggca aacaaacata    3420
tacaggaaac aaaacgctgc atggtagtgg aaggattcgg atagttgagc taacaacgga    3480
tccaaaagac taacgagttc ctgagacaag ccatcggtgg cttgttgagc cttggccaat    3540
ttttgggagt ttacttgatc ctcggtgatg gcattgaaat cattgatgga ccacttatga    3600
ttaaagctaa tgtccgggaa gtccaattca atagtatctg gtgcagatga ctcgcttatt    3660
agcaggtagg ttctcaacgc agacacacta gcagcgacgg caggcttgtt gtacacagca    3720
gagtgttcac caaaaataat aacctttccc ggtgcagaag ttaagaacgg taatgacatt    3780 atagttttttt ctccttgacg ttaaagtata gaggtatatt aacaattttt tgttgatact    3840
tttatgacat ttgaataaga agtaatacaa accgaaaatg ttgaaagtat tagttaaagt    3900
ggttatgcag cttttgcatt tatatatctg ttaatagatc aaaaatcatc gcttcgctga    3960
ttaattaccc cagaaataag gctaaaaaac taatcgcatt attatcctat ggttgttaat    4020
ttgattcgtt gatttgaagg tttgtggggc caggttactg ccaattttttc ctcttcataa    4080 ccataaaagc tagtattgta gaatctttat tgttcggagc agtgcggcgc gaggcacatc    4140
tgcgtttcag gaacgcgacc ggtgaagacc aggacgcacg gaggagagtc ttccgtcgga    4200
gggctgtcgc ccgctcggcg gcttctaatc cgtacttcaa tatagcaatg agcagttaag    4260
cgtattactg aaagttccaa agagaaggtt ttttaggct aagataatgg ggctctttac    4320
```

```
atttccacaa catataagta agattagata tggatatgta tatggtggta ttgccatgta    4380
atatgattat taaacttctt tgcgtccatc caaaaaaaaa gtaagaattt ttgaaaattc    4440
aatataaatg tctcagaacg tttacattgt atcgactgcc agaaccccaa ttggttcatt    4500
ccagggttct ctatcctcca agacagcagt ggaattgggt gctgttgctt taaaaggcgc    4560
cttggctaag gttccagaat tggatgcatc caaggatttt gacgaaatta ttttggtaa    4620
cgttctttct gccaatttgg gccaagctcc ggccagacaa gttgctttgg ctgccggttt    4680
gagtaatcat atcgttgcaa gcacagttaa caaggtctgt gcatccgcta tgaaggcaat    4740
cattttgggt gctcaatcca tcaaatgtgg taatgctgat gttgtcgtag ctggtggttg    4800
tgaatctatg actaacgcac catactacat gccagcagcc cgtgcgggtg ccaaatttgg    4860
ccaaactgtt cttgttgatg gtgtcgaaag agatgggttg aacgatgcgt acgatggtct    4920
agccatgggt gtacacgcag aaaagtgtgc ccgtgattgg gatattacta gagaacaaca    4980
agacaatttt gccatcgaat cctaccaaaa atctcaaaaa tctcaaaagg aaggtaaatt    5040
cgacaatgaa attgtacctg ttaccattaa gggatttaga ggtaagcctg atactcaagt    5100
cacgaaggac gaggaacctg ctagattaca cgttgaaaaa ttgagatctg caaggactgt    5160
tttccaaaaa gaaaacggta ctgttactgc cgctaacgct tctccaatca acgatggtgc    5220
tgcagccgtc atcttggttt ccgaaaaagt tttgaaggaa aagaatttga agcctttggc    5280
tattatcaaa ggttggggtg aggccgctca tcaaccagct gattttacat gggctccatc    5340
tcttgcagtt ccaaaggctt tgaaacatgc tggcatcgaa gacatcaatt ctgttgatta    5400
ctttgaattc aatgaagcct tttcggttgt cggtttggtg aacactaaga ttttgaagct    5460
agacccatct aaggttaatg tatatggtgg tgctgttgct ctaggtcacc cattgggttg    5520
ttctggtgct agagtggttg ttacactgct atccatctta cagcaagaag gaggtaagat    5580
cggtgttgcc gccatttgta atggtggtgg tggtgcttcc tctattgtca ttgaaaagat    5640
atgattacgt tctgcgattt tctcatgatc ttttttcataa aatacataaa tatataaatg    5700
gctttatgta taacaggcat aatttaaagt tttatttgcg attcatcgtt tttcaggtac    5760
tcaaacgctg aggtgtgcct tttgacttac ttttcccggg agaggctagc agaattaccc    5820
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940
ccaaaggtgt tcttatgtag tgacaccgat tatttaaagc tgcagcatac gatatatata    6000
catgtgtata tatgtatacc tatgaatgtc agtaagtatg tatacgaaca gtatgatact    6060
gaagatgaca aggtaatgca tcattctata cgtgtcattc tgaacgaggc gcgctttcct    6120
ttttctttt tgcttttttct tttttttcct cttgaactcg agaaaaaaaa tataaaagag    6180
atggaggaac gggaaaaagt tagttgtggt gataggtggc aagtggtatt ccgtaagaac    6240
aacaagaaaa gcatttcata ttatggctga actgagcgaa caagtgcaaa atttaagcat    6300
caacgacaac aacgagaatg ttatgttcc tcctcactta agaggaaaac caagaagtgc    6360
cagaaataac agtagcaact acaataacaa caacggcggc gtttaaac                6408
```

<210> SEQ ID NO 7
<211> LENGTH: 6087
<212> TYPE: DNA
<213> ORGANISM: Artificial Sequence
<220> FEATURE:
<223> OTHER INFORMATION: ERG8-PGAL-ERG19 insert of pAM497

<400> SEQUENCE: 7

```
gtttaaactt ttccaatagg tggttagcaa tcgtcttact ttctaacttt tcttaccttt    60
tacatttcag caatatatat atatatattt caaggatata ccattctaat gtctgccct    120 aagaagatcg tcgttttgcc aggtgaccac gttggtcaag aaatcacagc cgaagccatt   180
aaggttctta aagctatttc tgatgttcgt tccaatgtca agttcgattt cgaaaatcat   240
ttaattggtg gtgctgctat cgatgctaca ggtgttccac ttccagatga ggcgctggaa   300
gcctccaaga aggctgatgc cgttttgtta ggtgctgtgg gtggtcctaa atggggtacc   360
ggtagtgtta gacctgaaca aggtttacta aaaatccgta agaacttca attgtacgcc   420 aacttaagac catgtaactt tgcatccgac tctcttttag acttatctcc aatcaagcca   480
caatttgcta aaggtactga cttcgttgtt gtcagagaat tagtgggagg tatttacttt   540
ggtaagagaa aggaagacgt ttagcttgcc tcgtccccgc cgggtcaccc ggccagcgac   600
atggaggccc agaataccct ccttgacagt cttgacgtgc gcagctcagg ggcatgatgt   660
gactgtcgcc cgtacattta gcccatacat ccccatgtat aatcatttgc atccatacat   720
tttgatggcc gcacggcgcg aagcaaaaat tacggctcct cgctgcagac ctgcgagcag   780
ggaaacgctc ccctcacaga cgcgttgaat tgtccccacg ccgcgcccct gtagagaaat   840
ataaaaggtt aggatttgcc actgaggttc ttctttcata tacttccttt taaaatcttg   900
ctaggataca gttctcacat cacatccgaa cataaacaac catggcagaa ccagcccaaa   960
aaaagcaaaa acaaactgtt caggagcgca aggcgtttat ctcccgtatc actaatgaaa  1020
ctaaaattca aatcgctatt tcgctgaatg gtggttatat tcaaataaaa gattcgattc  1080
ttcctgcaaa gaaggatgac gatgtagctt cccaagctac tcagtcacag gtcatcgata  1140
ttcacacagg tgttggcttt ttggatcata tgatccatgc gttggcaaaa cactctggtt  1200
ggtctcttat tgttgaatgt attggtgacc tgcacattga cgatcaccat actaccgaag  1260
attgcggtat cgcattaggg caagcgttca agaagcaat gggtgctgtc cgtggtgtaa  1320
aaagattcgg tactgggttc gcaccattgg atgaggcgct atcacgtgcc gtagtcgatt  1380
tatctagtag accatttgct gtaatcgacc ttggattgaa gagagagatg attggtgatt  1440
tatccactga aatgattcca cactttttgg aaagtttcgc ggaggcggcc agaattactt  1500
tgcatgttga ttgtctgaga ggtttcaacg atcaccacag aagtgagagt gcgttcaagg  1560 cttttggctgt tgccataaga gaagctattt ctagcaatgg caccaatgac gttccctcaa  1620
ccaaaggtgt tttgatgtga agtactgaca ataaaaagat tcttgttttc aagaacttgt  1680
catttgtata gttttttttat attgtagttg ttctattta atcaaatgtt agcgtgattt  1740
atattttttt tcgcctcgac atcatctgcc cagatgcgaa gttaagtgcg cagaaagtaa  1800
tatcatgcgt caatcgtatg tgaatgctgg tcgctatact gctgtcgatt cgatactaac  1860
gccgccatcc acccgggttt ctcattcaag tggtaactgc tgttaaaatt aagatattta  1920
taaattgaag cttggtcgtt ccgaccaata ccgtagggaa acgtaaatta gctattgtaa  1980
aaaaaggaaa agaaaagaaa agaaaaatgt tacatatcga attgatctta ttcctttggt  2040
agaccagtct ttgcgtcaat caaagattcg tttgtttctt gtgggcctga accgacttga  2100
gttaaaatca ctctggcaac atcctttgc aactcaagat ccaattcacg tgcagtaaag  2160
ttagatgatt caaattgatg gttgaaagcc tcagctgct cagtagtaaa tttcttgtcc  2220
catccaggaa cagagccaaa caatttatag ataaatgcaa agagtttcga ctcatttca   2280 gctaagtagt acaacacagc atttggacct gcatcaaacg tgtatgcaac gattgtttct  2340
ccgtaaaact gattaatggt gtggcaccaa ctgatgatac gcttggaagt gtcattcatg  2400
```

```
tagaatattg gagggaaaga gtccaaacat gtggcatgga aagagttgga atccatcatt    2460
gtttcctttg caaaggtggc gaaatctttt tcaacaatgg ctttacgcat gacttcaaat    2520
ctctttggta cgacatgttc aattctttct ttaaatagtt cggaggttgc cacggtcaat    2580
tgcataccct gagtggaact cacatccttt taatatcgc tgacaactag gacacaagct    2640
ttcatctgag gccagtcaga gctgtctgcg atttgtactg ccatggaatc atgaccatct    2700
tcagcttttc ccatttccca ggccacgtat ccgccaaaca acgatctaca agctgaacca    2760 gaccccttc ttgctattct agatatttct gaagttgact gtggtaattg gtataactta    2820
gcaattgcag agaccaatgc agcaaagcca gcagcgagg aagctaaacc agctgctgta    2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc cttttccccc aatacttaag ggttgcgatg    3180
ttgacgggtg cggtaacgga tgctgtgtaa acggtcatta tagttttttc tccttgacgt    3240
taaagtatag aggtatatta acaattttt gttgatactt ttatgacatt tgaataagaa    3300
gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caatttttcc tcttcataac cataaaagct agtattgtag    3540
aatctttatt gttcggagca gtgcggcgcg aggcacatct gcgtttcagg aacgcgaccg    3600
gtgaagacca ggacgcacgg aggagagtct tccgtcggag ggctgtcgcc cgctcggcgg    3660
cttctaatcc gtacttcaat atagcaatga gcagttaagc gtattactga aagttccaaa    3720
gagaaggttt tttaggcta agataatggg gctctttaca tttccacaac atataagtaa    3780
gattagatat ggatatgtat atggtggtat tgccatgtaa tatgattatt aaacttcttt    3840
gcgtccatcc aaaaaaaaag taagaatttt tgaaaattca atataaatgt cagagttgag    3900
agccttcagt gccccaggga aagcgttact agctggtgga tatttagttt tagatccgaa    3960
atatgaagca tttgtagtcg gattatcggc aagaatgcat gctgtagccc atccttacgg    4020
ttcattgcaa gagtctgata agtttgaagt gcgtgtgaaa agtaaacaat ttaaagatgg    4080
ggagtggctg taccatataa gtcctaaaac tggcttcatt cctgtttcga taggcggatc    4140
taagaaccct ttcattgaaa aagttatcgc taacgtattt agctacttta agcctaacat    4200
ggacgactac tgcaatagaa acttgttcgt tattgatatt ttctctgatg atgcctacca    4260
ttctcaggag gacagcgtta ccgaacatcg tggcaacaga agattgagtt tcattcgca    4320 cagaattgaa gaagttccca aaacagggct gggctcctcg gcaggtttag tcacagtttt    4380
aactacagct ttggcctcct ttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
```

```
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttcctttta gaaaaataac   4980
taaagaatct ggtgccgata tcgaacctcc cgtacaaact agcttattgg atgattgcca    5040
gaccttaaaa ggagttctta cttgcttaat acctggtgct ggtggttatg acgccattgc    5100
agtgattgct aagcaagatg ttgatcttag ggctcaaacc gctgatgaca aaagattttc    5160
taaggttcaa tggctggatg taactcaggc tgactggggt gttaggaaag aaaaagatcc    5220
ggaaacttat cttgataaat aacttaaggt agataatagt ggtccatgtg acatctttat    5280
aaatgtgaag tttgaagtga ccgcgcttaa catctaacca ttcatcttcc gatagtactt    5340
gaaattgttc ctttcggcgg catgataaaa ttctttttaat gggtacaagc tacccgggcc    5400
cgggaaagat tctctttttt tatgatattt gtacataaac tttataaatg aaattcataa    5460
tagaaacgac acgaaattac aaaatggaat atgttcatag ggtagacgaa actatatacg    5520
caatctacat acatttatca agaaggagaa aaaggaggat gtaaaggaat acaggtaagc    5580
aaattgatac taatggctca acgtgataag gaaaagaat tgcactttaa cattaatatt     5640
gacaaggagg agggcaccac acaaaaagtt aggtgtaaca gaaaatcatg aaactatgat    5700
tcctaattta tatattggag gattttctct aaaaaaaaaa aaatacaaca aataaaaaac    5760
actcaatgac ctgaccattt gatggagttt aagtcaatac cttcttgaac catttcccat    5820
aatggtgaaa gttccctcaa gaattttact ctgtcagaaa cggccttaac gacgtagtcg    5880
acctcctctt cagtactaaa tctaccaata ccaaatctga tggaagaatg ggctaatgca    5940
tcatccttac ccagcgcatg taaaacataa gaaggttcta gggaagcaga tgtacaggct    6000
gaacccgagg ataatgcgat atcccttagt gccatcaata aagattctcc ttccacgtag    6060
gcgaaagaaa cgttaacacg tttaaac                                        6087
```

<210> SEQ ID NO 8
<211> LENGTH: 1725
<212> TYPE: DNA
<213> ORGANISM: Artificial Sequence
<220> FEATURE:
<223> OTHER INFORMATION: gamma-terpinene synthase of Citrus limon codon-optimized for expression in Escherichia coli and with flanking XmaI and XbaI restriction sites

<400> SEQUENCE: 8

```
ggaattcccg ggcgagctct ttacacttta tgcttccggc tcgtataatg tgtggaattg      60
tgagcggata acaattgaat tcaaaggagg aaaataaaat gagcttcgat tatattcaga    120
gcctggattc taagtacaag ggtgaatctt acgcccgtca gcttgagaaa ctgaaagaac    180
aagtgtccgc aatgctgcag caggacaaca agtcgttgac ctggacccca ctgcatcagc    240
tggaactgat cgataatctg caccgtctgg gcgtgagcta ccatttcgag gatgagatca    300
aacgtaccct ggatcgtatc cacaacaaaa acaccaacaa agcttgtat gcgcgtgcgc     360
tgaaattccg catcctgcgt cagtacggct ataagacccc ggttaaggaa acgttctctc    420
gcttcatgga cgaaaaaggc agcttcaaac tgtcctctca ttctgatgaa tgcaaaggca    480
tgctggctct gtacgaagct gcatatctcc tggttgaaga agaatcttcc atcttccgtg    540
atgcgatccg ctttaccacg gcatacctga agaatgggt agcgaaacac gatattgata    600
aaacgataa cgaatatctg tgcaccttgg tgaaacacgc actggaactg ccgctgcatt    660
ggcgcatgcg tcgtctggag gctcgctggt tcatcgacgt ctatgagtct ggcccggata    720
```

```
tgaacccgat cctgctggag ctggccaaag ttgactacaa catcgttcag gctgtgcacc    780
aggaggacct gaaatacgtt tcccgttggt ggaagaaaac tggtctgggc gaaaaactga    840
acttcgcacg tgatcgtgtt gtggaaaact tcttctggac cgttggcgat atcttcgaac    900
cgcagttcgg ctactgccgc cgtatgtctg ctatggtaaa ctgtctgctg acctccattg    960
atgatgtata cgatgtttat ggtactctgg atgaacttga actgttcact gatgcggtag   1020
aacgctggga tgctaccact actgaacagt tgccttatta catgaagttg tgtttccacg   1080
cgctgtacaa ctccgtaaac gaaatgggct tcatcgctct gcgtgatcag gaagtaggta   1140
tgattattcc atatctgaag aaagcatggg cggatcagtg taaatcctac ctggtggaag   1200
caaaatggta caactctggc tacattccta ctctgcagga gtacatggag aacgcgtgga   1260
tctccgttac cgcgcctgta atgctgttgc acgcgtacgc attcaccgct aacccaatca   1320
ccaaggaagc actggaattt ctgcaggact cgccggatat catccgtatc tcctccatga   1380
tcgtgcgtct ggaagacgat ctgggtaccc cagcgatga actgaaacgt ggtgacgtcc   1440
cgaaaagcat ccagtgttac atgcacgaaa ccggcgtttc tgaagacgag gctcgtgaac   1500
atattcgtga cctcattgca gaaacctgga tgaagatgaa ctctgcgcgt ttcggtaacc   1560
cgccgtacct gccggatgtt tttatcggta tcgcgatgaa cctggtgcgt atgtcccaat   1620
gtatgtattt gtacggcgat ggtcatggtg tacaggaaaa cactaaagac cgcgtcctgt   1680
ctctgttcat cgatccgatc ccgtgatagt aatctagagg aattt            1725
```

<210> SEQ ID NO 9
<211> LENGTH: 1737
<212> TYPE: DNA
<213> ORGANISM: Artificial Sequence
<220> FEATURE:
<223> OTHER INFORMATION: terpinolene synthase of Ocimum basilicum codon-
      optimized for expression in Escherichia coli and with flanking
      XmaI and XbaI restriction sites

<400> SEQUENCE: 9

```
ggaattcccg ggcgagctct ttacacttta tgcttccggc tcgtataatg tgtggaattg     60
tgagcggata acaattgaat tcaaaggagg aaaataaaat ggattttaac tatctgcagt    120
ctctgaataa ttaccaccac aaagaggaac gttacctgcg ccgccaggcc gatctgatcg    180
aaaaagtgaa atgattctg aaagaggaga aatggaggc cctgcaacag ctggagctga    240
tcgacgacct gcgtaacctg ggcctgtctt actgctttga cgatcaaatt aaccatatcc    300
tgacgaccat ctataaccag cactcctgct tccactatca cgaagcggct acctctgagg    360
aagcgaacct gtacttcacc gccctgggtt tccgtctgct gcgcgaacac ggcttcaaag    420
tgagccagga agtgttcgat cgttttaaga acgaaaaagg caccgatttc cgtccggatc    480
tggttgatga tacccagggt ctgctgcaac tgtatgaagc aagctttctg ctgcgtgaag    540
gcgaggacac tctggaattc gcacgccaat tcgcaacgaa attcctgcaa agaaagtcg    600
aagaaaagat gattgaagaa gaaaaacctgc tgtcttggac cctgcacagc ctggaactgc    660
cgctgcactg gcgtatccag cgtctggaag cgaaatggtt cctggatgcg tacgcttctc    720
gcccagacat gaaccgatt attttcgaac tggccaaact ggaatttaat atcgctcagg    780
cactgcagca ggaagaactg aaggacctga gccgttggtg aacgatact ggtatcgcgg    840
aaaaactgcc gttcgcgcgt gatcgtatcg tggaatccca ctactgggct atcggcaccc    900
tggagccgta ccagtaccgt taccagcgct ctctgatcgc gaaaatcatc gctctgacca    960
cggtggttga cgatgtgtac gacgtttacg gtactctgga cgaactgcag ctgttcaccg   1020
```

-continued

```
atgcaatccg tcgttgggat atcgaatcta tcaaccaact gccgtcttat atgcaactgt    1080
gttacctggc gatctataac tttgtgtctg aactggccta tgacatcttc cgcgacaaag    1140
gtttcaattc cctgccgtac ctgcacaaaa gctggctgga cctggtagaa gcgtatttcc    1200
aggaggcgaa gtggtatcac agcggctaca ccccgtccct ggaacagtac ctgaacattg    1260
cacagatcag cgtggcgtct ccggcgatcc tgtctcagat ctacttcacc atggcgggca    1320
gcattgacaa accggtgatt gaaagcatgt acaaatatcg tcatattctg aatctgtccg    1380
gcatcctgct gcgtctgcca gacgatctgg gcaccgcctc cgacgaactg gccgtggtg    1440
acctggcaaa agcgatgcag tgctacatga aagagcgtaa cgttagcgaa gaagaagcgc    1500
gcgatcacgt tcgtttcctg aaccgtgaag tttccaaaca gatgaatccg gcacgtgctg    1560
ctgatgattg cccgttcact gacgattttg tggtcgcagc agccaacctg ggtcgcgtag    1620
ctgacttcat gtacgtggaa ggtgatggtc tgggcctgca ataccctgct atccaccagc    1680
acatggcgga actgctgttc catccgtatg cctaatgata gtaatctaga ggaattt       1737
```

<210> SEQ ID NO 10
<211> LENGTH: 1785
<212> TYPE: DNA
<213> ORGANISM: Artificial Sequence
<220> FEATURE:
<223> OTHER INFORMATION: terpinolene synthase of Pseudotsuga menziesii
      codon-optimized for expression in Escherichia coli and with
      flanking XmaI and XbaI restriction sites

<400> SEQUENCE: 10

```
ggaattcccg ggcgagctct ttacacttta tgcttccggc tcgtataatg tgtggaattg      60
tgagcggata caattgaat tcaaaggagg aaaataaaat ggatgacaac tttattcagt     120
ctctgtccag cccgtatgaa gaatcttctt acggcgatcg tgccgaaact ctgatcggcg    180
aagtaaagga gatcttcaac agcctgtcta tgactggtgt agttagcccg ctgaacgacc    240
tgctgcagcg tctgctgatg gtggataacg ttgagcgtct gggtatcgaa cgccacttcc    300
agaacgaaat caagagcgcc ctgcagtatg tgtactctta ctggtctgag atggtattg     360
gctgcggtaa agactccgtt agcaccgacc tgaacaccac tgcactgggc ttccgtatcc    420
tgcgcctgca tggttatacc gtgttctccg acgtactgga acagttcaaa gaccagaaag    480
gccagttcgc gagcgcttgg tccgcgaacc ataccgaacg ccaaatccgt tccgtcctga    540
acctgtttcg cgcttccctg atcgcgttcc aggtgaaaaa agtgatggaa gaggcacaaa    600
tcttctccgc gacctatctg aaagaggcgc tgcagactat cccgctgtct ggcctgtctc    660
aggaaatcca gtacgcgctg aataccgtt ggcattctaa cctgccgcgc ctggaagttc      720
gtagctatat tgatatcctg gcagaaaata ctattaacga aatgagctac ccgaaggttg    780
agaaactgct ggagctggcg aaactggaat tcaacatctt ccatagcctg cagcagaagg    840
agctgcagtg tatctggcgc tggtggaaag aatccggctc tccggagctg acgtttgtgc    900
gtcatcgtta tgtagagtac tacccctgg tggctggcat cgatatggaa ccgcagcact     960
ctgccttccg catcgcgtac gtcaagatgt gccacctgat caccattctg gatgatatgt   1020
atgatactt cggcaccatc gacgagctgc gtctgttcac tgctgccgta aaacgctggg    1080
accgtagccc gaccgagtgc ctgccgcagt acatgaaagg tgtctatatg gtgctgtacg   1140
acacggttaa tgaaatggcc tgtgaagctc tgaaaagcca gggctgggat acgctgaatt   1200
atgctcgcca ggctttcgaa gattacatcg attcttacct gaaggaggca gaatggatct   1260
ccactggtta cctgccgacc ttcgaagaat atctggaaaa cggtaaagtg tcctccgcgc   1320
```

```
accgtgttgc aaccctgcag ccgatcctga ccctggatat cccgtttcca ctgcacatca   1380
tccaggaaat cgacttcccg tccaaattta acgattccgc ttcctctatc ctgcgtctgc   1440
gtggcgatac ccgttgttat caagcggata tggcacgcgg tgaagaggca tcctctatct   1500
cctgctatat gcacgataat ccgggctcta ctgaagaaga tgcgctgaac acattaacg    1560 gtatgatcga ggacattatc aaagaactga actgggaact gctgcgtaag gacatcaacg   1620
ttccgattag ctgcaaaaag catgcgttcg aaatttctcg tggcttccac cactttttaca  1680 aagatcgcga cggttacact gtctctaaca tcgaaaccaa ggatctggta atgaaaactg   1740
tcctggaacc ggtgcctctg taatgatagt aatctagagg aattt                   1785

<210> SEQ ID NO 11
<211> LENGTH: 2121
<212> TYPE: DNA
<213> ORGANISM: Artificial Sequence
<220> FEATURE:
<223> OTHER INFORMATION: KanMX-PMET3 region from pAM328
<220> FEATURE:
<221> NAME/KEY: misc_feature
<222> LOCATION: 13, 2109
<223> OTHER INFORMATION: n = A,T,C or G

<400> SEQUENCE: 11
gaattcgccc ttntggatgg cggcgttagt atcgaatcga cagcagtata gcgaccagca     60
ttcacatacg attgacgcat gatattactt tctgcgcact taacttcgca tctgggcaga   120
tgatgtcgag gcgaaaaaaa atataaatca cgctaacatt tgattaaaat agaacaacta   180
caatataaaa aaactataca aatgacaagt tcttgaaaac aagaatcttt ttattgtcag   240
tactgattag aaaaactcat cgagcatcaa atgaaactgc aatttattca tatcaggatt   300
atcaatacca tatttttgaa aaagccgttt ctgtaatgaa ggagaaaact caccgaggca   360
gttccatagg atggcaagat cctggtatcg gtctgcgatt ccgactcgtc aacatcaat    420 acaacctatt aatttcccct cgtcaaaaat aaggttatca agtgagaaat caccatgagt   480
gacgactgaa tccggtgaga atggcaaaag cttatgcatt tctttccaga cttgttcaac   540
aggccagcca ttacgctcgt catcaaaatc actcgcatca accaaaccgt tattcattcg   600
tgattgcgcc tgagcgagac gaaatacgcg atcgctgtta aaaggacaat tacaaacagg   660
aatcgaatgc aaccggcgca ggaacactgc cagcgcatca acaatatttt cacctgaatc   720
aggatattct tctaataccc ggaatgctgt tttgccgggg atcgcagtgg tgagtaacca   780
tgcatcatca ggagtacgga taaaatgctt gatggtcgga agaggcataa attccgtcag   840
ccagtttagt ctgaccatct catctgtaac atcattggca acgctacctt tgccatgttt   900
cagaaacaac tctggcgcat cgggcttccc atacaatcga tagattgtcg cacctgattg   960
cccgacatta tcgcgagccc atttataccc atataaatca gcatccatgt tggaatttaa  1020
tcgcggcctc gaaacgtgag tcttttcctt acccatggtt gtttatgttc ggatgtgatg  1080
tgagaactgt atcctagcaa gattttaaaa ggaagtatat gaaagaagaa cctcagtggc  1140
aaatcctaac cttttatatt tctctacagg gcgcgcgcgt ggggacaatt caacgcgtct  1200
gtgaggggag cgtttccctg ctcgcaggtc tgcagcgagg agccgtaatt tttgcttcgc  1260
gccgtgcggc catcaaaatg tatggatgca aatgattata catggggatg tatgggctaa  1320
atgtacgggc gacagtcaca tcatgcccct gagctgcgca cgtcaagact gtcaaggagg  1380
gtattctggg cctccatgtc gctggccggg tgacccggcg gggacgaggc aagctaaaca  1440
gatctgatct tgaaactgag taagatgctc agaatacccg tcaagataag agtataatgt  1500
```

-continued

```
agagtaatat accaagtatt cagcatattc tcctcttctt ttgtataaat cacggaaggg    1560
atgatttata agaaaaatga atactattac acttcattta ccaccctctg atctagattt    1620
tccaacgata tgtacgtagt ggtataaggt gagggggtcc acagatataa catcgtttaa    1680
tttagtacta acagagactt ttgtcacaac tacatataag tgtacaaata tagtacagat    1740
atgacacact tgtagcgcca acgcgcatcc tacggattgc tgacagaaaa aaaggtcacg    1800
tgaccagaaa agtcacgtgt aattttgtaa ctcaccgcat tctagcggtc cctgtcgtgc    1860
acactgcact caacaccata aaccttagca acctccaaag gaaatcaccg tataacaaag    1920 ccacagttt  acaacttagt ctcttatgaa gttacttacc aatgagaaat agaggctctt    1980
tctcgagaaa tatgaatatg gatatatata tatatatata tatatatata tatatatgta    2040
aacttggttc ttttttagct tgtgatctct agcttgggtc tctctctgtc gtaacagttg    2100
tgatatcgna agggcgaatt c                                              2121
```

<210> SEQ ID NO 12
<211> LENGTH: 1620
<212> TYPE: DNA
<213> ORGANISM: Artificial Sequence
<220> FEATURE:
<223> OTHER INFORMATION: PCR-amplified segment of leu2 gene of pAM178

<400> SEQUENCE: 12

```
tcgactacgt cgtaaggccg tttctgacag agtaaaattc ttgagggaac tttcaccatt      60
atgggaaatg cttcaagaag gtattgactt aaactccatc aaatggtcag gtcattgagt     120
gttttttatt tgttgtattt ttttttttttt agagaaaatc ctccaatatc aaattaggaa     180
tcgtagtttc atgattttct gttacaccta acttttgtg tggtgccctc ctccttgtca     240
atattaatgt taaagtgcaa ttcttttttcc ttatcacgtt gagccattag tatcaatttg     300
cttacctgta ttcctttact atcctccttt ttctccttct tgataaatgt atgtagattg     360
cgtatatagt ttcgtctacc ctatgaacat attccatttt gtaatttcgt gtcgtttcta     420
ttatgaattt catttataaa gtttatgtac aaatatcata aaaaaagaga atcttttta      480 gcaaggattt tcttaacttc ttcggcgaca gcatcaccga cttcggtggt actgttggaa     540
ccacctaaat caccagttct gatacctgca tccaaaacct ttttaactgc atcttcaatg     600
gccttacctt cttcaggcaa gttcaatgac aatttcaaca tcattgcagc agacaagata     660
gtggcgatag ggtcaacctt attctttggc aaatctggag cagaaccgtg gcatggttcg     720
tacaaaccaa atgcggtgtt cttgtctggc aaagaggcca aggacgcaga tgcaacaaa      780 cccaaggaac ctgggataac ggaggcttca tcggagatga tatcaccaaa catgttgctg     840 gtgattaaa  taccatttag gtgggttggg ttcttaacta ggatcatggc ggcagaatca     900
atcaattgat gttgaacctt caatgtaggg aattcgttct tgatggtttc ctccacagtt     960
tttctccata atcttgaaga ggccaaaaga ttagctttat ccaaggacca aataggcaat    1020
ggtggctcat gttgtagggc catgaaagcg gccattcttg tgattctttg cacttctgga    1080
acggtgtatt gttcactatc ccaagcgaca ccatcaccat cgtcttcctt tctcttacca    1140
aagtaaatac ctcccactaa ttctctgaca acaacgaagt cagtaccttt agcaaattgt    1200
ggcttgattg gagataagtc taaaagagag tcggatgcaa agttacatgg tcttaagttg    1260
gcgtacaatt gaagttcttt acggattttt agtaaacctt gttcaggtct aacactaccg    1320
gtaccccatt taggaccagc cacagcacct aacaaaacgg catcaacctt cttggaggct    1380
tccagcgcct catctggaag tggaacacct gtagcatcga tagcagcacc accaattaaa    1440
```

```
tgattttcga aatcgaactt gacattggaa cgaacatcag aaatagcttt aagaacctta    1500
atggcttcgg ctgtgatttc ttgaccaacg tggtcacctg gcaaaacgac gatcttctta    1560
ggggcagaca ttacaatggt atatccttga aatatatata gtgaaatacc gcacagatgc    1620
```

<210> SEQ ID NO 13
<211> LENGTH: 49
<212> TYPE: DNA
<213> ORGANISM: Artificial Sequence
<220> FEATURE:
<223> OTHER INFORMATION: Primer 4-49 mvaA SpeI

<400> SEQUENCE: 13

```
gctactagta ggaggaaaac atcatgcaaa gtttagataa gaatttccg                49
```

<210> SEQ ID NO 14
<211> LENGTH: 39
<212> TYPE: DNA
<213> ORGANISM: Artificial Sequence
<220> FEATURE:
<223> OTHER INFORMATION: Primer 4-49 mvaAR XbaI

<400> SEQUENCE: 14

```
gcttctagac tattgttgtc taatttcttg taaaatgcg                            39
```

<210> SEQ ID NO 15
<211> LENGTH: 55
<212> TYPE: DNA
<213> ORGANISM: Artificial Sequence
<220> FEATURE:
<223> OTHER INFORMATION: Primer HMGS 5 prime Sa mvaS-S

<400> SEQUENCE: 15

```
gaactgaaga tctaggagga aagcaaaatg acaataggta tcgacaaaat aaact          55
```

<210> SEQ ID NO 16
<211> LENGTH: 52
<212> TYPE: DNA
<213> ORGANISM: Artificial Sequence
<220> FEATURE:
<223> OTHER INFORMATION: Primer HMGS 3 prime Sa mvaS-AS

<400> SEQUENCE: 16

```
ttgcatgatg ttttcctcct actagttact ctggtctgtg atattcgcga ac             52
```

<210> SEQ ID NO 17
<211> LENGTH: 45
<212> TYPE: DNA
<213> ORGANISM: Artificial Sequence
<220> FEATURE:
<223> OTHER INFORMATION: Primer 67-1A-C

<400> SEQUENCE: 17

```
acactcgagg aggaataaat gagttttgat attgccaaat acccg                     45
```

<210> SEQ ID NO 18
<211> LENGTH: 37
<212> TYPE: DNA
<213> ORGANISM: Artificial Sequence
<220> FEATURE:
<223> OTHER INFORMATION: Primer 67-1B-C

<400> SEQUENCE: 18

```
tgatggtacc ttatgccagc caggccttga ttttggc                              37
```

<210> SEQ ID NO 19

```
<211> LENGTH: 45
<212> TYPE: DNA
<213> ORGANISM: Artificial Sequence
<220> FEATURE:
<223> OTHER INFORMATION: Primer 67-1C-C

<400> SEQUENCE: 19
actaggtacc aggaggaata aatgaagcaa ctcaccattc tgggc            45

<210> SEQ ID NO 20
<211> LENGTH: 37
<212> TYPE: DNA
<213> ORGANISM: Artificial Sequence
<220> FEATURE:
<223> OTHER INFORMATION: Primer 67-1D-C

<400> SEQUENCE: 20
aattgatggg ccctcagctt gcgagacgca tcacctc                     37

<210> SEQ ID NO 21
<211> LENGTH: 45
<212> TYPE: DNA
<213> ORGANISM: Artificial Sequence
<220> FEATURE:
<223> OTHER INFORMATION: Primer 67-1E-C

<400> SEQUENCE: 21
cataaagggc ccaggaggaa taaatggcaa ccactcattt ggatg            45

<210> SEQ ID NO 22
<211> LENGTH: 40
<212> TYPE: DNA
<213> ORGANISM: Artificial Sequence
<220> FEATURE:
<223> OTHER INFORMATION: Primer 67-1F-C

<400> SEQUENCE: 22
tattgttcat atgttatgta ttctcctgat ggatggttcg                  40

<210> SEQ ID NO 23
<211> LENGTH: 45
<212> TYPE: DNA
<213> ORGANISM: Artificial Sequence
<220> FEATURE:
<223> OTHER INFORMATION: Primer 67-1G-C

<400> SEQUENCE: 23
aactaacaca tatgaggagg aataaatgcg gacacagtgg ccctc            45

<210> SEQ ID NO 24
<211> LENGTH: 38
<212> TYPE: DNA
<213> ORGANISM: Artificial Sequence
<220> FEATURE:
<223> OTHER INFORMATION: Primer 67-1H-C

<400> SEQUENCE: 24
tgttagttac gcgtttaaag catggctctg tgcaatgg                    38

<210> SEQ ID NO 25
<211> LENGTH: 45
<212> TYPE: DNA
<213> ORGANISM: Artificial Sequence
<220> FEATURE:
<223> OTHER INFORMATION: Primer 67-2A-C

<400> SEQUENCE: 25
```

```
acgggatcca ggaggaataa atgcgaattg gacacggttt tgacg                    45
```

<210> SEQ ID NO 26
<211> LENGTH: 41
<212> TYPE: DNA
<213> ORGANISM: Artificial Sequence
<220> FEATURE:
<223> OTHER INFORMATION: Primer 67-2B-C

<400> SEQUENCE: 26

```
tttagttggg ccctcatttt gttgccttaa tgagtagcgc c                        41
```

<210> SEQ ID NO 27
<211> LENGTH: 49
<212> TYPE: DNA
<213> ORGANISM: Artificial Sequence
<220> FEATURE:
<223> OTHER INFORMATION: Primer 67-2C-C

<400> SEQUENCE: 27

```
tactaagggc ccaggaggaa ataatgcata accaggctcc aattcaacg                49
```

<210> SEQ ID NO 28
<211> LENGTH: 40
<212> TYPE: DNA
<213> ORGANISM: Artificial Sequence
<220> FEATURE:
<223> OTHER INFORMATION: Primer 67-2D-C

<400> SEQUENCE: 28

```
tccgggtacc ttattttca acctgctgaa cgtcaattcg                           40
```

<210> SEQ ID NO 29
<211> LENGTH: 43
<212> TYPE: DNA
<213> ORGANISM: Artificial Sequence
<220> FEATURE:
<223> OTHER INFORMATION: Primer 67-2E-C

<400> SEQUENCE: 29

```
aacaggtacc aggaggaaat aatgcagatc ctgttggcca acc                      43
```

<210> SEQ ID NO 30
<211> LENGTH: 45
<212> TYPE: DNA
<213> ORGANISM: Artificial Sequence
<220> FEATURE:
<223> OTHER INFORMATION: Primer 67-2F-C

<400> SEQUENCE: 30

```
tggatgaagt cgacttaatc gacttcacga atatcgacac gcagc                    45
```

<210> SEQ ID NO 31
<211> LENGTH: 50
<212> TYPE: DNA
<213> ORGANISM: Artificial Sequence
<220> FEATURE:
<223> OTHER INFORMATION: Primer 67-2G-C

<400> SEQUENCE: 31

```
catcaagtcg acaggaggaa ataatgcaaa cggaacacgt cattttattg               50
```

<210> SEQ ID NO 32
<211> LENGTH: 40
<212> TYPE: DNA
<213> ORGANISM: Artificial Sequence
<220> FEATURE:

<223> OTHER INFORMATION: Primer 67-2H-C

<400> SEQUENCE: 32
taatgcaagc ttatttaagc tgggtaaatg cagataatcg                                40

<210> SEQ ID NO 33
<211> LENGTH: 44
<212> TYPE: DNA
<213> ORGANISM: Artificial Sequence
<220> FEATURE:
<223> OTHER INFORMATION: Primer 67-2I-C

<400> SEQUENCE: 33
cagtaaagct taggaggaaa taatggactt tccgcagcaa ctcg                           44

<210> SEQ ID NO 34
<211> LENGTH: 41
<212> TYPE: DNA
<213> ORGANISM: Artificial Sequence
<220> FEATURE:
<223> OTHER INFORMATION: Primer 67-2J-C

<400> SEQUENCE: 34
tagttccatg gttatttatt acgctggatg atgtagtccg c                              41

<210> SEQ ID NO 35
<211> LENGTH: 35
<212> TYPE: DNA
<213> ORGANISM: Artificial Sequence
<220> FEATURE:
<223> OTHER INFORMATION: Primer 9-156A

<400> SEQUENCE: 35
acatagacgt cgggaaagcg aggatctagg taggg                                     35

<210> SEQ ID NO 36
<211> LENGTH: 37
<212> TYPE: DNA
<213> ORGANISM: Artificial Sequence
<220> FEATURE:
<223> OTHER INFORMATION: Primer 9-156B

<400> SEQUENCE: 36
ttcccgctcg aggtggcgga ccatataggc agatcag                                   37

<210> SEQ ID NO 37
<211> LENGTH: 30
<212> TYPE: DNA
<213> ORGANISM: Artificial Sequence
<220> FEATURE:
<223> OTHER INFORMATION: Primer 61-67-CPK001-G

<400> SEQUENCE: 37
gtttaaacta ctattagctg aattgccact                                           30

<210> SEQ ID NO 38
<211> LENGTH: 46
<212> TYPE: DNA
<213> ORGANISM: Artificial Sequence
<220> FEATURE:
<223> OTHER INFORMATION: Primer 61-67-CPK002-G

<400> SEQUENCE: 38
actgcaaagt acacatatat cccgggtgtc agctcttta gatcgg                          46

<210> SEQ ID NO 39

```
<211> LENGTH: 46
<212> TYPE: DNA
<213> ORGANISM: Artificial Sequence
<220> FEATURE:
<223> OTHER INFORMATION: Primer 61-67-CPK003-G

<400> SEQUENCE: 39
ccgatctaaa agagctgaca cccgggatat atgtgtactt tgcagt                      46

<210> SEQ ID NO 40
<211> LENGTH: 30
<212> TYPE: DNA
<213> ORGANISM: Artificial Sequence
<220> FEATURE:
<223> OTHER INFORMATION: Primer 61-67-CPK004-G

<400> SEQUENCE: 40
gtttaaacgg cgtcagtcca ccagctaaca                                        30

<210> SEQ ID NO 41
<211> LENGTH: 30
<212> TYPE: DNA
<213> ORGANISM: Artificial Sequence
<220> FEATURE:
<223> OTHER INFORMATION: Primer 61-67-CPK005-G

<400> SEQUENCE: 41
gtttaaactt gctaaattcg agtgaaacac                                        30

<210> SEQ ID NO 42
<211> LENGTH: 46
<212> TYPE: DNA
<213> ORGANISM: Artificial Sequence
<220> FEATURE:
<223> OTHER INFORMATION: Primer 61-67-CPK006-G

<400> SEQUENCE: 42
aaagatgaat tgaaaagctt cccgggtatg gaccctgaaa ccacag                      46

<210> SEQ ID NO 43
<211> LENGTH: 46
<212> TYPE: DNA
<213> ORGANISM: Artificial Sequence
<220> FEATURE:
<223> OTHER INFORMATION: Primer 61-67-CPK007-G

<400> SEQUENCE: 43
ctgtggtttc agggtccata cccgggaagc ttttcaattc atcttt                      46

<210> SEQ ID NO 44
<211> LENGTH: 30
<212> TYPE: DNA
<213> ORGANISM: Artificial Sequence
<220> FEATURE:
<223> OTHER INFORMATION: Primer 61-67-CPK008-G

<400> SEQUENCE: 44
gtttaaaccc aacaataata atgtcagatc                                        30

<210> SEQ ID NO 45
<211> LENGTH: 30
<212> TYPE: DNA
<213> ORGANISM: Artificial Sequence
<220> FEATURE:
<223> OTHER INFORMATION: Primer 61-67-CPK009-G

<400> SEQUENCE: 45
```

```
gtttaaacta ctcagtatat taagtttcga                                    30

<210> SEQ ID NO 46
<211> LENGTH: 70
<212> TYPE: DNA
<213> ORGANISM: Artificial Sequence
<220> FEATURE:
<223> OTHER INFORMATION: Primer 61-67-CPK010-G

<400> SEQUENCE: 46
atctctcgca agagtcagac tgactcccgg gcgtgaataa gcttcgggtg acccttatgg   60
cattcttttt                                                          70

<210> SEQ ID NO 47
<211> LENGTH: 70
<212> TYPE: DNA
<213> ORGANISM: Artificial Sequence
<220> FEATURE:
<223> OTHER INFORMATION: Primer 61-67-CPK011-G

<400> SEQUENCE: 47
aaaaagaatg ccataagggt cacccgaagc ttattcacgc ccgggagtca gtctgactct   60
tgcgagagat                                                          70

<210> SEQ ID NO 48
<211> LENGTH: 30
<212> TYPE: DNA
<213> ORGANISM: Artificial Sequence
<220> FEATURE:
<223> OTHER INFORMATION: Primer 61-67-CPK012-G

<400> SEQUENCE: 48
gtttaaacaa tttagtgtct gcgatgatga                                    30

<210> SEQ ID NO 49
<211> LENGTH: 30
<212> TYPE: DNA
<213> ORGANISM: Artificial Sequence
<220> FEATURE:
<223> OTHER INFORMATION: Primer 61-67-CPK013-G

<400> SEQUENCE: 49
gtttaaacta ttgtgagggt cagttatttc                                    30

<210> SEQ ID NO 50
<211> LENGTH: 44
<212> TYPE: DNA
<213> ORGANISM: Artificial Sequence
<220> FEATURE:
<223> OTHER INFORMATION: Primer 61-67-CPK014alt-G

<400> SEQUENCE: 50
gcggggacga ggcaagctaa actttagtat attcttcgaa gaaa                    44

<210> SEQ ID NO 51
<211> LENGTH: 44
<212> TYPE: DNA
<213> ORGANISM: Artificial Sequence
<220> FEATURE:
<223> OTHER INFORMATION: Primer 61-67-CPK015alt-G

<400> SEQUENCE: 51
tttcttcgaa gaatatacta aagtttagct tgcctcgtcc ccgc                    44

<210> SEQ ID NO 52
```

<211> LENGTH: 60
<212> TYPE: DNA
<213> ORGANISM: Artificial Sequence
<220> FEATURE:
<223> OTHER INFORMATION: Primer 61-67-CPK016-G

<400> SEQUENCE: 52
caatcaacgt ggagggtaat tctgctagcc tctcccgggt ggatggcggc gttagtatcg    60

<210> SEQ ID NO 53
<211> LENGTH: 60
<212> TYPE: DNA
<213> ORGANISM: Artificial Sequence
<220> FEATURE:
<223> OTHER INFORMATION: Primer 61-67-CPK017-G

<400> SEQUENCE: 53
cgatactaac gccgccatcc acccgggaga ggctagcaga attaccctcc acgttgattg    60

<210> SEQ ID NO 54
<211> LENGTH: 30
<212> TYPE: DNA
<213> ORGANISM: Artificial Sequence
<220> FEATURE:
<223> OTHER INFORMATION: Primer 61-67-CPK018-G

<400> SEQUENCE: 54
gtttaaacgc cgccgttgtt gttattgtag                                    30

<210> SEQ ID NO 55
<211> LENGTH: 30
<212> TYPE: DNA
<213> ORGANISM: Artificial Sequence
<220> FEATURE:
<223> OTHER INFORMATION: Primer 61-67-CPK019-G

<400> SEQUENCE: 55
gtttaaactt ttccaatagg tggttagcaa                                    30

<210> SEQ ID NO 56
<211> LENGTH: 55
<212> TYPE: DNA
<213> ORGANISM: Artificial Sequence
<220> FEATURE:
<223> OTHER INFORMATION: Primer 61-67-CPK020-G

<400> SEQUENCE: 56
gggtgacccg gcggggacga ggcaagctaa acgtcttcct ttctcttacc aaagt         55

<210> SEQ ID NO 57
<211> LENGTH: 55
<212> TYPE: DNA
<213> ORGANISM: Artificial Sequence
<220> FEATURE:
<223> OTHER INFORMATION: Primer 61-67-CPK021-G

<400> SEQUENCE: 57
actttggtaa gagaaaggaa gacgtttagc ttgcctcgtc cccgccgggt caccc         55

<210> SEQ ID NO 58
<211> LENGTH: 62
<212> TYPE: DNA
<213> ORGANISM: Artificial Sequence
<220> FEATURE:
<223> OTHER INFORMATION: Primer 61-67-CPK022-G

<400> SEQUENCE: 58

```
aatatcataa aaaaagagaa tctttcccgg gtggatggcg gcgttagtat cgaatcgaca    60
gc                                                                  62

<210> SEQ ID NO 59
<211> LENGTH: 62
<212> TYPE: DNA
<213> ORGANISM: Artificial Sequence
<220> FEATURE:
<223> OTHER INFORMATION: Primer 61-67-CPK023-G

<400> SEQUENCE: 59
gctgtcgatt cgatactaac gccgccatcc acccgggaaa gattctcttt ttttatgata    60
tt                                                                  62

<210> SEQ ID NO 60
<211> LENGTH: 45
<212> TYPE: DNA
<213> ORGANISM: Artificial Sequence
<220> FEATURE:
<223> OTHER INFORMATION: Primer 61-67-CPK024-G

<400> SEQUENCE: 60
gtttaaacgt gttaacgttt ctttcgccta cgtggaagga gaatc                    45

<210> SEQ ID NO 61
<211> LENGTH: 35
<212> TYPE: DNA
<213> ORGANISM: Artificial Sequence
<220> FEATURE:
<223> OTHER INFORMATION: Primer 61-67-CPK025-G

<400> SEQUENCE: 61 tcccccggg ttaaaaaaaa tccttggact agtca                                35

<210> SEQ ID NO 62
<211> LENGTH: 35
<212> TYPE: DNA
<213> ORGANISM: Artificial Sequence
<220> FEATURE:
<223> OTHER INFORMATION: Primer 61-67-CPK031-G

<400> SEQUENCE: 62 tcccccggg agttatgaca attacaacaa cagaa                                35

<210> SEQ ID NO 63
<211> LENGTH: 30
<212> TYPE: DNA
<213> ORGANISM: Artificial Sequence
<220> FEATURE:
<223> OTHER INFORMATION: Primer 61-67-CPK032-G

<400> SEQUENCE: 63 tcccccggg tatatatata tcattgttat                                      30

<210> SEQ ID NO 64
<211> LENGTH: 30
<212> TYPE: DNA
<213> ORGANISM: Artificial Sequence
<220> FEATURE:
<223> OTHER INFORMATION: Primer 61-67-CPK035-G

<400> SEQUENCE: 64 tcccccggg aaaagtaagt caaaaggcac                                      30

<210> SEQ ID NO 65
```

```
<211> LENGTH: 30
<212> TYPE: DNA
<213> ORGANISM: Artificial Sequence
<220> FEATURE:
<223> OTHER INFORMATION: Primer 61-67-CPK040-G

<400> SEQUENCE: 65 tcccccggg atggtctgct taaatttcat                                30

<210> SEQ ID NO 66
<211> LENGTH: 45
<212> TYPE: DNA
<213> ORGANISM: Artificial Sequence
<220> FEATURE:
<223> OTHER INFORMATION: Primer 61-67-CPK041-G

<400> SEQUENCE: 66 tcccccggg tagcttgtac ccattaaaag aattttatca tgccg               45

<210> SEQ ID NO 67
<211> LENGTH: 30
<212> TYPE: DNA
<213> ORGANISM: Artificial Sequence
<220> FEATURE:
<223> OTHER INFORMATION: Primer 61-67-CPK046-G

<400> SEQUENCE: 67 tcccccggg tttctcattc aagtggtaac                                30

<210> SEQ ID NO 68
<211> LENGTH: 30
<212> TYPE: DNA
<213> ORGANISM: Artificial Sequence
<220> FEATURE:
<223> OTHER INFORMATION: Primer 61-67-CPK047-G

<400> SEQUENCE: 68 tcccccggg taaataaaga aaataaagtt                                30

<210> SEQ ID NO 69
<211> LENGTH: 47
<212> TYPE: DNA
<213> ORGANISM: Artificial Sequence
<220> FEATURE:
<223> OTHER INFORMATION: Primer 61-67-CPK050-G

<400> SEQUENCE: 69 aattttttgaa aattcaatat aaatggcttc agaaaaagaa attagga           47

<210> SEQ ID NO 70
<211> LENGTH: 47
<212> TYPE: DNA
<213> ORGANISM: Artificial Sequence
<220> FEATURE:
<223> OTHER INFORMATION: Primer 61-67-CPK051-G

<400> SEQUENCE: 70
tcctaatttc tttttctgaa gccatttata ttgaattttc aaaaatt            47

<210> SEQ ID NO 71
<211> LENGTH: 51
<212> TYPE: DNA
<213> ORGANISM: Artificial Sequence
<220> FEATURE:
<223> OTHER INFORMATION: Primer 61-67-CPK052-G

<400> SEQUENCE: 71
```
agttttcacc aattggtctg cagccattat agttttttct ccttgacgtt a     51

<210> SEQ ID NO 72
<211> LENGTH: 51
<212> TYPE: DNA
<213> ORGANISM: Artificial Sequence
<220> FEATURE:
<223> OTHER INFORMATION: Primer 61-67-CPK053-G

<400> SEQUENCE: 72
taacgtcaag gagaaaaaac tataatggct gcagaccaat tggtgaaaac t     51

<210> SEQ ID NO 73
<211> LENGTH: 47
<212> TYPE: DNA
<213> ORGANISM: Artificial Sequence
<220> FEATURE:
<223> OTHER INFORMATION: Primer 61-67-CPK054-G

<400> SEQUENCE: 73 aattttttgaa aattcaatat aaatgaaact ctcaactaaa ctttgtt     47

<210> SEQ ID NO 74
<211> LENGTH: 47
<212> TYPE: DNA
<213> ORGANISM: Artificial Sequence
<220> FEATURE:
<223> OTHER INFORMATION: Primer 61-67-CPK055-G

<400> SEQUENCE: 74
aacaaagttt agttgagagt ttcatttata ttgaattttc aaaaatt     47

<210> SEQ ID NO 75
<211> LENGTH: 47
<212> TYPE: DNA
<213> ORGANISM: Artificial Sequence
<220> FEATURE:
<223> OTHER INFORMATION: Primer 61-67-CPK056-G

<400> SEQUENCE: 75 aattttttgaa aattcaatat aaatgtctca gaacgtttac attgtat     47

<210> SEQ ID NO 76
<211> LENGTH: 47
<212> TYPE: DNA
<213> ORGANISM: Artificial Sequence
<220> FEATURE:
<223> OTHER INFORMATION: Primer 61-67-CPK057-G

<400> SEQUENCE: 76
atacaatgta aacgttctga gacatttata ttgaattttc aaaaatt     47

<210> SEQ ID NO 77
<211> LENGTH: 51
<212> TYPE: DNA
<213> ORGANISM: Artificial Sequence
<220> FEATURE:
<223> OTHER INFORMATION: Primer 61-67-CPK058-G

<400> SEQUENCE: 77
tgcagaagtt aagaacggta atgacattat agttttttct ccttgacgtt a     51

<210> SEQ ID NO 78
<211> LENGTH: 51
<212> TYPE: DNA
<213> ORGANISM: Artificial Sequence
<220> FEATURE:

<223> OTHER INFORMATION: Primer 61-67-CPK059-G

<400> SEQUENCE: 78
taacgtcaag gagaaaaaac tataatgtca ttaccgttct taacttctgc a    51

<210> SEQ ID NO 79
<211> LENGTH: 47
<212> TYPE: DNA
<213> ORGANISM: Artificial Sequence
<220> FEATURE:
<223> OTHER INFORMATION: Primer 61-67-CPK060-G

<400> SEQUENCE: 79
aatttttgaa aattcaatat aaatgtcaga gttgagagcc ttcagtg    47

<210> SEQ ID NO 80
<211> LENGTH: 47
<212> TYPE: DNA
<213> ORGANISM: Artificial Sequence
<220> FEATURE:
<223> OTHER INFORMATION: Primer 61-67-CPK061-G

<400> SEQUENCE: 80
cactgaaggc tctcaactct gacatttata ttgaattttc aaaaatt    47

<210> SEQ ID NO 81
<211> LENGTH: 51
<212> TYPE: DNA
<213> ORGANISM: Artificial Sequence
<220> FEATURE:
<223> OTHER INFORMATION: Primer 61-67-CPK062-G

<400> SEQUENCE: 81
ggtaacggat gctgtgtaaa cggtcattat agttttttct ccttgacgtt a    51

<210> SEQ ID NO 82
<211> LENGTH: 51
<212> TYPE: DNA
<213> ORGANISM: Artificial Sequence
<220> FEATURE:
<223> OTHER INFORMATION: Primer 61-67-CPK063-G

<400> SEQUENCE: 82
taacgtcaag gagaaaaaac tataatgacc gtttacacag catccgttac c    51

<210> SEQ ID NO 83
<211> LENGTH: 47
<212> TYPE: DNA
<213> ORGANISM: Artificial Sequence
<220> FEATURE:
<223> OTHER INFORMATION: Primer 61-67-CPK064-G

<400> SEQUENCE: 83
aatttttgaa aattcaatat aaatgactgc cgacaacaat agtatgc    47

<210> SEQ ID NO 84
<211> LENGTH: 47
<212> TYPE: DNA
<213> ORGANISM: Artificial Sequence
<220> FEATURE:
<223> OTHER INFORMATION: Primer 61-67-CPK065-G

<400> SEQUENCE: 84
gcatactatt gttgtcggca gtcatttata ttgaattttc aaaaatt    47

<210> SEQ ID NO 85

```
<211> LENGTH: 70
<212> TYPE: DNA
<213> ORGANISM: Artificial Sequence
<220> FEATURE:
<223> OTHER INFORMATION: Primer 61-67-CPK066-G

<400> SEQUENCE: 85
ggtaagacgg ttgggtttta tcttttgcag ttggtactat taagaacaat cacaggaaac    60
agctatgacc                                                           70

<210> SEQ ID NO 86
<211> LENGTH: 70
<212> TYPE: DNA
<213> ORGANISM: Artificial Sequence
<220> FEATURE:
<223> OTHER INFORMATION: Primer 61-67-CPK067-G

<400> SEQUENCE: 86
ttgcgttttg tactttggtt cgctcaattt tgcaggtaga taatcgaaaa gttgtaaaac    60
gacggccagt                                                           70

<210> SEQ ID NO 87
<211> LENGTH: 66
<212> TYPE: DNA
<213> ORGANISM: Artificial Sequence
<220> FEATURE:
<223> OTHER INFORMATION: Primer 50-56-pw100-G

<400> SEQUENCE: 87
gagtgaacct gctgcctggc gtgctctgac tcagtacatt tcatagtgga tggcggcgtt    60
agtatc                                                               66

<210> SEQ ID NO 88
<211> LENGTH: 65
<212> TYPE: DNA
<213> ORGANISM: Artificial Sequence
<220> FEATURE:
<223> OTHER INFORMATION: Primer 50-56-pw101-G

<400> SEQUENCE: 88
cgtgtatacg ttttccgctt ctgctcttcg tcttttctct tcttccgata tcacaactgt    60
tacga                                                                65

<210> SEQ ID NO 89
<211> LENGTH: 21
<212> TYPE: DNA
<213> ORGANISM: Artificial Sequence
<220> FEATURE:
<223> OTHER INFORMATION: Primer PW-91-079-CPK373-G

<400> SEQUENCE: 89
tcgactacgt cgtaaggccg t                                              21

<210> SEQ ID NO 90
<211> LENGTH: 42
<212> TYPE: DNA
<213> ORGANISM: Artificial Sequence
<220> FEATURE:
<223> OTHER INFORMATION: Primer PW-91-079-CPK374-G

<400> SEQUENCE: 90
gcatctgtgc ggtatttcac tatatatatt tcaaggatat ac                       42

<210> SEQ ID NO 91
```

```
<211> LENGTH: 25
<212> TYPE: DNA
<213> ORGANISM: Artificial Sequence
<220> FEATURE:
<223> OTHER INFORMATION: Primer PW-91-079-CPK376-G

<400> SEQUENCE: 91
tatggtgcac tctcagtaca atctg                                    25

<210> SEQ ID NO 92
<211> LENGTH: 42
<212> TYPE: DNA
<213> ORGANISM: Artificial Sequence
<220> FEATURE:
<223> OTHER INFORMATION: Primer PW-91-079-CPK375-G

<400> SEQUENCE: 92
gtatatcctt gaaatatata tagtgaaata ccgcacagat gc                 42
```

JET FUEL COMPOSITIONS AND METHODS OF MAKING AND USING SAME

PRIOR RELATED APPLICATIONS

This application claims the benefit under 35 U.S.C. §119(e) of U.S. Provisional Patent Application Nos. 60/860,853, filed Nov. 21, 2006, and 60/951,236, filed Jul. 23, 2007, all of which are incorporated herein by reference in their entireties.

FIELD OF THE INVENTION

Provided herein are, among other things, jet fuel compositions and methods of making and using the same. In some embodiments, the fuel compositions comprise at least a fuel component readily and efficiently produced, at least in part, from a microorganism. In certain embodiments, the fuel compositions provided herein comprise a high concentration of at least a bioengineered fuel component. In further embodiments, the fuel compositions provided herein comprise limonane.

BACKGROUND OF THE INVENTION

Biofuel is generally a fuel derived from biomass, i.e., recently living organisms or their metabolic byproducts, such as manure from animals. Biofuel is desirable because it is a renewable energy source, unlike other natural resources such as petroleum, coal and nuclear fuels. A biofuel that is suitable for use as jet fuel has yet to be introduced. Therefore, there is a need for biofuels for jet engines. The present invention provides such biofuels.

SUMMARY OF THE INVENTION

Provided herein are, among other things, fuel compositions comprising limonane and methods of making and using the same. In some embodiments, the fuel compositions further comprises an aromatic compound. In other embodiments, the aromatic compound is an isoprenoid. In still other embodiments, the aromatic compound is p-cymene. In certain embodiments, the fuel composition comprises a fuel component readily and efficiently produced, at least in part, from a microorganism.

In one aspect, provided herein are fuel compositions comprising (a) limonane in an amount that is at least 2% by volume, based on the total volume of the fuel composition; and (b) a petroleum-based fuel in an amount that is at least 5% by volume, based on the total volume of the fuel composition, wherein the fuel composition has a flash point equal to or greater than 38° C. In some embodiments, the fuel compositions disclosed herein further comprise p-cymene.

In another aspect, provided herein are fuel compositions comprising (a) limonane in an amount that is at least 40% by volume, based on the total volume of the fuel composition; (b) p-cymene in an amount that is from about 1% to about 10% by volume, based on the total volume of the fuel composition; and (b) a petroleum-based fuel in an amount that is at least 40% by volume, based on the total volume of the fuel composition, wherein the fuel composition has a density from about 750 kg/m³ to about 840 kg/m³ at 15° C., a flash point equal to or greater than 38° C.; and a freezing point lower than −40° C.

In another aspect, provided herein are methods of making a fuel composition comprising the steps of (a) contacting an isoprenoid starting material with hydrogen in the presence of a catalyst to form a limonane; and (b) mixing the limonane with a fuel component to make the fuel composition. In some embodiments, the isoprenoid starting material is limonene, β-phellandrene, γ-terpinene, terpinolene or a combination thereof.

In another aspect, provided herein are methods of making a fuel composition from a simple sugar comprising the steps of (a) contacting a cell capable of making an isoprenoid starting material with the simple sugar under conditions suitable for making the isoprenoid starting material; (b) converting the isoprenoid starting material to limonane; and (c) mixing the limonane with a fuel component to make the fuel composition. In certain embodiments, the isoprenoid starting material is limonene, β-phellandrene, γ-terpinene, terpinolene or a combination thereof.

In another aspect, provided herein are vehicles comprising an internal combustion engine; a fuel tank connected to the internal combustion engine; and a fuel composition disclosed herein in the fuel tank, wherein the fuel composition is used to power the internal combustion engine. In some embodiments, the internal combustion engine is a jet engine.

In another aspect, provided herein are methods of powering an engine comprising the step of combusting one or more of the fuel compositions disclosed herein. In certain embodiments, the engine is a jet engine.

In some embodiments, the limonane in the fuel compositions disclosed herein is or comprises

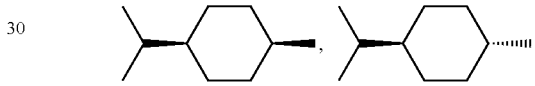

or a combination thereof.

In certain embodiments, the petroleum-based fuel in the fuel compositions disclosed herein is kerosene, Jet A, Jet A-1, Jet B, or a combination thereof. In other embodiments, the fuel compositions disclosed herein meet the ASTM D 1655 specification for Jet A, Jet A-1 or Jet B.

DESCRIPTION OF THE DRAWINGS

FIG. 8 shows the ASTM D 1655 test data for certain embodiments of the fuel compositions disclosed herein.

DEFINITIONS

Figure 1:
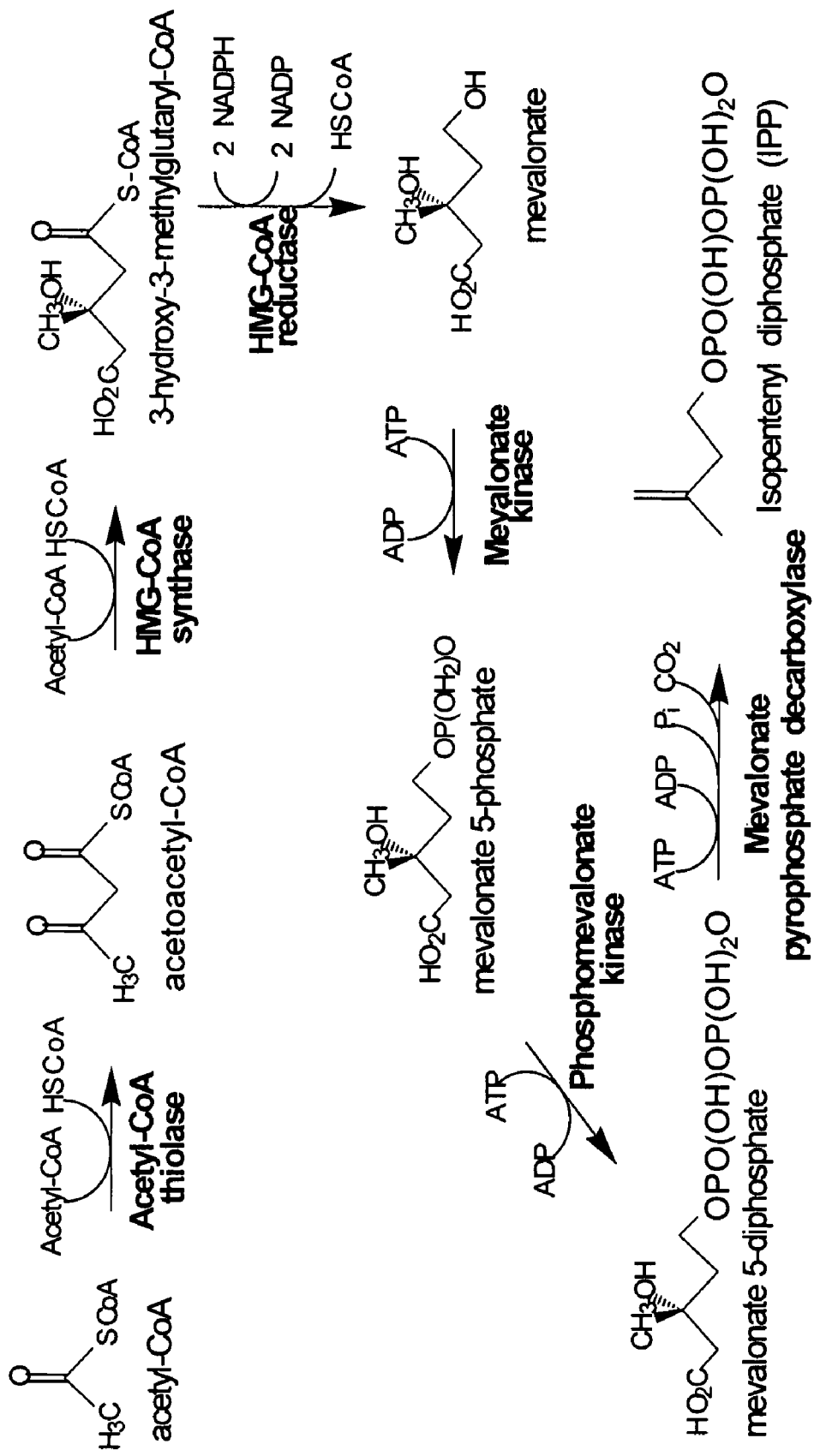
FIG. 1 is a schematic representation of the mevalonate ("MEV") pathway for the production of isopentenyl pyrophosphate ("IPP").

The ASTM D 1655 specifications, published by ASTM International, set certain minimum acceptance requirements for Jet A, Jet A-1, and Jet B.

"Bioengineered compound" refers to a compound made by a host cell, including any archae, bacterial, or eukaryotic cells or microorganism.

"Biofuel" refers to any fuel that is derived from a biomass, i.e., recently living organisms or their metabolic byproducts, such as manure from cows. It is a renewable energy source, unlike other natural resources such as petroleum, coal and nuclear fuels.

"Density" refers to a measure of mass per volume at a particular temperature. The generally accepted method for measuring the density of a fuel is ASTM Standard D 4052, which is incorporated herein by reference.

"Doctor Test" is for the detection of mercaptans in petroleum-based fuels such as jet fuel and kerosene. This test may also provide information on hydrogen sulfide and elemental sulfur that may be present in the fuels. The generally accepted method for measuring the freezing point of a fuel is ASTM Standard D 4952, which is incorporated herein by reference.

"Flash point" refers to the lowest temperature at which the vapors above a flammable liquid will ignite in the air on the application of an ignition source. Generally, every flammable liquid has a vapor pressure, which is a function of the temperature of the liquid. As the temperature increases, the vapor pressure of the liquid increases. As the vapor pressure increases, the concentration of the evaporated liquid in the air increases. At the flash point temperature, just enough amount of the liquid has vaporized to bring the vapor-air space over the liquid above the lower flammability limit. For example, the flash point of gasoline is about −43° C. which is why gasoline is so highly flammable. For safety reasons, it is desirable to have much higher flash points for fuel that is contemplated for use in jet engines. The generally accepted methods for measuring the flash point of a fuel are ASTM Standard D 56, ASTM Standard D 93, ASTM Standard D 3828-98, all of which are incorporated herein by reference.

"Freezing point" refers to the temperature at which the last wax crystal melts, when warming a fuel that has been previously been cooled until waxy crystals form. The generally accepted method for measuring the freezing point of a fuel is ASTM Standard D 2386, which is incorporated herein by reference.

"Fuel" refers to one or more hydrocarbons, one or more alcohols, one or more fatty esters or a mixture thereof. Preferably, liquid hydrocarbons are used. Fuel can be used to power internal combustion engines such as reciprocating engines (e.g., gasoline engines and diesel engines), Wankel engines, jet engines, some rocket engines, missile engines and gas turbine engines. In some embodiments, fuel typically comprises a mixture of hydrocarbons such as alkanes, cycloalkanes and aromatic hydrocarbons. In other embodiments, fuel comprises limonane.

"Fuel additive" refers to chemical components added to fuels to alter the properties of the fuel, e.g., to improve engine performance, fuel handling, fuel stability, or for contaminant control. Types of additives include, but are not limited to, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof. The term "conventional additives" refers to fuel additives known to skilled artisan, such as those described above, and does not include limonane.

"Fuel component" refers to any compound or a mixture of compounds that are used to formulate a fuel composition. There are "major fuel components" and "minor fuel components." A major fuel component is present in a fuel composition by at least 50% by volume; and a minor fuel component is present in a fuel composition by less than 50%. Fuel additives are minor fuel components. Limonane can be a major component or a minor component, or in a mixture with other fuel components.

"Fuel composition" refers to a fuel that comprises at least two fuel components.

"Isoprenoid" and "isoprenoid compound" are used interchangeably herein and refer to a compound derivable from isopentenyl diphosphate.

"Isoprenoid starting material" refers to an isoprenoid compound from which limonane can be made.

"Jet fuel" refers to a fuel suitable for use in a jet engine.

"Kerosene" refers to a specific fractional distillate of petroleum (also known as "crude oil"), generally between about 150° C. and about 275° C. at atmospheric pressure. Crude oils are composed primarily of hydrocarbons of the parffinic, naphthenic, and aromatic classes.

"Limonane" refers to the following compound

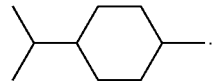

"Missile fuel" refers to a fuel suitable for use in a missile engine.

"p-Cymene" refers to the following compound

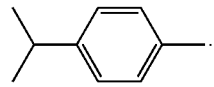

"Petroleum-based fuel" refers to a fuel that includes a fractional distillate of petroleum.

"Smoke Point" refers to the point in which a fuel or fuel composition is heated until it breaks down and smokes. The generally accepted method for measuring the smoke point of a fuel is ASTM Standard D 1322, which is incorporated herein by reference.

"Viscosity" refers to a measure of the resistance of a fuel or fuel composition to deform under shear stress. The generally accepted method for measuring the viscosity of a fuel is ASTM Standard D 445, which is incorporated herein by reference.

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

As used herein, a composition that is "substantially free" of a compound means that the composition contains less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the compound, based on the total volume of the composition.

As used herein, the term "stereochemically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, the term "enantiomerically pure" means a stereomerically pure composition of a compound having one chiral center.

As used herein, the term "racemic" or "racemate" means about 50% of one enantiomer and about 50% of the corresponding enantiomer relative to all chiral centers in the molecule. The invention encompasses all enantiomerically pure, enantiomerically enriched, diastereomerically pure, diastereomerically enriched, and racemic mixtures of the compounds of the invention.

In addition to the definitions above, certain compounds described herein have one or more double bonds that can exist as either the Z or E isomer. In certain embodiments, compounds described herein are present as individual isomers substantially free of other isomers and alternatively, as mixtures of various isomers, e.g., racemic mixtures of stereoisomers.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

DESCRIPTION OF EMBODIMENTS OF THE INVENTION

In one aspect, the invention provides a fuel composition comprising:

(a) limonane in an amount that is at least 2% by volume, based on the total volume of the fuel composition; and (b) a petroleum-based fuel in an amount that is at least 5% by volume, based on the total volume of the fuel composition, wherein the fuel composition has a flash point equal to or greater than 38° C.

In certain embodiments, the amount of limonane is from about 2% to about 95%, from about 2% to about 90%, from about 2% to about 80%, from about 2% to about 70% or from about 2% to about 50% by weight or volume, based on the total weight or volume of the fuel composition. In certain embodiments, the amount of limonane is at least about 3%, 5%, 10%, 15%, 20%, 25%, 30%, 35%, 40%, 45%, 50%, 55%, 60%, 65%, 70%, 75%, 80%, 85%, 90% or 95% by weight or volume, based on the total weight or volume of the fuel composition. In certain embodiments, the amount is in weight % based on the total weight of the fuel composition. In other embodiments, the amount is in volume % based on the total volume of the fuel composition.

In other embodiments, limonane is present in an amount of at most about 5%, at most about 10%, at most about 15%, at most about 20%, at most about 25%, at most about 30%, at most about 35%, at most about 40%, at most about 45%, at most about 50%, at most about 60%, at most about 70%, at most about 80%, or at most about 90%, based on the total weight or volume of the fuel composition. In further embodiments, limonane is present in an amount from about 2% to about 99%, from about 2.5% to about 95%, from about 5% to about 90%, from about 7.5% to about 85%, from about 10% to about 80%, from about 15% to about 80%, from about 20% to about 75%, or from about 25% to about 75%, based on the total weight or volume of the fuel composition.

In some embodiments, the limonane in the fuel compositions disclosed herein is or comprises

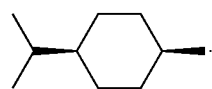

In other embodiments, the limonane in the fuel compositions disclosed herein is or comprises

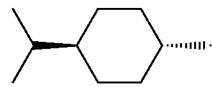

In still other embodiments, the limonane in the fuel compositions disclosed herein is or comprises a mixture comprising:

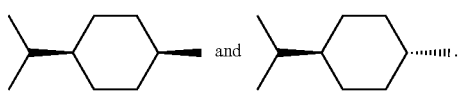

In some embodiments, limonane is derived from an isoprenoid starting material. In certain embodiments, the isoprenoid starting material is made by host cells by converting a carbon source into the isoprenoid starting material.

In other embodiments, the carbon source is a sugar such as a monosaccharide (simple sugar), a disaccharide, or one or more combinations thereof. In certain embodiments, the sugar is a simple sugar capable of supporting the growth of one or more of the cells provided herein. The simple sugar can be any simple sugar known to those of skill in the art. Some non-limiting examples of suitable simple sugars or monosaccharides include glucose, galactose, mannose, fructose, ribose, and combinations thereof. Some non-limiting examples of suitable disaccharides include sucrose, lactose, maltose, trehalose, cellobiose, and combinations thereof.

In other embodiments, the carbon source is a polysaccharide. Some non-limiting examples of suitable polysaccharides include starch, glycogen, cellulose, chitin, and combinations thereof.

In still other embodiments, the carbon source is a non-fermentable carbon source. Some non-limiting examples of suitable non-fermentable carbon source include acetate and glycerol.

In some embodiments, the amount of the petroleum-based fuel in the fuel composition disclosed herein may be from about 5% to about 90%, from about 5% to about 85%, from about 5% to about 80%, from about 5% to about 70%, from about 5% to about 60%, or from about 5% to about 50%, based on the total amount of the fuel composition. In certain embodiments, the amount of the petroleum-based fuel is less than about 95%, less than about 90%, less than about 85%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, based on the total amount of the fuel composition. In other embodiments, the petroleum based fuel is at least about 20%, at least about 30%, at least about 40%, at least about 50%, at least about 60%, at least about 70%, at least about 80% based on the total amount of the fuel composition. In some embodiments, the amount is in wt. % based on the total weight of the fuel composition. In other embodiments, the amount is in vol. % based on the total volume of the fuel composition.

In some embodiments, the petroleum-based fuel is kerosene. Conventional kerosene generally is a mixture of hydrocarbons, having a boiling point from about 285° F. to about 610° F. (i.e., from about 140° C. to about 320° C.).

In other embodiments, the petroleum-based fuel is a jet fuel. Any jet fuel known to skilled artisans can be used herein. The American Society for Testing and Materials ("ASTM") and the United Kingdom Ministry of Defense ("MOD") have taken the lead roles in setting and maintaining specification for civilian aviation turbine fuel or jet fuel. The respective specifications issued by these two organizations are very similar but not identical. Many other countries issue their own national specifications for jet fuel but are very nearly or completely identical to either the ASTM or MOD specification. ASTM D 1655 is the Standard Specification for Aviation Turbine Fuels and includes specifications for Jet A, Jet A-1 and Jet B fuels. Defence Standard 91-91 is the MOD specification for Jet A-1.

Jet A-1 is the most common jet fuel and is produced to an internationally standardized set of specifications. In the United States only, a version of Jet A-1 known as Jet A is also used. Another jet fuel that is commonly used in civilian aviation is called Jet B. Jet B is a lighter fuel in the naphtha-kerosene region that is used for its enhanced cold-weather performance. Jet A, Jet A-1 and Jet B are specified in ASTM Specification D 1655.

Alternatively, jet fuels are classified by militaries around the world with a different system of JP numbers. Some are almost identical to their civilian counterparts and differ only by the amounts of a few additives. For example, Jet A-1 is similar to JP-8 and Jet B is similar to JP-4.

In some embodiments, the fuel compositions provided herein further comprise an aromatic compound such as p-cymene, m-cymene or o-cymene. In further embodiments, the aromatic compound is or comprises p-cymene. In certain embodiments, the amount of p-cymene is from about 0.1% to about 50% by volume, from about 0.1% to about 45% by volume, from about 0.1% to about 40% by volume, or from about 0.1% to about 35% by volume, based on the total volume of the fuel composition. In other embodiments, the amount of p-cymene is from about 0.5% to about 35% by volume, based on the total volume of the fuel composition. In still other embodiments, the amount of p-cymene is from about 1% to about 25%, from about 5% to about 25%, from about 5% to about 20%, or 10% to about 20% by volume, based on the total volume of the fuel composition.

In some embodiments, the total amount of aromatic compounds in the fuel compositions is from about 1% to about 50% by weight or volume, based on the total weight or volume of the fuel composition. In other embodiments, the total amount of aromatic compounds in the fuel compositions is from about 15% to about 35% by weight or volume, based on the total weight or volume of the fuel compositions. In further embodiments, the total amount of aromatic compounds in the fuel compositions is from about 15% to about 25% by weight or volume, based on the total weight or volume of the fuel compositions. In other embodiments, the total amount of aromatic compounds in the fuel compositions is from about 5% to about 10% by weight or volume, based on the total weight or volume of the fuel composition. In still further embodiments, the total amount of aromatic compounds in the fuel compositions is less than about 25% by weight or volume, based on the total weight or volume of the fuel compositions.

In some embodiments, the fuel composition further comprises a fuel additive. In certain embodiments, the fuel additive is from about 0.1% to about 50% by weight or volume, based on the total weight or volume of the fuel composition. The fuel additive can be any fuel additive known to those of skill in the art. In further embodiments, the fuel additive is selected from the group consisting of oxygenates, antioxidants, thermal stability improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, de-emulsifiers, dyes, markers, static dissipaters, biocides and combinations thereof.

The amount of a fuel additive in the fuel composition disclosed herein may be from about 0.1% to less than about 50%, from about 0.2% to about 40%, from about 0.3% to about 30%, from about 0.4% to about 20%, from about 0.5% to about 15% or from about 0.5% to about 10%, based on the total amount of the fuel composition. In certain embodiments, the amount of a fuel additive is less than about 50%, less than about 45%, less than about 40%, less than about 35%, less than about 30%, less than about 25%, less than about 20%, less than about 15%, less than about 10%, less than about 5%, less than about 4%, less than about 3%, less than about 2%, less than about 1% or less than about 0.5%, based on the total amount of the fuel composition. In some embodiments, the amount is in wt. % based on the total weight of the fuel composition. In other embodiments, the amount is in vol. % based on the total volume of the fuel composition.

Illustrative examples of fuel additives are described in greater detail below. Lubricity improvers are one example. In certain additives, the concentration of the lubricity improver in the fuel falls in the range from about 1 ppm to about 50,000 ppm, preferably from about 10 ppm to about 20,000 ppm, and more preferably from about 25 ppm to about 10,000 ppm. Some non-limiting examples of lubricity improver include esters of fatty acids.

Stabilizers improve the storage stability of the fuel composition. Some non-limiting examples of stabilizers include tertiary alkyl primary amines. The stabilizer may be present in the fuel composition at a concentration from about 0.001 wt. % to about 2 wt. %, based on the total weight of the fuel composition, and in one embodiment from about 0.01 wt. % to about 1 wt. %.

Combustion improvers increase the mass burning rate of the fuel composition. Some non-limiting examples of combustion improvers include ferrocene(dicyclopentadienyl iron), iron-based combustion improvers (e.g., TURBOTECT™ ER-18 from Turbotect (USA) Inc., Tomball, Tex.), barium-based combustion improvers, cerium-based combustion improvers, and iron and magnesium-based combustion improvers (e.g., TURBOTECT™ 703 from Turbotect (USA) Inc., Tomball, Tex.). The combustion improver may be present in the fuel composition at a concentration from about 0.001 wt. % to about 1 wt. %, based on the total weight of the fuel composition, and in one embodiment from about 0.01 wt. % to about 1 wt. %.

Antioxidants prevent the formation of gum depositions on fuel system components caused by oxidation of fuels in storage and/or inhibit the formation of peroxide compounds in certain fuel compositions can be used herein. The antioxidant may be present in the fuel composition at a concentration from about 0.001 wt. % to about 5 wt. %, based on the total weight of the fuel composition, and in one embodiment from about 0.01 wt. % to about 1 wt. %.

Static dissipaters reduce the effects of static electricity generated by movement of fuel through high flow-rate fuel transfer systems. The static dissipater may be present in the fuel composition at a concentration from about 0.001 wt. % to about 5 wt. %, based on the total weight of the fuel composition, and in one embodiment from about 0.01 wt. % to about 1 wt. %.

Corrosion inhibitors protect ferrous metals in fuel handling systems such as pipelines, and fuel storage tanks, from corrosion. In circumstances where additional lubricity is desired, corrosion inhibitors that also improve the lubricating properties of the composition can be used. The corrosion inhibitor may be present in the fuel composition at a concentration from about 0.001 wt. % to about 5 wt. %, based on the total weight of the fuel composition, and in one embodiment from about 0.01 wt. % to about 1 wt. %.

Fuel system icing inhibitors (also referred to as anti-icing additive) reduce the freezing point of water precipitated from jet fuels due to cooling at high altitudes and prevent the formation of ice crystals which restrict the flow of fuel to the engine. Certain fuel system icing inhibitors can also act as a biocide. The fuel system icing inhibitor may be present in the fuel composition at a concentration from about 0.001 wt. % to about 5 wt. %, based on the total weight of the fuel composition, and in one embodiment from about 0.01 wt. % to about 1 wt. %.

Biocides are used to combat microbial growth in the fuel composition. The biocide may be present in the fuel composition at a concentration from about 0.001 wt. % to about 5 wt. %, based on the total weight of the fuel composition, and in one embodiment from about 0.01 wt. % to about 1 wt. %.

Metal deactivators suppress the catalytic effect of some metals, particularly copper, have on fuel oxidation. The metal deactivator may be present in the fuel composition at a concentration from about 0.001 wt. % to about 5 wt. %, based on the total weight of the fuel composition, and in one embodiment from about 0.01 wt. % to about 1 wt. %.

Thermal stability improvers are use to inhibit deposit formation in the high temperature areas of the aircraft fuel system. The thermal stability improver may be present in the fuel composition at a concentration from about 0.001 wt. % to about 5 wt. %, based on the total weight of the fuel composition, and in one embodiment from about 0.01 wt. % to about 1 wt. %.

In some embodiments, the fuel composition has a flash point greater than about 32° C., greater than about 33° C., greater than about 34° C., greater than about 35° C., greater than about 36° C., greater than about 37° C., greater than about 38° C., greater than about 39° C., greater than about 40° C., greater than about 41° C., greater than about 42° C., greater than about 43° C., or greater than about 44° C. In other embodiments, the fuel composition has a flash point greater than 38° C. In certain embodiments, the flash point of the fuel composition disclosed herein is measured according to ASTM Standard D 56. In other embodiments, the flash point of the fuel composition disclosed herein is measured according to ASTM Standard D 93. In further embodiments, the flash point of the fuel composition disclosed herein is measured according to ASTM Standard D 3828-98. In still further embodiments, the flash point of the fuel composition disclosed herein is measured according to any conventional method known to a skilled artisan for measuring flash point of fuels.

In some embodiments, the fuel composition has a density at 15° C. from about 750 kg/m$^3$ to about 850 kg/m$^3$, from about 750 kg/m$^3$ to about 845 kg/m$^3$, from about 750 kg/m$^3$ to about 840 kg/m$^3$, from about 760 kg/m$^3$ to about 845 kg/m$^3$, from about 770 kg/m$^3$ to about 850 kg/m$^3$, from about 770 kg/m$^3$ to about 845 kg/m$^3$, from about 775 kg/m$^3$ to about 850 kg/m$^3$, or from about 775 kg/m$^3$ to about 845 kg/m$^3$. In other embodiments, the fuel composition has a density at 15° C. from about 780 kg/m$^3$ to about 845 kg/m$^3$. In still other embodiments, the fuel composition has a density at 15° C. from about 775 kg/m$^3$ to about 840 kg/m$^3$. In still other embodiments, the fuel composition has a density at 15° C. from about 750 kg/m$^3$ to about 805 kg/m$^3$. In certain embodiments, the density of the fuel composition disclosed herein is measured according to ASTM Standard D 4052. In further embodiments, the density of the fuel composition disclosed herein is measured according to any conventional method known to a skilled artisan for measuring density of fuels.

In some embodiments, the fuel composition has a freezing point that is lower than −30° C., lower than −40° C., lower than −50° C., lower than −60° C., lower than −70° C., or lower than −80° C. In other embodiments, the fuel composition has a freezing point from about −80° C. to about −30° C., from about −75° C. to about −35° C., from about −70° C. to about −40° C., or from about −65° C. to about −45° C. In certain embodiments, the freezing point of the fuel composition disclosed herein is measured according to ASTM Standard D 2386. In further embodiments, the freezing point of the fuel composition disclosed herein is measured according to any conventional method known to a skilled artisan for measuring freezing point of fuels.

In some embodiments, the fuel composition has a density at 15° C. from about 750 kg/m$^3$ to about 850 kg/m$^3$, and a flash point equal to or greater than 38° C. In certain embodiments, the fuel composition has a density at 15° C. from about 750 kg/m$^3$ to about 850 kg/m$^3$, a flash point equal to or greater than 38° C., and a freezing point lower than −40° C. In certain embodiments, the fuel composition has a density at 15° C. from about 750 kg/m$^3$ to about 840 kg/m$^3$, a flash point equal to or greater than 38° C., and a freezing point lower than −40° C.

In some embodiments, the fuel composition has an initial boiling point that is from about 140° C. to about 170° C. In other embodiments, the fuel composition has a final boiling point that is from about 180° C. to about 300° C. In still other embodiments, the fuel composition has an initial boiling that is from about 140° C. to about 170° C., and a final boiling point that is from about 180° C. to about 300° C. In certain embodiments, the fuel composition meets the distillation specification of ASTM D 86.

In some embodiments, the fuel composition has a Jet Fuel Thermal Oxidation Tester (JFTOT) temperature that is equal to or greater than 245° C. In other embodiments, the fuel composition has a JFTOT temperature that is equal to or greater than 250° C., equal to or greater than 255° C., equal to or greater than 260° C., or equal to or greater than 265° C.

In some embodiments, the fuel composition has a viscosity at −20° C. that is less than 6 mm$^2$/sec, less than 7 mm$^2$/sec, less than 8 mm$^2$/sec, less than 9 mm$^2$/sec, or less than 10 mm$^2$/sec. In certain embodiments, the viscosity of the fuel composition disclosed herein is measured according to ASTM Standard D 445.

In some embodiments, the fuel composition meets the ASTM D 1655 specification for Jet A-1. In other embodiments, the fuel composition meets the ASTM D 1655 specification for Jet A. In still other embodiments, the fuel composition meets the ASTM D 1655 specification for Jet B.

In another aspect, the invention provides a fuel composition comprising:
  (a) limonane in an amount that is at least about 5% by volume, based on the total volume of the fuel composition;
  (b) p-cymene in an amount that is at least about 0.5% by volume, based on the total volume of the fuel composition; and,
  (b) a petroleum-based fuel in an amount that is at least 40% by volume, based on the total volume of the fuel composition.

In other embodiments, the limonane is present in an amount that is between about 5% and about 60% by volume, based on the total volume of the fuel composition. In still other embodiments, the limonane is present in an amount that is between about 5% and about 25% by volume, based on the total volume of the fuel composition. In still other embodiments the limonane is present in an amount that is between about 20% and about 50% by volume, based on the total volume of the fuel composition.

In certain other embodiments, the p-cymene is present in an amount that is between about 0.5% and about 25% by volume based on the total volume of the fuel composition. In still other embodiments, the p-cymene is present in an amount that is between about 0.5% and about 10% by volume based on the total volume of the fuel composition.

In certain other embodiments, the fuel composition has a density at 15° C. of between 750 and 840 kg/m3, has a flash point that is equal to or greater than 38° C.; and freezing point that is lower than −40° C. In still other embodiments, the petroleum-based fuel is Jet A and the fuel composition meets the ASTM D 1655 specification for Jet A. In still other embodiments, the petroleum-based fuel is Jet A-1 and the fuel composition meets the ASTM D 1655 specification for Jet A-1. In still other embodiments, the petroleum-based fuel is Jet B and the fuel composition meets the ASTM D 1655 specification for Jet B.

In another aspect, a fuel system is provided comprising a fuel tank containing the fuel composition disclosed herein. Optionally, the fuel system may further comprise an engine cooling system having a recirculating engine coolant, a fuel line connecting the fuel tank with the internal combustion engine, and/or a fuel filter arranged on the fuel line. Some non-limiting examples of internal combustion engines include reciprocating engines (e.g., gasoline engines and diesel engines), Wankel engines, jet engines, some rocket engines, and gas turbine engines.

In some embodiments, the fuel tank is arranged with said cooling system so as to allow heat transfer from the recirculating engine coolant to the fuel composition contained in the fuel tank. In other embodiments, the fuel system further comprises a second fuel tank containing a second fuel for a jet engine and a second fuel line connecting the second fuel tank with the engine. Optionally, the first and second fuel lines can be provided with electromagnetically operated valves that can be opened or closed independently of each other or simultaneously. In further embodiments, the second fuel is a Jet A.

In another aspect, an engine arrangement is provided comprising an internal combustion engine, a fuel tank containing the fuel composition disclosed herein, a fuel line connecting the fuel tank with the internal combustion engine. Optionally, the engine arrangement may further comprise a fuel filter and/or an engine cooling system comprising a recirculating engine coolant. In some embodiments, the internal combustion engine is a diesel engine. In other embodiments, the internal combustion engine is a jet engine.

When using a fuel composition disclosed herein, it is desirable to remove particulate matter originating from the fuel composition before injecting it into the engine. Therefore, it is desirable to select a suitable fuel filter for use in a fuel system disclosed herein. Water in fuels used in an internal combustion engine, even in small amounts, can be very harmful to the engine. Therefore, it is desirable that any water present in fuel composition be removed prior to injection into the engine. In some embodiments, water and particulate matter can be removed by the use of a fuel filter utilizing a turbine centrifuge, in which water and particulate matter are separated from the fuel composition to an extent allowing injection of the filtrated fuel composition into the engine, without risk of damage to the engine. Other types of fuel filters that can remove water and/or particulate matter also may be used.

In another aspect, a vehicle is provided comprising an internal combustion engine, a fuel tank containing the fuel composition disclosed herein, and a fuel line connecting the fuel tank with the internal combustion engine. Optionally, the vehicle may further comprise a fuel filter and/or an engine cooling system comprising a recirculating engine coolant. Some non-limiting examples of vehicles include cars, motorcycles, trains, ships, and aircraft.

Methods for Making Fuel Compositions

In another aspect, provided herein are methods of making a fuel composition comprising the steps of:

(a) contacting an isoprenoid starting material with hydrogen in the presence of a catalyst to form a limonane; and (b) mixing the limonane with a fuel component to make the fuel composition.

In one embodiment, the isoprenoid starting material is limonene

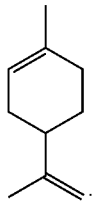

In another embodiment, the isoprenoid starting material is β-phellandrene

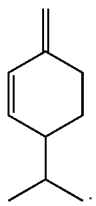

In another embodiment, the isoprenoid starting material is γ-terpinene

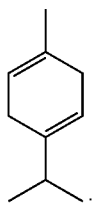

In yet another embodiment, the isoprenoid starting material is terpinolene

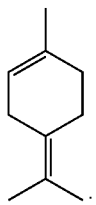

In certain embodiments, when the isoprenoid starting material is contacted with hydrogen in the presence of a catalyst, both limonane and p-cymene are formed. In other embodiments, the isoprenoid starting material is converted into limonane that is substantially free of p-cymene.

In another aspect, provided herein are methods of making a fuel composition from a simple sugar comprising the steps of:

(a) contacting a cell capable of making an isoprenoid starting material with the simple sugar under conditions suitable for making the isoprenoid starting material;

(b) converting the isoprenoid starting material to limonane; and, (c) mixing the limonane with a fuel component to make said fuel composition.

In some embodiments, the isoprenoid starting material is converted into limonane by contacting the isoprenoid starting material with hydrogen in the presence of a catalyst. In certain embodiments, the isoprenoid starting material is converted into both limonane and p-cymene by contacting the isoprenoid starting material with hydrogen in the presence of a catalyst. In these embodiments, both limonane and p-cymene are mixed with a fuel component to make said fuel composition in step (c).

In another aspect, a facility is provided for manufacture of a fuel, bioengineered fuel component, or bioengineered fuel additive of the invention. In certain embodiments, the facility is capable of biological manufacture of the $C_{10}$ starting materials. In certain embodiments, the facility is further capable of preparing an isoprenoid fuel additive or fuel component from the starting material.

The facility can comprise any structure useful for preparing the isoprenoid starting material using a microorganism. In some embodiments, the biological facility comprises one or more of the cells disclosed herein. In some embodiments, the biological facility comprises a cell culture comprising at least an isoprenoid starting material in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells described herein.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing geranyl pyrophosphate (GPP). In further embodiments, the fermentor comprises a cell culture capable of biologically manufacturing isopentenyl diphosphate (IPP). In certain embodiments, the fermentor comprises a cell culture comprising at least an isoprenoid starting material in an amount of at least about 1 wt. %, at least about 5 wt. %, at least about 10 wt. %, at least about 20 wt. %, or at least about 30 wt. %, based on the total weight of the cell culture.

The facility can further comprise any structure capable of manufacturing the fuel component or fuel additive from the isoprenoid starting material. The structure may comprise a hydrogenator for the hydrogenation of the isoprenoid starting material. Any hydrogenator that can be used to reduce C=C double bonds to C—C single bonds under conditions known to skilled artisans may be used herein. The hydrogenator may comprise a hydrogenation catalyst disclosed herein. In some embodiments, the structure further comprises a mixer, a container, and a mixture of the hydrogenation products from the hydrogenation step and a conventional fuel additive in the container.

The simple sugar can be any simple sugar known to those of skill in the art. Some non-limiting examples of suitable simple sugars or monosaccharides include glucose, galactose, mannose, fructose, ribose and combinations thereof.

Some non-limiting examples of suitable disaccharides include sucrose, lactose, maltose, trehalose, cellobiose and combinations thereof. In certain embodiments, the bioengineered fuel component can be obtained from a polysaccharide. Some non-limiting examples of suitable polysaccharides include starch, glycogen, cellulose, chitin and combinations thereof.

The monosaccharides, disaccharides and polysaccharides suitable for making the bioengineered tetramethylcyclohexane can be found in a wide variety of crops or sources. Some non-limiting examples of suitable crops or sources include sugar cane, bagasse, miscanthus, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn.

Methods for Making Compounds

The compounds of the present invention can be made using any method known in the art including biologically, total chemical synthesis (without the use of biologically derived materials), and a hybrid method where both biologically and chemical means are used. In certain embodiments, the isoprenoid starting materials are each made by host cells by the conversion of simple sugar to the desired product.

Host Cells

The isoprenoid starting materials also can be made by any method known in the art including biological methods, chemical syntheses, and hybrid methods. When the isoprenoid starting material is made biologically, host cells that are modified to produce the desired product can be used. Like all isoprenoids, the isoprenoid starting material is made biochemically through a common intermediate, isopentenyl diphosphate ("IPP").

The host cell can be grown according to any technique known to those of skill in the art. In particular, the host cell can be grown in culture medium appropriate for the host cell. In advantageous embodiments, the culture medium comprises readily available, renewable components. The present invention thus provides readily available, renewable sources of energy methods of their use to produce fuel compositions. In certain embodiments, the host cell is grown or cultured by contact with a simple sugar under conditions suitable for their growth and production of an isoprenoid starting material. In certain embodiments, the host cell can be grown or cultured by contact with glucose, galactose, mannose, fructose, ribose, or a combination thereof. The present invention thus provides fuel compositions derived from simple sugars, e.g. glucose, galactose, mannose, fructose, ribose, and combinations thereof, and methods of their production from the simple sugars.

Any suitable host cell may be used in the practice of the methods and compositions described herein. In one embodiment, the host cell is a genetically modified host microorganism in which nucleic acid molecules have been inserted, deleted or modified (i.e., mutated; e.g., by insertion, deletion, substitution, and/or inversion of nucleotides), either to produce the desired isoprenoid or isoprenoid derivative, or to produce increased yields of the desired isoprenoid or isoprenoid derivative. In certain embodiments, the host cell is capable of being grown in liquid growth medium.

Illustrative examples of suitable host cells include any archae, bacterial, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum*, and *Thermoplasma volcanium*.

Examples of useful bacterial species include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of useful bacterial species include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of useful eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces*, and *Trichoderma*.

Illustrative examples of useful eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus*, and *Trichoderma reesei*.

In general, if a eukaryotic cell is used, a non-pathogenic species is preferred. Illustrative examples of non-pathogenic species include but are not limited to: *Fusarium graminearum, Fusarium venenatum, Pichia pastoris, Saccaromyces boulardi*, and *Saccaromyces cerevisiae*.

In addition, certain species have been designated by the Food and Drug Administration as GRAS or Generally Regarded As Safe. These strains include: *Bacillus subtilis, Lactibacillus acidophilus, Lactobacillus helveticus*, and *Saccharomyces cerevisiae*.

IPP Pathways

There are two known biosynthetic pathways that synthesize IPP and its isomer, dimethylallyl pyrophosphate ("DMAPP"). Eukaryotes other than plants use the mevalonate-dependent ("MEV") isoprenoid pathway exclusively to convert acetyl-coenzyme A ("acetyl-CoA") to IPP, which is subsequently isomerized to DMAPP. Prokaryotes, with some exceptions, use the mevalonate-independent or deoxyxylulose 5-phosphate ("DXP") pathway to produce IPP and DMAPP separately through a branch point. In general, plants use both the MEV and DXP pathways for IPP synthesis.

MEV Pathway

A schematic representation of the MEV pathway is described in FIG. 1. In general, the pathway comprises six steps.

In the first step, two molecules of acetyl-coenzyme A are enzymatically combined to form acetoacetyl-CoA. An enzyme known to catalyze this step is, for example, acetyl-CoA thiolase. Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

If IPP is to be converted to DMAPP using the mevalonate pathway, then a seventh step is required. An enzyme known to catalyze this step is, for example, IPP isomerase. Illustrative examples of nucleotide sequences include but are not limited to: (NC_000913, 3031087 . . . 3031635; *Escherichia coli*), and (AF082326; *Haematococcus pluvialis*).

DXP Pathway

Figure 2:
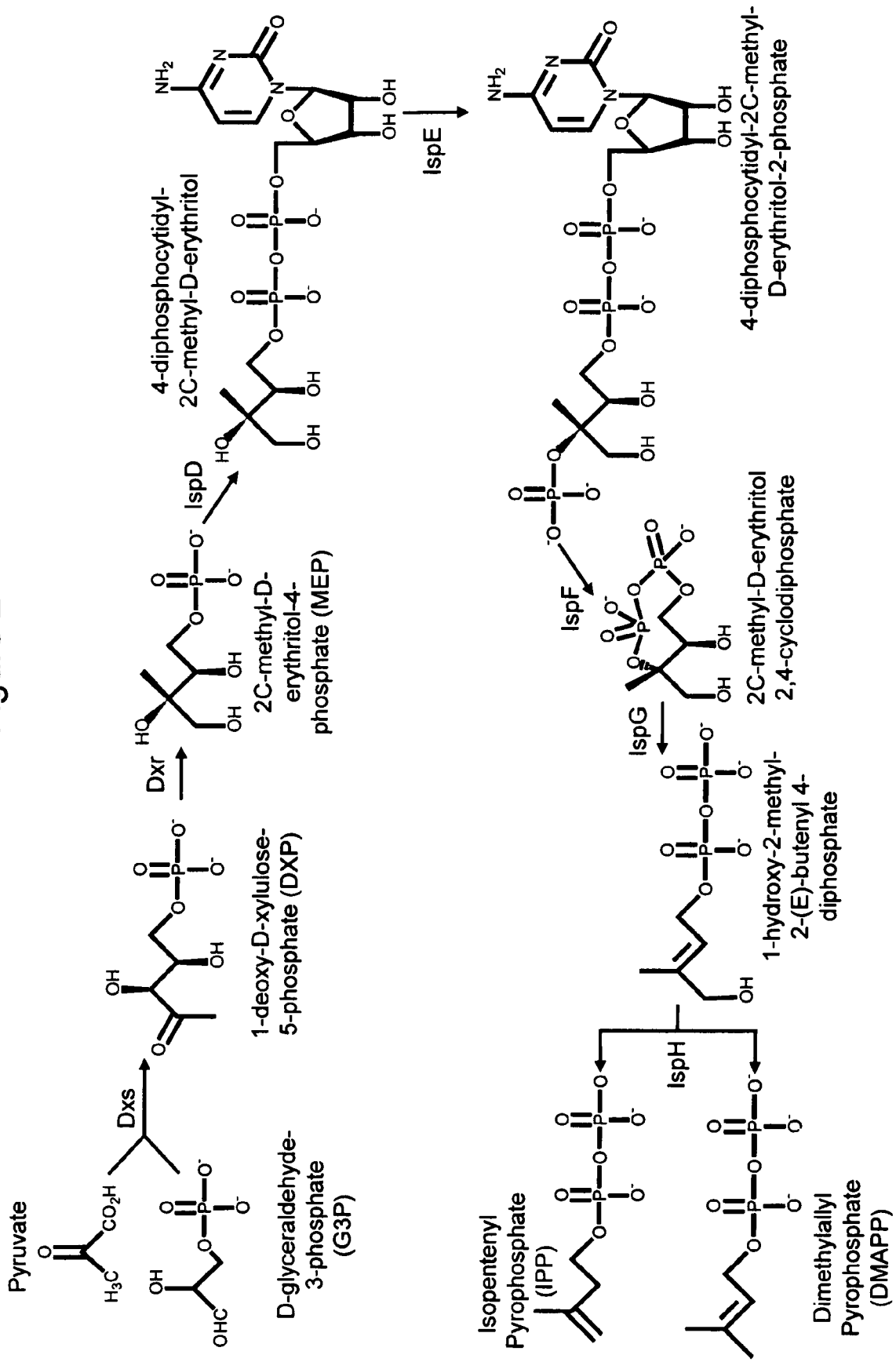
FIG. 2 is a schematic representation of the 1-deoxy-D-xylulose 5-diphosphate ("DXP") pathway for the production of isopentenyl pyrophosphate ("IPP") and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

A schematic representation of the DXP pathway is described in FIG. 2. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PPO527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa* Temecula1), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP 2709; *Rhodobacter sphaeroides* 2.4.1), and (NC 007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus tag RSP_2835; *Rhodobacter sphaeroides* 2.4.1), (NC_003071, locus_tag AT2G02500; *Arabidopsis thaliana*), and (NC_002947, locus tag PP 1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus tag PP0606; *Pseudomonas putida* KT2440).

In some embodiments, "cross talk" (or interference) between the host cell's own metabolic processes and those processes involved with the production of IPP as provided herein are minimized or eliminated entirely. For example; cross talk is minimized or eliminated entirely when the host microorganism relies exclusively on the DXP pathway for synthesizing IPP, and a MEV pathway is introduced to provide additional IPP. Such a host organisms would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

Isoprenoid Starting Material

Figure 3:
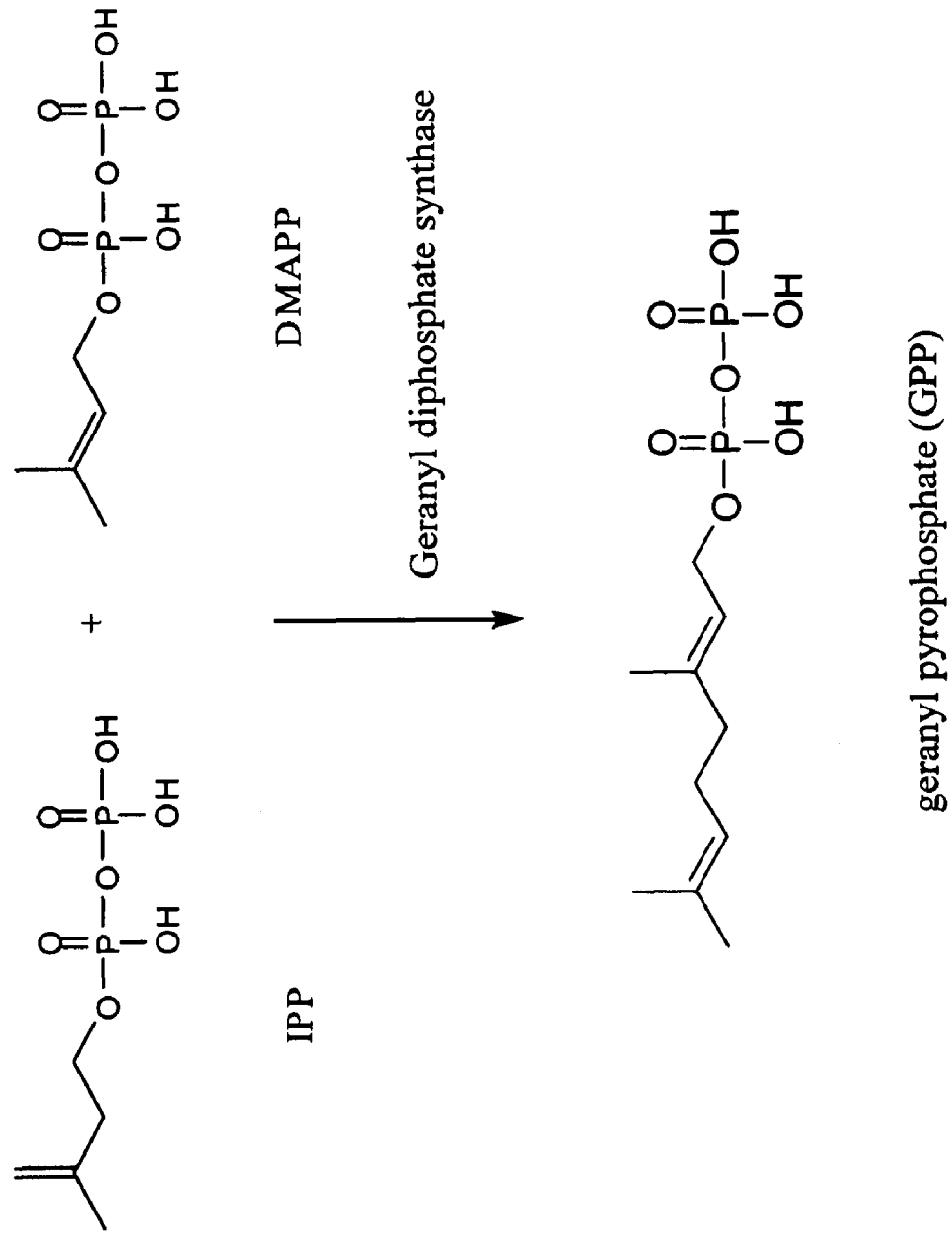
FIG. 3 is a schematic representation of the conversion of one molecule of IPP and one molecule of DMAPP to geranyl pyrophosphate ("GPP"). An enzyme known to catalyze this step is, for example, geranyl diphosphate synthase.

In some embodiments GPP is prepared by the method as described schematically in FIG. 3. One molecule of IPP and one molecule of DMAPP are condensed to form GPP. In some embodiments, the reaction can be catalyzed by an enzyme known to catalyze this step, for example, geranyl diphosphate synthase. Various isoprenoid starting materials can be made from GPP.

Illustrative examples of polynucleotides encoding geranyl pyrophosphate synthase include but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×piperita*), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

GPP can then be subsequently converted to various isoprenoid starting materials using one or more terpene synthases. Some non-limiting examples include the following examples and stereoisomers thereof.

Limonene

Limonene, whose structure is

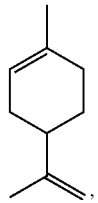

is found in the rind of citrus fruits and peppermint. Limonene is made from GPP by limonene synthase. Illustrative examples of suitable nucleotide sequences include but are not limited to: (+)-limonene synthases (AF514287, REGION: 47 . . . 1867; *Citrus limon*) and (AY055214, REGION: 48 . . . 1889; *Agastache rugosa*) and (−)-limonene synthases (DQ195275, REGION: 1 . . . 1905; *Picea sitchensis*), (AF006193, REGION: 73 . . . 1986; *Abies grandis*), and (MHC4SLSP, REGION: 29 . . . 1828; *Mentha spicata*).

β-Phellandrene

β-Phellandrene having the following structure:

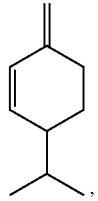

is a constituent of the essential oil of *Buplerum fruticosum*. Biochemically, β-phellandrene is made from GPP by a β-phellandrene synthase. A non-limiting example of a suitable nucleotide sequence includes GenBank accession number AF139205, REGION: 34 . . . 1926, from *Abies grandis*.

γ-Terpinene

γ-Terpinene having the following structure:

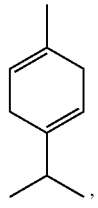

is a constituent of the essential oil from citrus fruits. Biochemically, γ-terpinene is made from GPP by a γ-terpinene synthase. Some non-limiting examples of suitable nucleotide sequences include GenBank accession number AF514286, REGION: 30 . . . 1832 from *Citrus limon* and AB110640, REGION 1 . . . 1803 from *Citrus unshiu*.

Terpinolene

Terpinolene having the following structure:

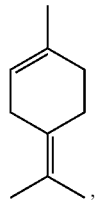

is a constituent of number essential oils. Biochemically, terpinolene is made from GPP by a terpinolene synthase. A non-limiting example of a suitable nucleotide sequence includes AY906866, REGION: 10 . . . 1887 from *Pseudotsuga menziesii*.

In some embodiments, the isoprenoid starting material can be obtained or prepared from naturally occurring terpenes that can be produced by a wide variety of plants, such as *Copaifera langsdorfii*, conifers, and spurges; insects, such as swallowtail butterflies, leaf beetles, termites, and pine sawflies; and marine organisms, such as algae, sponges, corals, mollusks, and fish.

*Copaifera langsdorfii* or Copaifera tree is also known as the diesel tree and kerosene tree. It has many names in local languages, including kupa'y, cabismo, and copaúva. Copaifera tree may produce a large amount of terpene hydrocarbons in its wood and leaves. Generally, one Copaifera tree can produce from about 30 to about 40 liters of terpene oil per year.

Terpene oils can also be obtained from conifers and spurges. Conifers belong to the plant division Pinophyta or Coniferae and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces; and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

The isoprenoid starting materials are monoterpenes which are part of a larger class of compound called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, suitable isoprenoid starting materials can be isolated from terpene oils for use in the present invention.

Chemical Conversion

In certain embodiments, limonane and p-cymene in the fuel compositions provided herein are prepared by hydrogenating an isoprenoid starting material.

Illustrative examples of suitable isoprenoid starting materials include, but are not limited to, limonene, β-phellandrene, γ-terpinene, terpinolene and any combination thereof.

In some embodiments, hydrogenation occurs by reacting the isoprenoid starting material with hydrogen in the presence of a catalyst such as Pd, Pd/C, Pt, $PtO_2$, $Ru(PPh_3)_2Cl_2$, Raney nickel and combinations thereof. Alternatively, any reducing agent that can reduce a C=C bond to a C—C bond can be used. An illustrative example of such a reducing agent is hydrazine in the presence of a catalyst, such as 5-ethyl-3-methyllumiflavinium perchlorate, under an oxygen atmosphere. A reduction reaction with hydrazine is disclosed in Imada et al., *J. Am. Chem. Soc.*, 127, 14544-14545 (2005), which is incorporated herein by reference.

The catalyst for the hydrogenation reaction of the isoprenoid starting materials can be present in any amount for the reaction to proceed. In some embodiments, the amount of the hydrogenation catalyst is from about 1 g to about 100 g per liter of reactant, from about 2 g to about 75 g per liter of reactant, from about 3 g to about 50 g per liter of reactant, from about 4 g to about 40 g per liter of reactant, from about 5 g to about 25 g per liter of reactant, or from about 5 g to about 10 g per liter of reactant.

In some embodiments, the catalyst is a Pd catalyst. In other embodiments, the catalyst is 5% Pd/C. In still other embodiments, the catalyst is 10% Pd/C. In certain of these embodiments, the catalyst loading is between about 1 g and about 10 g per liter of reactant. In other embodiments, the catalyst loading is between about 5 g and about 5 g per liter of reactant.

In some embodiments, the hydrogenation reaction proceeds at room temperature. However, because the hydrogenation reaction is exothermic, the temperature of the reaction mixture can increase as the reaction proceeds. When the reaction temperature is kept at or near room temperature, substantially all of the product formed will be limonane. However, increasing amounts of p-cymene are formed as the temperature increases. Thus in certain embodiments where the amount of p-cymene is to be minimized, the reaction temperature is from about 10° C. to about 75° C., from about 15° C. to about 60° C., from about 20° C. to about 50° C., or from about 20° C. to about 40° C., inclusive. In other embodiments where an appreciable amount of p-cymene is desired, the reaction temperature is from about 75° C. to about 150° C., between from about 90° C. to about 130° C., or from about 100° C. to about 125° C.

The pressure of the hydrogen for the hydrogenation reaction can be any pressure that can cause the reaction to proceed. In some embodiments, the pressure of the hydrogen is from about 10 psi to about 1000 psi, from about 50 psi to about 800 psi, from about 400 psi to about 600 psi, or from about 450 psi to about 550 psi. In other embodiments, the pressure of hydrogen is less than 100 psi.

In some embodiments, the conversion of the isoprenoid starting material to limonane occurs in two steps. In the first, a portion of the isoprenoid starting material is converted to p-cymene in a disproportion reaction where the isoprenoid starting material is contacted with a hydrogenation catalyst in the presence of heat. In some embodiments, the reaction temperature of the first step is from about 75° C. to about 150° C., from about 90° C. to about 130° C., or from about 100° C. to about 125° C. In the second, the remaining portion of the isoprenoid starting material (that has not converted to p-cymene) is converted to limonane in a hydrogenation reaction. In some embodiments, the reaction temperature of the second step is from about 10° C. to about 75° C., from about 15° C. to about 60° C., from about 20° C. to about 50° C., or from about 20° C. to about 40° C.

Business Methods

One aspect of the present invention relates to a business method comprising: (a) obtaining a biofuel comprising limonane derived from an isoprenoid starting material by performing a fermentation reaction of a sugar with a recombinant host cell, wherein the recombinant host cell produces the isoprenoid starting material; and (b) marketing and/or selling said biofuel.

In other embodiments, the invention provides a method for marketing or distributing the biofuel disclosed herein to marketers, purveyors, and/or users of a fuel, which method comprises advertising and/or offering for sale the biofuel disclosed herein. In further embodiments, the biofuel disclosed herein may have improved physical or marketing characteristics relative to the natural fuel or ethanol-containing biofuel counterpart.

In certain embodiments, the invention provides a method for partnering or collaborating with or licensing an established petroleum oil refiner to blend the biofuel disclosed herein into petroleum-based fuels such as a gasoline, jet fuel, kerosene, diesel fuel or a combination thereof. In another embodiment, the invention provides a method for partnering or collaborating with or licensing an established petroleum oil refiner to process (for example, hydrogenate, hydrocrack, crack, further purify) the biofuels disclosed herein, thereby modifying them in such a way as to confer properties beneficial to the biofuels. The established petroleum oil refiner can use the biofuel disclosed herein as a feedstock for further chemical modification, the end product of which could be used as a fuel or a blending component of a fuel composition.

In further embodiments, the invention provides a method for partnering or collaborating with or licensing a producer of sugar from a renewable resource (for example, corn, sugar cane, bagass, or lignocellulosic material) to utilize such renewable sugar sources for the production of the biofuels disclosed herein. In some embodiments, corn and sugar cane, the traditional sources of sugar, can be used. In other embodiments, inexpensive lignocellulosic material (agricultural waste, corn stover, or biomass crops such as switchgrass and pampas grass) can be used as a source of sugar. Sugar derived from such inexpensive sources can be fed into the production of the biofuel disclosed herein, in accordance with the methods of the present invention.

In certain embodiments, the invention provides a method for partnering or collaborating with or licensing a chemical producer that produces and/or uses sugar from a renewable resource (for example, corn, sugar cane, bagass, or lignocellulosic material) to utilize sugar obtained from a renewable resource for the production of the biofuel disclosed herein.

EXAMPLES

The following examples are intended for illustrative purposes only and do not limit in any way the scope of the present invention.

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for making expression plasmids that encode enzymes including enzymes of the MEV pathway from *Saccharomyces cerevisiae* organized in operons.

Expression plasmid pMevT was generated by inserting the MevT operon into the pBAD33 vector. The MevT operon encodes the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT operon was generated by PCR amplifying from *Escherichia coli* genomic DNA the coding sequence of the atoB gene (GenBank accession number NC_000913 REGION: 2324131 . . . 2325315) (encodes an acetoacetyl-CoA thiolase), from *Saccharomyces cerevisiae* genomic DNA the coding sequence of the ERG13 gene (GenBank accession number X96617, REGION: 220 . . . 1695) (encodes a HMG-CoA synthase), and from *Saccharomyces cerevisiae* genomic DNA a segment of the coding region of the HMG1 gene (GenBank accession number M22002, REGION: 1660 . . . 3165) (encodes a truncated HMG-CoA reductase (tHMGR)). The upstream PCR primer used for the amplification of the HMG1 gene fragment included an artificial start codon. The amplified fragments were spliced together using overlap extensions (SOEing), during which process ribosome binding sites were introduced after the atoB and the ERG13 coding sequences. After the addition of 3' A overhangs, the MevT operon was ligated into the TA cloning vector pCR4 (Invitrogen, Carlsbad, Calif.). The MevT operon was subsequently ligated into the XmaI PstI restriction site of vector pBAD33 (Guzman et al. (1995) *J. Bacteriol.* 177(14): 4121-4130). To place the operon under the control of the $P_{Lac}$ promoter, the araC-$P_{BAD}$ NsiI-XmaI fragment of pBAD33 was replaced with the NsiI-XmaI fragment of pBBR1MCS, yielding expression plasmid pMevT (see U.S. Pat. No. 7,192,751).

Expression plasmid pAM36-MevT66 was generated by inserting the MevT66 operon into the pAM36 vector. The pAM36 vector was generated by inserting an oligonucleotide cassette containing AscI-SfiI-AsiSI-XhoI-PacI-FsII-PmeI restriction sites into the pACYC184 vector (GenBank accession number X06403), and by removing the tetramycin resistance conferring gene in pACYC184. The MevT66 operon was synthetically generated using SEQ ID NO: 1 as a template, which comprises the atoB gene from *Escherichia coli* (GenBank accession number NC_000913 REGION: 2324131 . . . 2325315), the ERG13 gene from *Saccharomyces cerevisiae* (GenBank accession number X96617, REGION: 220 . . . 1695), and a truncated version of the HMG1 gene from *Saccharomyces cerevisiae* (GenBank accession number M22002, REGION: 1777 . . . 3285), all three sequences being codon-optimized for expression in *Escherichia coli*. The synthetically generated MevT66 operon was flanked by a 5' EcoRI restriction site and a 3' Hind III restriction site, and could thus be cloned into compatible restriction sites of a cloning vector such as a standard pUC or pACYC origin vector. From this construct, the MevT66 operon was PCR amplified with flanking SfiI and AsiSI restriction sites, the amplified DNA fragment was digested to completion using SfiI and AsiSI restriction enzymes, the reaction mixture was resolved by gel electrophoresis, the approximately 4.2 kb DNA fragment was gel extracted using a gel purification kit (Qiagen, Valencia, Calif.), and the isolated DNA fragment was ligated into the SfiI AsiSI restriction site of the pAM36 vector, yielding expression plasmid pAM36-MevT66.

Expression plasmid pAM25 was generated by inserting the MevT66 operon into the pAM29 vector. The pAM29 vector was created by assembling the p15A origin of replication and kanamycin resistance conferring gene from pZS24-MCS1 (Lutz and Bujard (1997) *Nucl Acids Res.* 25:1203-1210) with an oligonucleotide-generated lacUV5 promoter. The DNA synthesis construct comprising the MevT66 operon (see description for pAM36-MevT66 above) was digested to completion using EcoRI and Hind III restriction enzymes, the reaction mixture was resolved by gel electrophoresis, the approximately 4.2 kb DNA fragment was gel extracted, and the isolated DNA fragment was ligated into the EcoRI HindIII restriction site of pAM29, yielding expression plasmid pAM25.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The MevB operon was generated by PCR amplifying from *Saccharomyces cerevisiae* genomic DNA the coding sequences of the ERG12 gene (GenBank accession number X55875, REGION: 580 . . . 1911) (encodes a mevalonate kinase), the ERG8 gene (GenBank accession number Z49939, REGION: 3363 . . . 4718) (encodes a phosphomevalonate kinase), and the MVD1 gene (GenBank accession number X97557, REGION: 544 . . . 1734) (encodes a mevalonate pyrophosphate carboxylase), and by splicing the PCR fragments together using overlap extensions (SOEing). By choosing appropriate primer sequences, the stop codons of ERG12 and ERG8 were changed from TAA to TAG during amplification to introduce ribosome binding sites. After the addition of 3' A overhangs, the MevB operon was ligated into the TA cloning vector pCR4 (Invitrogen, Carlsbad, Calif.). The MevB operon was excised by digesting the cloning construct to completion using PstI restriction enzyme, resolving the reaction mixture by gel electrophoresis, gel extracting the approximately 4.2 kb DNA fragment, and ligating the isolated DNA fragment into the PstI restriction site of vector pBBR1MCS-1 (Kovach et al., *Gene* 166(1): 175-176 (1.995)), yielding expression plasmid pMevB-Cm.

Expression plasmid pMBI was generated by inserting the MBI operon into the pBBR1MCS-3 vector. In addition to the enzymes of the MevB operon, the MBI operon also encodes an isopentenyl pyrophosphatase isomerase, which catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends, digesting the amplified DNA fragment to completion using XmaI restriction enzyme, resolving the reaction mixture by gel electrophoresis, gel extracting the approximately 0.5 kb fragment, and ligating the isolated DNA fragment into the XmaI restriction site of expression plasmid pMevB-Cm, thereby placing idi at the 3' end of the MevB operon. The MBI operon was subcloned into the SalI SacI restriction site of vector pBBR1MCS-3 (Kovach et al., *Gene* 166(1): 175-176 (1995)), yielding expression plasmid pMBI (see U.S. Pat. No. 7,192,751).

Expression plasmid pMBIS was generated by inserting the ispA gene into pMBI. The ispA gene encodes a farnesyl diphosphate synthase, which catalyzes the condensation of two molecules of IPP with one molecule of DMAPP to make farnesyl pyrophosphate (FPP). The coding sequence of the ispA gene (GenBank accession number D00694, REGION: 484 . . . 1383) was PCR amplified from *Escherichia coli* genomic DNA using a forward primer with a SacII restriction site and a reverse primer with a SacI restriction site. The amplified PCR product was digested to completion using SacII and SacI restriction enzymes, the reaction mixture was resolved by gel electrophoresis, and the approximately 0.9 kb DNA fragment was gel extracted, and the isolated DNA fragment was ligated into the SacII SacI restriction site of pMBI, thereby placing the ispA gene 3' of idi and the MevB operon, and yielding expression plasmid pMBIS (see U.S. Pat. No. 7,192,751).

Expression plasmid pMBIS-gpps was derived from expression plasmid pMBIS by replacing the ispA coding sequence with a nucleotide sequence encoding a geranyl diphosphate synthase ("gpps"). A DNA fragment comprising a nucleotide sequence encoding a geranyl diphosphate synthase was generated synthetically using the coding sequence of the gpps gene of *Arabidopsis thaliana* (GenBank accession number Y17376, REGION: 52 . . . 1320), codon-optimized for expression in *Escherichia coli*, as a template (SEQ ID NO: 2). The nucleotide sequence was flanked by a leader SacII restriction site and a terminal SacI restriction site, and could thus be cloned into compatible restriction sites of a cloning vector such as a standard pUC or pACYC origin vector. The synthetically generated geranyl diphosphate synthase sequence was isolated by digesting the DNA synthesis construct to completion using SacII and SacI restriction enzymes, resolving the reaction mixture by gel electrophoresis, gel extracting the approximately 1.3 kb DNA fragment, and ligating the isolated DNA fragment into the SacII SacI restriction site of expression plasmid pMBIS, yielding expression plasmid pMBIS-gpps.

Example 2

This example describes methods for making expression vectors encoding enzymes including enzymes of the MEV pathway from *Staphylococcus aureus* organized in operons.

Expression plasmid pAM41 was derived from expression plasmid pAM25 by replacing the coding sequence of the HMG1 gene, which encodes the *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925 . . . 2687648). The coding sequence of the mvaA gene was PCR amplified from *Staphylococcus aureus* subsp. *aureus* (ATCC 70069) genomic DNA using primers 4-49 mvaA SpeI (SEQ ID NO: 13) and 4-49 mvaAR XbaI (SEQ ID NO: 14), the amplified DNA fragment was digested to completion using SpeI restriction enzyme, the reaction mixture was resolved by gel electrophoresis, and the approximately 1.3 kb DNA fragment was gel extracted. The HMG1 coding sequence was removed from pAM25 by digesting the plasmid to completion using HindIII restriction enzyme. The terminal overhangs of the resulting linear DNA fragment were blunted using T4 DNA polymerase. The DNA fragment was then partially digested using SpeI restriction enzyme, the reaction mixture was resolved by gel electrophoresis, and the 4.8 kb DNA fragment was gel extracted. The isolated DNA fragment was ligated with the SpeI-digested mvaA PCR product, yielding expression plasmid pAM41.

Expression plasmid pAM52 was derived from expression plasmid pAM41 by replacing the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 . . . 2690346). The coding sequence of the mvaS gene was PCR amplified from *Staphylococcus aureus* subsp.

aureus (ATCC 70069) genomic DNA using primers HMGS 5' Sa mvaS-S (SEQ ID NO: 15) and HMGS 3' Sa mvaS-AS (SEQ ID NO: 16), and the amplified DNA fragment was used as a PCR primer to replace the coding sequence of the HMG1 gene in pAM41 according to the method of Geiser et al. (*BioTechniques* 31:88-92 (2001)), yielding expression plasmid pAM52.

Example 3

This example describes methods for making expression plasmids that encode enzymes including enzymes of the DXP pathway from *Escherichia coli* organized in operons.

Figure 4A:
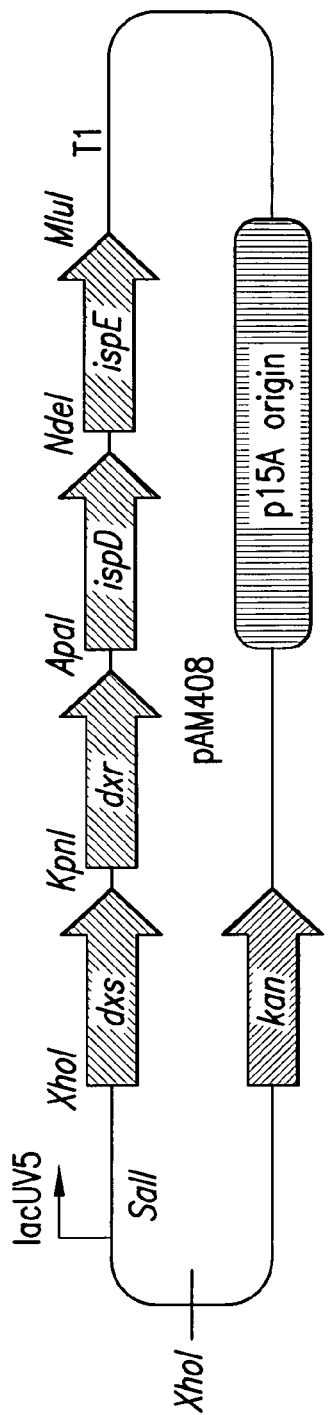
FIGS. 4A-C show maps of expression plasmids pAM408, pAM409, and pAM424.

Expression plasmid pAM408 was generated by inserting genes encoding enzymes of the "top" DXP pathway into the pAM29 vector. Enzymes of the "top" DXP pathway include 1-deoxy-D-xylulose-5-phosphate synthase (encoded by the dxs gene of *Escherichia coli*), 1-deoxy-D-xylulose-5-phosphate reductoisomerase (encoded by the dxr gene of *Escherichia coli*), 4-diphosphocytidyl-2C-methyl-D-erythritol synthase (encoded by the ispD gene of *Escherichia coli*), and 4-diphosphocytidyl-2C-methyl-D-erythritol synthase (encoded by the ispE gene of *Escherichia coli*), which together transform pyruvate and D-glyceraldehyde-3-phosphate into 4-diphosphocytidyl-2C-methyl-D-erythritol-2-phosphate. DNA fragments comprising nucleotide sequences that encode enzymes of the "top" DXP pathway were generated by PCR amplifying the coding sequences of the dxs (GenBank accession number U00096 REGION: 437539 . . . 439-401), dxr (GenBank accession number U00096 REGION: 193521 . . . 194717), ispD (GenBank accession number U00096 REGION: 2869803 . . . 2870512), and ispE (GenBank accession number U00096 REGION 1261249 . . . 1262100) genes from *Escherichia coli* strain DH1 (ATCC #33849) with added optimal Shine Dalgarno sequences and 5' and 3' restriction sites using the PCR primers shown in SEQ ID NOs: 17 through 24. The PCR products were resolved by gel electrophoresis, gel extracted, digested to completion using appropriate restriction enzymes (XhoI and KpnI for the PCR product comprising the dxs gene; KpnI and ApaI for the PCR product comprising the dxr gene; ApaI and NdeI for the PCR product comprising the ispD gene; NdeI and MluI for the PCR product comprising the ispE gene), and purified using a PCR purification kit (Qiagen, Valencia, Calif.). Roughly equimolar amounts of each PCR product were then added to a ligation reaction to assemble the individual genes into an operon. From this ligation reaction, 1 ul of reaction mixture was used to PCR amplify two separate gene cassettes, namely the dxs-dxr and the ispD-ispE gene cassettes. The dxs-dxr gene cassette was PCR amplified using primers 67-1A-C (SEQ ID NO: 17) and 67-1D-C (SEQ ID NO: 20), and the ispD-ispE gene cassette was PCR amplified using primers 67-1E-C (SEQ ID NO: 21) and 67-1H-C (SEQ ID NO: 24). The two PCR products were resolved by gel electrophoresis, and gel extracted. The PCR product comprising the dxs-dxr gene cassette was digested to completion using XhoI and ApaI restriction enzymes, and the PCR product comprising the ispD-ispE gene cassette was digested to completion using ApaI and MluI restriction enzymes. The two PCR products were purified, and the purified DNA fragments were ligated into the SalI MluI restriction site of the pAM29 vector, yielding expression plasmid pAM408 (see FIG. 4A for a plasmid map).

Figure 4B:
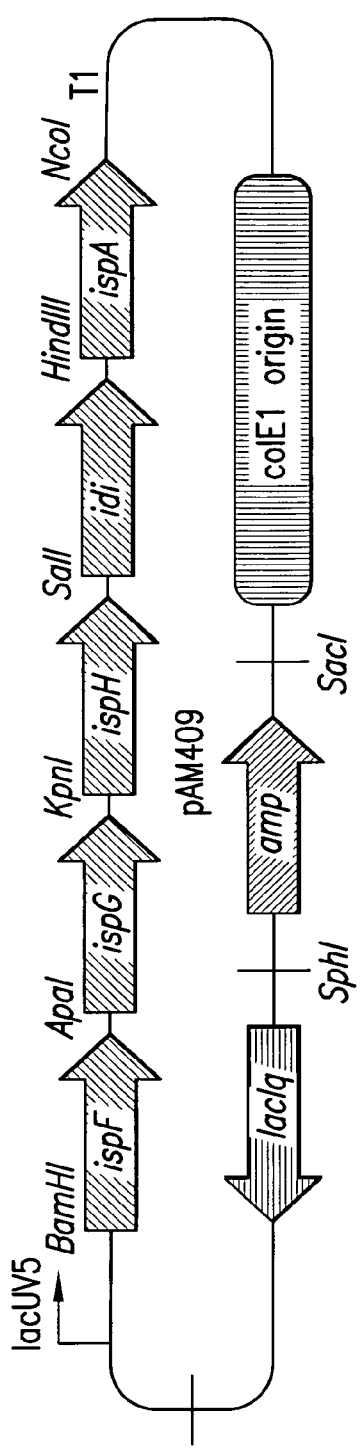

Expression plasmid pAM409 was generated by inserting genes encoding enzymes of the "bottom" DXP pathway into the pAM369 vector. Enzymes of the "bottom" DXP pathway include 2C-methyl-D-erythritol 2,4-cyclodiphosphate synthase (encoded by the ispF gene of *Escherichia coli*), 1-hydroxy-2-methyl-2-(E)-butenyl-4-diphosphate synthase (encoded by the ispG gene of *Escherichia coli*), and isopentenyl/dimethylallyl diphosphate synthase (encoded by the ispH gene of *Escherichia coli*), which together transform 4-diphosphocytidyl-2C-methyl-D-erythritol-2-phosphate to IPP and DMAPP. IPP is also converted to DMAPP through the activity of isopentyl diphosphate isomerase (encoded by the idi gene of *Escherichia coli*). DMAPP can be further converted to FPP through the activity of a farnesyl diphosphate synthase (such as encoded by the ispA gene of *Escherichia coli*). An operon encoding enzymes of the "bottom" DXP pathway as well as an isopentyl diphosphate isomerase and a farnesyl diphosphate synthase was generated by PCR amplifying the ispF (GenBank accession number U00096 REGION: 2869323 . . . 2869802), ispG (GenBank accession number U00096 REGION: 2638708 . . . 2639826), ispH (GenBank accession number U00096 REGION: 26277 . . . 27227), idi (GenBank accession number AF119715), and ispA (GenBank accession number D00694 REGION: 484 . . . 1383) genes from *Escherichia coli* strain DH1 (ATCC #33849) with added optimal Shine Dalgarno sequences and 5' and 3' restriction sites using the PCR primers shown in SEQ ID NOs: 25 through 34. The PCR products were resolved by gel electrophoresis, gel extracted, digested with the appropriate restriction enzymes (BamHI and ApaI for the PCR product comprising the ispF gene; KpnI and ApaI for the PCR product comprising the ispG gene; SalI and KpnI for the PCR product comprising the ispH gene; SalI and HindIII for the PCR product comprising the idi gene; HindIII and NcoI for the PCR product comprising the ispA gene), and purified. Roughly equimolar amounts of each PCR product were then added to a ligation reaction to assemble the individual genes into an operon. From this ligation reaction, 1 ul of reaction mixture was used to PCR amplify two separate gene cassettes, namely the ispF-ispG and the ispH-idi-ispA gene cassettes. The ispF-ispG gene cassette was PCR amplified using primers 67-2A-C (SEQ ID NO: 25) and 67-2D-C (SEQ ID NO: 28), and the ispH-idi-ispA gene cassette was PCR amplified using primers 67-2E-C (SEQ ID NO: 29) and 67-2J-C (SEQ ID NO: 34). The two PCR products were resolved by gel electrophoresis, and gel extracted. The PCR product comprising the ispF-ispG gene cassette was digested to completion using BamHI and KpnI restriction enzymes, and the PCR product comprising the ispH-idi-ispA gene cassette was digested to completion using KpnI and NcoI restriction enzymes. The two PCR products were purified. Vector pAM369 was created by assembling the p15A origin of replication from pAM29 and beta-lactamase gene for ampicillin resistance from pZE12-luc (Lutz and Bujard (1997) *Nucl Acids Res.* 25:1203-1210) with an oligonucleotide-generated lacUV5 promoter. The two isolated PCR products containing the "bottom" DXP pathway operon were ligated into the BamHI NcoI restriction site of the pAM369 vector, yielding expression plasmid pAM409 (see FIG. 4B for a plasmid map).

Figure 4C:
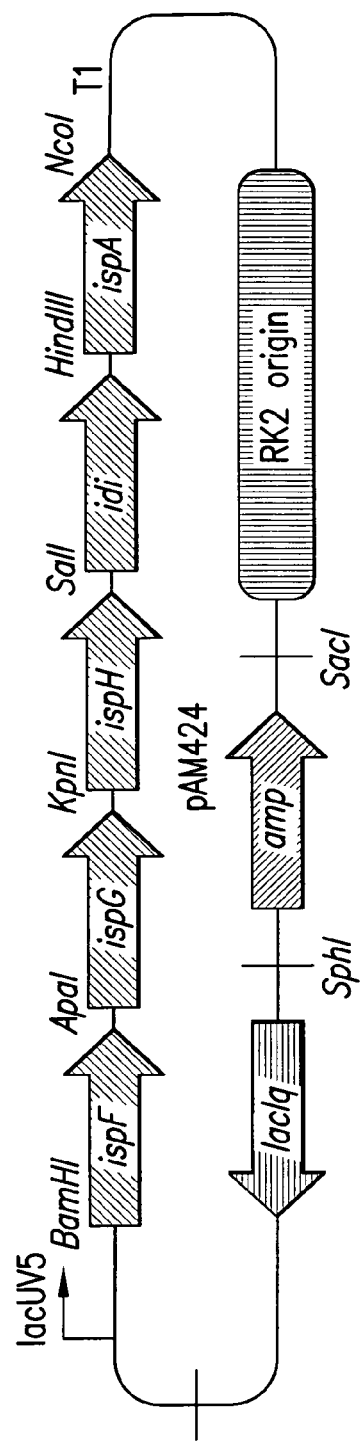

Expression plasmid pAM424, a derivative of expression plasmid pAM409 containing the broad-host range RK2 origin of replication, was generated by transferring the lacUV5 promoter and the ispFGH-idi-ispA operon of pAM409 to the pAM257 vector. Vector pAM257 was generated as follows: the RK2 par locus was PCR-amplified from RK2 plasmid DNA (Meyer et al. (1975) *Science* 190:1226-1228) using primers 9-156A (SEQ ID NO: 35) and 9-156B (SEQ ID NO: 36), the 2.6 kb PCR product was digested to completion using AatII and XhoI restriction enzymes, and the DNA fragment was ligated into a plasmid containing the p15 origin of replication and the chloramphenicol resistance conferring gene from vector pZA31-luc (Lutz and Bujard (1997) Nucl Acids Res. 25:1203-1210), yielding plasmid pAM37-par; pAM37-par was digested to completion using restriction enzymes SacI and HindIII, the reaction mixture was resolved by gel electrophoresis, the DNA fragment comprising the RK2 par locus and the chloramphenicol resistance gene was gel extracted, and the isolated DNA fragment was ligated into the SacI HindIII site of the mini-RK2 replicon pRR10 (Roberts et al. (1990) J. Bacteriol. 172:6204-6216), yielding vector pAM133; pAM133 was digested to completion using BglII and HindIII restriction enzymes, the reaction mixture was resolved by gel electrophoresis, the approximately 6.4 kb DNA fragment lacking the ampicillin resistance gene and oriT conjugative origin was gel extracted, and the isolated DNA fragment was ligated with a synthetically generated DNA fragment comprising a multiple cloning site that contained PciI and XhoI restriction sites, yielding vector pAM257. Expression plasmid pAM409 was digested to completion using XhoI and PciI restriction enzymes, the reaction mixture was resolved by gel electrophoresis, the approximately 4.4 kb DNA fragment was gel extracted, and the isolated DNA fragment was ligated into the XhoI PciI restriction site of the pAM257 vector, yielding expression plasmid pAM424 (see FIG. 4C for a plasmid map).

Example 4

This example describes methods for making vectors for the targeted integration of nucleic acids encoding enzymes including enzymes of the MEV pathway into specific chromosomal locations of Saccharomyces cerevisiae.

Genomic DNA was isolated from Saccharomyces cerevisiae strains Y002 (CEN.PK2 background; MATA; ura3-52; trp1-289; leu2-3,112; his3Δ1; MAL2-8C; SUC2), Y007 (S288C background MATA trp1Δ63), Y051 (S288C background; MATαhis3Δ1 leu2Δ0 lys2Δ0 ura3Δ0 $P_{GAL1}$-HMG1$^{1586-3323}$ $P_{GAL1}$-upc2-1 erg9::$P_{MET3}$-ERG9::HIS3 $P_{GAL1}$-ERG20 $P_{GAL1}$-HMG1$^{1586-3323}$) and EG123 (MATA ura3; trp1; leu2; his4 can1). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (Nanoprop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc, Foster City, Calif.) using the Phusion High Fidelity DNA Polymerase system (Finnzymes OY, Espoo, Finland) as per manufacturer's suggested protocol. Upon the completion of a PCR amplification of a DNA fragment that was to be inserted into the TOPO TA pCR2.1 cloning vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix, and the entire mixture was loaded onto a 1% TBE (0.89 M Tris, 0.89 M Boric acid, 0.02 M EDTA sodium salt) agarose gel containing 0.5 ug/mL ethidium bromide.

Agarose gel electrophoresis was performed at 120 V, 400 mA for 30 minutes, and DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 ug of purified PCR product and High Concentration T4 DNA Ligase (New England Biolabs, Ipswich, Mass.) as per manufacturer's suggested protocol. For plasmid propagation, ligated constructs were transformed into Escherichia coli DH5α chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and 50 ug/mL of an appropriate antibiotic. Isolated transformants were grown for 16 hours in liquid LB medium containing 50 ug/mL carbenicillin or kanamycin antibiotic at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, Calif.).

Figure 5A:
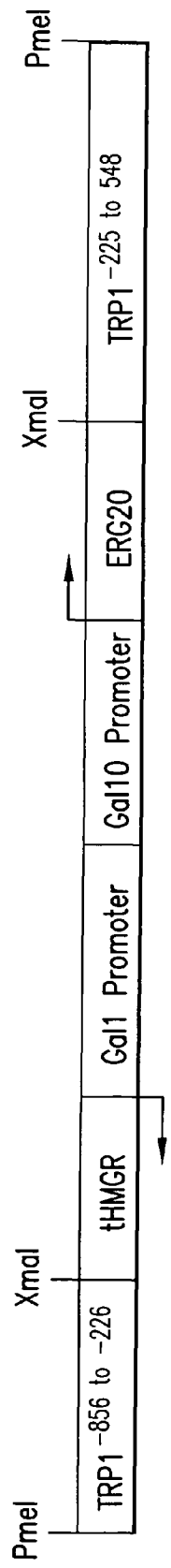
FIGS. 5A-E show maps of the inserts of vectors pAM489, pAM491, pAM493, pAM495, and pAM497.

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of ERG20 (ERG20 nucleotide positions 1 to 1208; A of ATG start codon is nucleotide 1) (ERG20), the genomic locus containing the divergent GAL1 and GAL10 promoter (GAL1 nucleotide position −1 to −668) ($P_{GAL}$), and a truncated ORF of HMG1 (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of Saccharomyces cerevisiae that extends from nucleotide position −856 to position 548 and harbors a non-native internal XmaI restriction site between bases −226 and −225, into the TOPO TA pCR2.1 cloning vector (Invitrogen, Carlsbad, Calif.). DNA fragments ERG20-$P_{GAL}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489 (see FIG. 5A for a map and SEQ ID NO: 3 for the nucleotide sequence of the ERG20-$P_{GAL}$-tHMGR insert).

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 37) | 61-67-CPK002-G (SEQ ID NO: 38) | TRP1$^{-856\ to\ -226}$ |
|  |  | 61-67-CPK003-G (SEQ ID NO: 39) | 61-67-CPK004-G (SEQ ID NO: 40) | TRP1$^{-225\text{-}to\ +548}$ |
|  | 100 ng of EG123 genomic DNA | 61-67-CPK025-G (SEQ ID NO: 61) | 61-67-CPK050-G (SEQ ID NO: 69) | ERG20 |
|  | 100 ng of Y002 genomic DNA | 61-67-CPK051-G (SEQ ID NO: 70) | 61-67-CPK052-G (SEQ ID NO: 71) | P$_{GAL}$ |
|  |  | 61-67-CPK053-G (SEQ ID NO: 72) | 61-67-CPK031-G (SEQ ID NO: 62) | tHMGR |
| 2 | 100 ng each of TRP1$^{-856\ to\ -226}$ and TRP1$^{-225\text{-}to\ +548}$ purified PCR products | 61-67-CPK001-G (SEQ ID NO: 37) | 61-67-CPK004-G (SEQ ID NO: 40) | TRP1$^{-856\ to\ +548}$ |
|  | 100 ng each of ERG20 and P$_{GAL}$ purified PCR products | 61-67-CPK025-G (SEQ ID NO: 61) | 61-67-CPK052-G (SEQ ID NO: 71) | ERG20-P$_{GAL}$ |
| 3 | 100 ng each of ERG20-P$_{GAL}$ and tHMGR purified PCR products | 61-67-CPK025-G (SEQ ID NO: 61) | 61-67-CPK031-G (SEQ ID NO: 62) | ERG20-P$_{GAL}$-tHMGR |

Figure 5B:
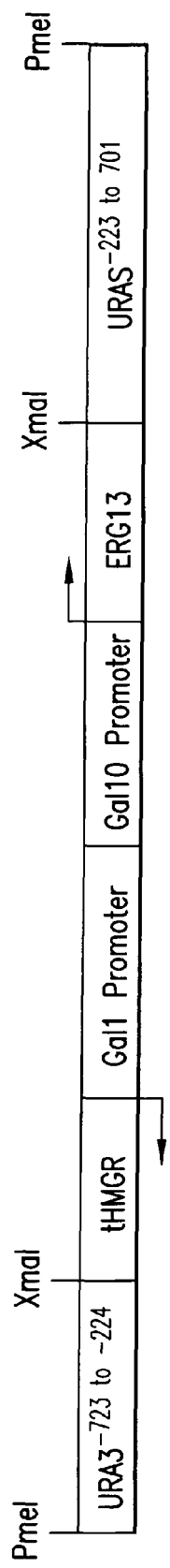

Plasmid pAM491 was generated by inserting the ERGβ-P$_{GAL}$-tHMGR insert of vector pAM472 into vector pAM467. Vector pAM472 was generated by inserting DNA fragment ERGβ-P$_{GAL}$-tHMGR, which comprises the ORF of ERG13 (ERG13 nucleotide positions 1 to 1626) (ERG13), the genomic locus containing the divergent GAL1 and GAL10 promoter (GAL1 nucleotide position −1 to −668) (P$_{GAL}$), and a truncated ORF of HMG1 (HMG1 nucleotide position 1586 to 3323) (tHMGR), into the XmaI restriction site of TOPO Zero Blunt II cloning vector. Vector pAM467 was generated by inserting DNA fragment URA3$^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments ERG13-P$_{GAL}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERGβ-P$_{GAL}$-tHMGR insert and the linearized pAM467 vector were gel purified, and 4 molar equivalents of the purified insert was ligated with 1 molar equivalent of the purified linearized vector, yielding pAM491 (see FIG. 5B for a map and SEQ ID NO: 4 for the nucleotide sequence of the ERGβ-P$_{GAL}$-tHMGR insert).

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 41) | 61-67-CPK006-G (SEQ ID NO: 42) | URA3$^{-723\ to\ -224}$ |
|  |  | 61-67-CPK007-G (SEQ ID NO: 43) | 61-67-CPK008-G (SEQ ID NO: 44) | URA3$^{-223\ to\ 701}$ |
|  | 100 ng of Y002 genomic DNA | 61-67-CPK032-G (SEQ ID NO: 63) | 61-67-CPK054-G (SEQ ID NO: 73) | ERG13 |
|  |  | 61-67-CPK052-G (SEQ ID NO: 71) | 61-67-CPK055-G (SEQ ID NO: 74) | P$_{GAL}$ |
|  |  | 61-67-CPK031-G (SEQ ID NO: 62) | 61-67-CPK053-G (SEQ ID NO: 72) | tHMGR |
| 2 | 100 ng each of URA3$^{-723\ to\ -224}$ and URA3$^{-223\ to\ 701}$ purified PCR products | 61-67-CPK005-G (SEQ ID NO: 41) | 61-67-CPK008-G (SEQ ID NO: 44) | URA3$^{-723\ to\ 701}$ |
|  | 100 ng each of ERG13 and P$_{GAL}$ purified PCR products | 61-67-CPK032-G (SEQ ID NO: 63) | 61-67-CPK052-G (SEQ ID NO: 71) | ERG13-P$_{GAL}$ |
| 3 | 100 ng each of ERG13-P$_{GAL}$ and tHMGR purified PCR products | 61-67-CPK031-G (SEQ ID NO: 62) | 61-67-CPK032-G (SEQ ID NO: 63) | ERG13-P$_{GAL}$-tHMGR |

Figure 5C:
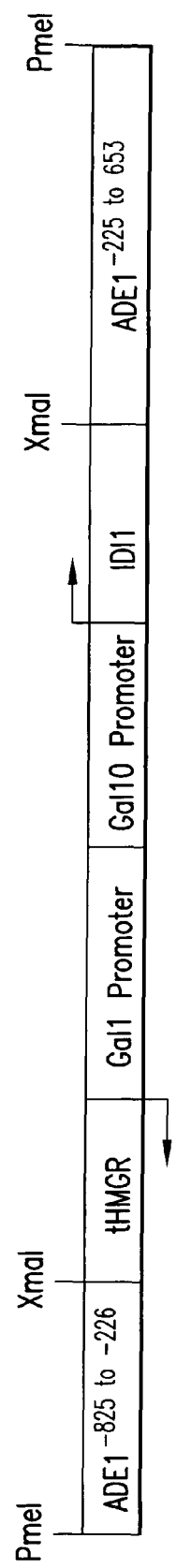

Plasmid pAM493 was generated by inserting the IDI1-$P_{GAL}$-tHMGR insert of vector pAM473 into vector pAM468. Vector pAM473 was generated by inserting DNA fragment IDI1-$P_{GAL}$-tHMGR, which comprises the ORF of IDI1 (IDI1 nucleotide position 1 to 1017) (IDI1), the genomic locus containing the divergent GAL1 and GAL10 promoter (GAL1 nucleotide position −1 to −668) ($P_{GAL}$), and a truncated ORF of HMG1 (HMG1 nucleotide positions 1586 to 3323) (tHMGR), into the TOPO Zero Blunt II cloning vector. Vector pAM468 was generated by inserting DNA fragment ADE1$^{-825\ to\ 653}$, which comprises a segment of the wild-type ADE1 locus of Saccharomyces cerevisiae that extends from nucle-otide position −225 to position 653 and harbors a non-native internal XmaI restriction site between bases −226 and −225, into the TOPO TA pCR2.1 cloning vector. DNA fragments IDI1-$P_{GAL}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-$P_{GAL}$-tHMGR insert and the linearized pAM468 vector were gel purified, and 4 molar equivalents of the purified insert was ligated with 1 molar equivalent of the purified linearized vector, yielding vector pAM493 (see FIG. 5C for a map and SEQ ID NO: 5 for the nucleotide sequence of the IDI1-$P_{GAL}$-tHMGR insert).

Figure 5D:
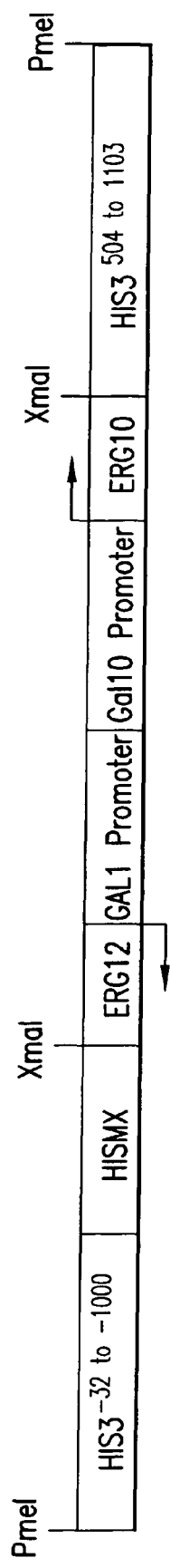

Plasmid pAM495 was generated by inserting the ERG10-$P_{GAL}$-ERG12 insert of pAM474 into vector pAM469. Vector pAM474 was generated by inserting DNA fragment ERG10-$P_{GAL}$-ERG12, which comprises the ORF of ERG10 (ERG10 nucleotide position 1 to 1347) (ERG10), the genomic locus containing the divergent GAL1 and GAL10 promoter (GAL1 nucleotide position −1 to −668) ($P_{GAL}$), and the ORF of ERG12 (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the wild-type HIS locus of Saccharomyces cerevisiae that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-$P_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the ERG10-$P_{GAL}$-ERG12 insert and the linearized pAM469 vector were gel purified, and 4 molar equivalents of the purified insert was ligated with 1 molar equivalent of the purified linearized vector, yielding vector pAM495 (see FIG. 5D for a map and SEQ ID NO: 6 for the nucleotide sequence of the ERG10-$P_{GAL}$-ERG12 insert).

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 45) | 61-67-CPK010-G (SEQ ID NO: 46) | ADE1$^{-825\ to\ -226}$ |
|   |   | 61-67-CPK011-G (SEQ ID NO: 47) | 61-67-CPK012-G (SEQ ID NO: 48) | ADE1$^{-225\ to\ 653}$ |
|   | 100 ng of Y002 genomic DNA | 61-67-CPK047-G (SEQ ID NO: 68) | 61-67-CPK064-G (SEQ ID NO: 83) | IDI1 |
|   |   | 61-67-CPK052-G (SEQ ID NO: 71) | 61-67-CPK065-G (SEQ ID NO: 84) | $P_{GAL}$ |
|   |   | 61-67-CPK031-G (SEQ ID NO: 62) | 61-67-CPK053-G (SEQ ID NO: 72) | tHMGR |
| 2 | 100 ng each of ADE1$^{-825\ to\ -226}$ and ADE1$^{-225\ to\ 653}$ purified PCR products | 61-67-CPK009-G (SEQ ID NO: 45) | 61-67-CPK012-G (SEQ ID NO: 48) | ADE1$^{-825\ to\ 653}$ |
|   | 100 ng each of IDI1 and $P_{GAL}$ purified PCR products | 61-67-CPK047-G (SEQ ID NO: 68) | 61-67-CPK052-G (SEQ ID NO: 71) | IDI1-$P_{GAL}$ |
| 3 | 100 ng each of IDI1-$P_{GAL}$ and tHMGR purified PCR products | 61-67-CPK031-G (SEQ ID NO: 62) | 61-67-CPK047-G (SEQ ID NO: 68) | IDI1-$P_{GAL}$-tHMGR |

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 49) | 61-67-CPK014alt-G (SEQ ID NO: 50) | $HIS3^{-32\ to\ -1000}$ |
| | | 61-67-CPK017-G (SEQ ID NO: 53) | 61-67-CPK018-G (SEQ ID NO: 54) | $HIS3^{504\ to\ -1103}$ |
| | | 61-67-CPK035-G (SEQ ID NO: 64) | 61-67-CPK056-G (SEQ ID NO: 75) | ERG10 |
| | | 61-67-CPK057-G (SEQ ID NO: 76) | 61-67-CPK058-G (SEQ ID NO: 77) | $P_{GAL}$ |
| | | 61-67-CPK040-G (SEQ ID NO: 65) | 61-67-CPK059-G (SEQ ID NO: 78) | ERG12 |
| | 10 ng of plasmid pAM330 DNA ** | 61-67-CPK015alt-G (SEQ ID NO: 51) | 61-67-CPK016-G (SEQ ID NO: 52) | HISMX |
| 2 | 100 ng each of $HIS3^{504\ to\ -1103}$ and HISMX PCR purified products | 61-67-CPK015alt-G (SEQ ID NO: 51) | 61-67-CPK018-G (SEQ ID NO: 54) | $HISMX-HIS3^{504\ to\ -1103}$ |
| | 100 ng each of ERG10 and $P_{GAL}$ purified PCR products | 61-67-CPK035-G (SEQ ID NO: 64) | 61-67-CPK058-G (SEQ ID NO: 77) | $ERG10-P_{GAL}$ |
| 3 | 100 ng each of $HIS3^{-32\ to\ -1000}$ and $HISMX-HIS3^{504\ to\ -1103}$ purified PCR products | 61-67-CPK013-G (SEQ ID NO: 49) | 61-67-CPK018-G (SEQ ID NO: 54) | $HIS3^{-32\ to\ -1000}-HISMX-HIS3^{504\ to\ -1103}$ |
| | 100 ng each of $ERG10-P_{GAL}$ and ERG12 purified PCR products | 61-67-CPK035-G (SEQ ID NO: 64) | 61-67-CPK040-G (SEQ ID NO: 65) | $ERG10-P_{GAL}-ERG12$ |

** The HISMX marker in pAM330 originated from pFA6a-HISMX6-PGAL1 as described by van Dijken et al. ((2000) Enzyme Microb. Technol. 26(9-10): 706-714).

Figure 5E:
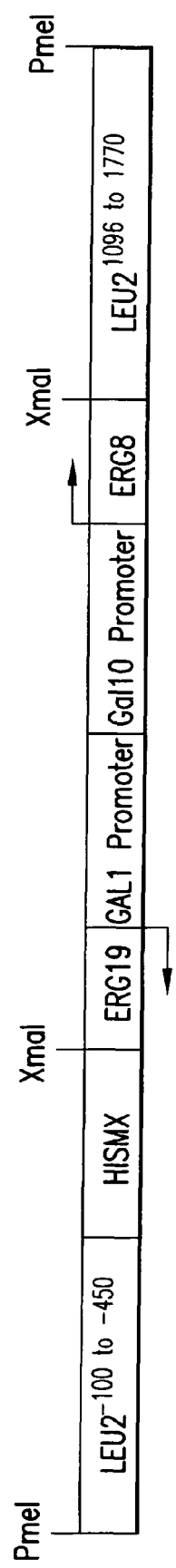

Plasmid pAM497 was generated by inserting the ERG8-$P_{GAL}$-ERG19 insert of pAM475 into vector pAM470. Vector pAM475 was generated by inserting DNA fragment ERG8-$P_{GAL}$-ERG19, which comprises the ORF of ERG8 (ERG8 nucleotide position 1 to 1512) (ERG8), the genomic locus containing the divergent GAL1 and GAL10 promoter (GAL1 nucleotide position −1 to −668) ($P_{GAL}$), and the ORF of ERG19 (ERG19 nucleotide position 1 to 1341) (ERG19), into the TOPO Zero Blunt II cloning vector. Vector pAM470 was generated by inserting DNA fragment $LEU2^{-100\ to\ 450}$-HISMX-$LEU2^{1096\ to\ 1770}$, which comprises two segments of the wild-type LEU2 locus of Saccharomyces cerevisiae that extend from nucleotide position −100 to position 450 and from nucleotide position 1096 to position 1770, a HISMX marker, and a non-native XmaI restriction site between the $LEU2^{1096\ to\ 1770}$ sequence and the HISMX marker, into the TOPO TA pCR2.1 cloning vector. DNA fragments ERG8-$P_{GAL}$-ERG19 and $LEU2^{-100\ to\ 450}$-HISMX-$LEU2^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497 (see FIG. 5E for a map and SEQ ID NO: 7 for the nucleotide sequence of the ERG8-$P_{GAL}$-ERG19 insert).

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 55) | 61-67-CPK020-G (SEQ ID NO: 56) | $LEU2^{-100\ to\ 450}$ |
| | | 61-67-CPK023-G (SEQ ID NO: 59) | 61-67-CPK024-G (SEQ ID NO: 60) | $LEU2^{1096\ to\ 1770}$ |
| | 10 ng of plasmid pAM330 DNA ** | 61-67-CPK021-G (SEQ ID NO: 57) | 61-67-CPK022-G (SEQ ID NO: 58) | HISMX |
| | 100 ng of Y002 genomic DNA | 61-67-CPK041-G (SEQ ID NO: 66) | 61-67-CPK060-G (SEQ ID NO: 79) | ERG8 |
| | | 61-67-CPK061-G (SEQ ID NO: 80) | 61-67-CPK062-G (SEQ ID NO: 81) | $P_{GAL}$ |
| | | 61-67-CPK046-G (SEQ ID NO: 67) | 61-67-CPK063-G (SEQ ID NO: 82) | ERG19 |
| 2 | 100 ng each of $LEU2^{1096\ to\ 1770}$ and HISMX purified PCR products | 61-67-CPK021-G (SEQ ID NO: 57) | 61-67-CPK024-G (SEQ ID NO: 60) | $HISMX-LEU2^{1096\ to\ 1770}$ |
| | 100 ng each of ERG8 and $P_{GAL}$ purified PCR products | 61-67-CPK041-G (SEQ ID NO: 66) | 61-67-CPK062-G (SEQ ID NO: 81) | $ERG8-P_{GAL}$ |
| 3 | 100 ng of $LEU2^{-100\ to\ 450}$ and $HISMX-LEU2^{1096\ to\ 1770}$ purified PCR products | 61-67-CPK019-G (SEQ ID NO: 55) | 61-67-CPK024-G (SEQ ID NO: 60) | $LEU2^{-100\ to\ 450}$-$HISMX-LEU2^{1096\ to\ 1770}$ |

TABLE 5-continued

PCR reactions performed to generate pAM497

| PCR Round | Template | Primer 1 | Primer 2 | PCR Product |
|---|---|---|---|---|
| | 100 ng each of ERG8-P$_{GAL}$ and ERG19 purified PCR products | 61-67-CPK041-G (SEQ ID NO: 66) | 61-67-CPK046-G (SEQ ID NO: 67) | ERG8-P$_{GAL}$-ERG19 |

** The HISMX marker in pAM330 originated from pFA6a-HISMX6-PGAL1 as described by van Dijken et al. ((2000) Enzyme Microb. Technol. 26(9-10): 706-714).

Example 5

This example describes methods for making expression plasmids that encode enzymes that convert GPP.

Figure 6:
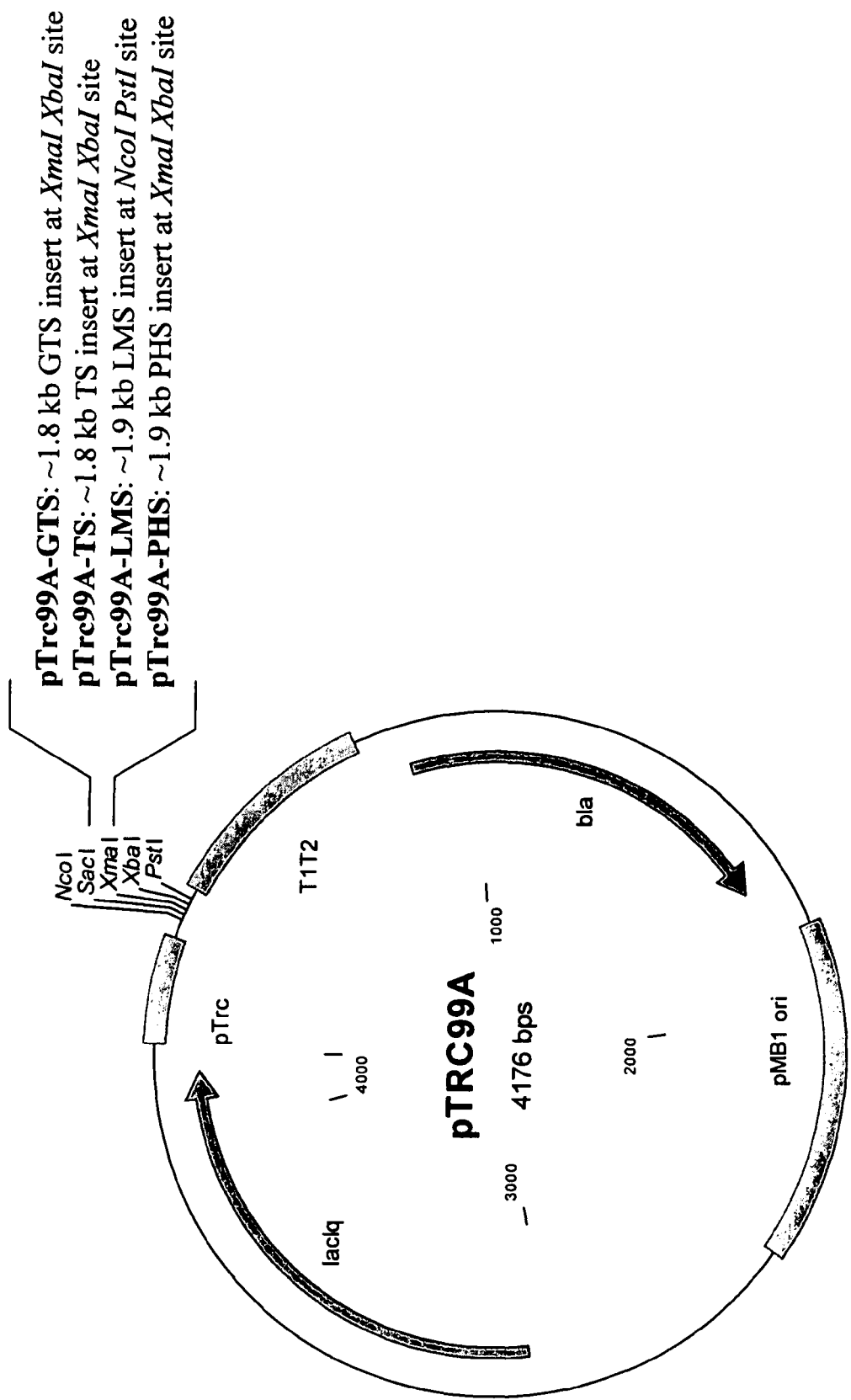
FIG. 6 shows maps of expression plasmids pTrc99A-GTS, pTrc99A-TS, pTrc99A-LMS, and pTrc99A-PHS.

Expression plasmids pTrc99A-GTS and pTrc99A-TS were generated by inserting a nucleotide sequence encoding a γ-terpinene synthase ("GTS") or a terpinolene synthase ("TS"), respectively, into the pTrc99A vector. The nucleotide sequence insert was generated synthetically, using as a template the coding sequence of the γ-terpinene synthase gene of *Citrus limon* (GenBank accession number AF514286 REGION: 30 . . . 1832) or the coding sequence of the terpinolene synthase gene of *Ocimum basilicum* (GenBank accession number AY693650) or of *Pseudotsuga menziesii* (GenBank accession number AY906866 REGION: 10 . . . 1887), all nucleotide sequences being codon-optimized for expression in *Escherichia coli* (SEQ ID NOs:8 through 10, respectively). The coding sequence was flanked by a leader XmaI restriction site and a terminal XbaI restriction site. The synthetic nucleic acid was cloned into compatible restriction enzyme sites of a cloning vector such as a standard pUC or pACYC origin vector, from which it was liberated again by digesting the DNA synthesis construct to completion using XbaI and XmaI restriction enzymes, resolving the reaction mixture by gel electrophoresis, and gel extracting the approximately 1.7 to 1.8 terpene synthase encoding DNA fragment. The isolated DNA fragment was ligated into the XmaI XbaI restriction site of vector pTrc99A (Amman et al., *Gene* 40:183-190 (1985)), yielding expression plasmid pTrc99A-GTS or pTrc99A-TS (see FIG. 6 for plasmid maps).

Expression plasmids pTrc99A-LMS and pTrc99A-PHS are generated by inserting a nucleotide sequence encoding a limonene synthase ("LMS") or a β-phellandrene synthase ("PHS"), respectively, into the pTrc99A vector. The nucleotide sequence insert is generated synthetically, using as a template for example the coding sequence of the limonene synthase gene of *Abies grandis* (GenBank accession number AF006193 REGION: 73 . . . 1986) or the coding sequence of the β-phellandrene synthase gene of *Abies grandis* (GenBank accession number AF139205 REGION: 34 . . . 1926). The nucleotide sequence encoding the limonene synthase is flanked by a leader NcoI restriction site and a terminal PstI restriction site, and the nucleotide sequence encoding the β-phellandrene synthase is flanked by a leader XmaI restriction site and a terminal XbaI restriction site. The limonene synthase DNA synthesis construct is digested to completion using NcoI and PstI restriction enzymes, and the β-phellandrene synthase DNA synthesis construct is digested to completion using XmaI and XbaI restriction enzymes. The reaction mixture is resolved by gel electrophoresis, the approximately 1.9 kb DNA fragments is gel extracted, and the isolated DNA fragment is ligated into the NcoI PstI restriction site (for the limonene synthase insert) or the XmaI XbaI restriction site (for the β-phellandrene synthase insert) of the pTrc99A vector, yielding expression plasmid pTrc99A-LMS or pTrc99A-PHS (see FIG. 6 for plasmid maps).

Figure 7:
FIG. 7 shows maps of expression plasmids pRS425-leu2d-GTS, pRS425-leu2d-TS, pRS425-leu2d-LMS, and pRS425-leu2d-PHS.

Expression plasmid pRS425-leu2d-GTS, pRS425-leu2d-TS, pRS425-leu2d-LMS, and pRS425-leu2d-PHS are generated by inserting a nucleotide sequence encoding a γ-terpinene synthase ("GTS"), a terpinolene synthase ("TS"), a limonene synthase ("LMS"), or a β-phellandrene synthase ("PHS"), respectively, linked to the divergent GAL1 and GAL10 promoter (GAL1 nucleotide position −1 to −668) (P$_{GAL}$), into vector pRS425-leu2d. Vector pRS425-leu2d was generated by PCR amplifying the leu2 gene of pAM178 (SEQ ID NO: 12) using primers PW-91-079-CPK373-G (SEQ ID NO: 89) and PW-79-079-CPK374-G (SEQ ID NO:90), and the backbone of vector pRS425 (GenBank accession number U03452) using primers PW-91-079-CPK376-G (SEQ ID NO: 91) and PW-79-079-CPK375-G (SEQ ID NO: 92), resolving the reaction mixtures by gel electrophoresis, gel extracting the approximately 1.6 kb leu2 gene fragment and the approximately 4.6 kb pRS425 vector backbone, treating the DNA fragments with T4 kinase to add terminal phosphate groups, and ligating the two DNA fragments. The nucleotide sequence insert is generated synthetically, using as a template for example the coding sequence of the γ-terpinene synthase gene of *Citrus limon* (GenBank accession number AF514286 REGION: 30 . . . 1832), the coding sequence of the terpinolene synthase gene of *Ocimum basilicum* (GenBank accession number AY693650) or of *Pseudotsuga menziesii* (GenBank accession number AY906866 REGION: 10 . . . 1887), the coding sequence of the limonene synthase gene of *Abies grandis* (GenBank accession number AF006193 REGION: 73 . . . 1986), or the coding sequence of the β-phellandrene synthase gene of *Abies grandis* (GenBank accession number AF139205 REGION: 34 . . . 1926), each coding sequence being linked to the divergent GAL1 and GAL10 promoter (GAL1 nucleotide position −1 to −668) (P$_{GAL}$). The nucleotide sequence has blunted termini, and can thus be cloned into compatible restriction sites of a cloning vector such as a standard pUC or pACYC origin vector. The synthetically generated P$_{GAL}$-terpene synthase sequence is isolated by digesting the DNA synthesis construct using SmaI restriction enzyme (partial digest for the β-phellandrene synthase construct, complete digests for all other constructs), the reaction mixture is resolved by gel electrophoresis, the approximately 2.5 kb to 2.6 kb DNA fragment is gel extracted, and the isolated DNA fragment is ligated into the SmaI restriction site of vector pRS425-leu2d, yielding expression plasmid pRS425-leu2d-GTS, pRS425-leu2d-TS, pRS425-leu2d-LMS, or pRS425-leu2d-PHS (see FIG. 7 for plasmid maps).

Example 6

This example describes the generation of *Escherichia coli* host strains useful in the invention.

As detailed in Table 6, host strains were or are created by transforming chemically competent *Escherichia coli* parent cells with one or more expression plasmids of Examples 1 through 3 and Example 5.

TABLE 6

*Escherichia coli* host strains

| Host Strain | E. coli Parent Strain | Expression Plasmids | Antibiotic Selection |
|---|---|---|---|
| 1 | DH1 | pMevT<br>pMBIS-gpps<br>pTrc99A-GTS | 100 ug/mL carbenicillin<br>34 ug/mL chloramphenicol<br>5 ug/mL tetracycline |
| 2 | | pMevT<br>pMBIS-gpps<br>pTrc99A-TS | |
| 3 | | pMevT<br>pMBIS-gpps<br>pTrc99A-LMS | |
| 4 | | pMevT<br>pMBIS-gpps<br>pTrc99A-PHS | |
| 5 | | pAM408<br>pAM424<br>pTrc99A-GTS | 100 μg/ml carbenicillin<br>50 μg/ml kanamycin<br>35 μg/ml chloramphenicol |
| 6 | | pAM408<br>pAM424<br>pTrc99A-TS | |
| 7 | | pAM408<br>pAM424<br>pTrc99A-LMS | |
| 8 | | pAM408<br>pAM424<br>pTrc99A-PHS | |

Host cell transformants are selected on Luria Bertoni (LB) agar containing antibiotics. Single colonies are transferred from LB agar to culture tubes containing 5 mL of LB liquid medium and antibiotics. The cultures are incubated at 37° C. on a rotary shaker at 250 rpm until growth reached late exponential phase. The cells are adapted to minimal media by passaging them through 4 to 5 successive rounds of M9-MOPS media containing 0.8% glucose and antibiotics (see Table 7 for the composition of the M9-MOPS medium). The cells are stored at −80° C. in cryo-vials in 1 mL stock aliquots made up of 400 uL sterile 50% glycerol and 600 uL liquid culture.

TABLE 7

Composition of M9-MOPS Culture Medium

| Component | Quantity (per L) |
|---|---|
| $Na_2HPO_4\ 7H_2O$ | 12.8 g |
| $KH_2PO_4$ | 3 g |
| NaCl | 0.5 g |
| $NH_4Cl$ | 1 g |
| $MgSO_4$ | 2 mmol |
| $CaCl_2$ | 0.1 mmol |
| Thiamine | 0.1 ug |
| MOPS buffer pH 7.4 | 100 mmol |
| $(NH_3)_6Mo7O_{24}\ 4H_2O$ | 3.7 ug |
| $H_3BO_4$ | 25 ug |
| $CoCl_2$ | 7.1 ug |
| $CuSO_4$ | 2.4 ug |
| $MnCl_2$ | 16 ug |
| $ZnSO_4$ | 2.9 ug |
| $FeSO_4$ | 0.28 mg |

Example 7

This example describes the generation of *Saccharomyces cerevisiae* strains useful in the invention.

*Saccharomyces cerevisiae* strains CEN.PK2-1C(Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (van Dijken et al. (2000) *Enzyme Microb. Technol.* 26(9-10):706-714) were prepared for introduction of inducible MEV pathway genes by replacing the ERG9 promoter with the *Saccharomyces cerevisiae* METS promoter, and the ADE1 ORF with the *Candida glabrata* LEU2 gene (CgLEU2). This was done by PCR amplifying the KanMX-PMET3 region of vector pAM328 (SEQ ID NO: 11) using primers 50-56-pw100-G (SEQ ID NO: 87) and 50-56-pw101-G (SEQ ID NO: 88), which include 45 base pairs of homology to the native ERG9 promoter, transforming 10 ug of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 ug Salmon Sperm DNA (Invitrogen Corp., Carlsbad, Calif.), and incubating the cells at 30° C. for 30 minutes followed by heat shocking them at 42° C. for 30 minutes (Schiestl and Gietz. (1989) *Curr. Genet.* 16, 339-346). Positive recombinants were identified by their ability to grow on rich medium containing 0.5 ug/ml Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, Va.) using primers 61-67-CPK066-G (SEQ ID NO: 85) and 61-67-CPK067-G (SEQ ID NO: 86), which contain 50 base pairs of flanking homology to the ADE1 ORF, and 10 ug of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was then generated by digesting 2 ug of pAM491 and pAM495 plasmid DNA to completion using PmeI restriction enzyme (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was next generated by digesting 2 ug of pAM489 and pAM497 plasmid DNA to completion using PmeI restriction enzyme, and introducing the purified DNA inserts into exponentially growing Y177 cells. Positive recombinants were selected for by growth on medium lacking tryptophan and histidine, and integration into the correct genomic locus was confirmed by diagnostic PCR.

Approximately $1\times10^7$ cells from strains Y188 and Y189 were mixed on a YPD medium plate for 6 hours at room temperature to allow for mating. The mixed cell culture was plated to medium lacking histidine, uracil, and tryptophan to select for growth of diploid cells. Strain Y238 was generated by transforming the diploid cells using 2 ug of pAM493 plasmid DNA that had been digested to completion using PmeI restriction enzyme, and introducing the purified DNA insert into the exponentially growing diploid cells. Positive recombinants were selected for by growth on medium lacking adenine, and integration into the correct genomic locus was confirmed by diagnostic PCR.

Haploid strain Y211 (MAT alpha) was generated by sporulating strain Y238 in 2% Potassium Acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Finally, host strains 9 through 12 are generated by transforming strain Y211 with expression plasmid pRS425-leu2d-GTS, pRS425-leu2d-TS, pRS425-leu2d-LMS, or pRS425-leu2d-PHS. Host cell transformants are selected on synthetic defined media, containing 2% glucose and all amino acids except leucine (SM-glu). Single colonies are transferred to culture vials containing 5 mL of liquid SM-glu lacking leucine, and the cultures are incubated by shaking at 30° C. until growth reaches stationary phase. The cells are stored at −80° C. in cryo-vials in 1 mL frozen aliquots made up of 400 uL 50% sterile glycerol and 600 uL liquid culture.

Example 8

This example describes the production of γ-terpinene, terpinolene, limonene, and β-phellandrene via the MEV pathway in *Escherichia coli* host strains.

Seed cultures of the host strains 1 through 4 are established by adding a stock aliquot of each strain to separate 125 mL flasks containing 25 mL M9-MOPS, 2% glucose, 0.5% yeast extract, and antibiotics as detailed in Table 6, and by growing the cultures overnight. The seed cultures are used to inoculate at an initial $OD_{600}$ of approximately 0.05 separate 250 mL flasks containing 40 mL M9-MOPS, 2% glucose, 0.5% yeast extract, and antibiotics. Cultures are incubated at 30° C. on a rotary shaker at 250 rpm until they reach an $OD_{600}$ of approximately 0.2, at which point the production of the compound of interest in the host cells is induced by adding 40 uL of 1 M IPTG to the culture medium. The compound of interest is separated from the culture medium through solvent-solvent extraction, or by settling and decantation if the titer of the compound of interest is large enough to saturate the media and to form a second phase.

Example 9

This example describes the production of γ-terpinene, terpinolene, limonene, and β-phellandrene via the DXP pathway in *Escherichia coli* host strains.

Seed cultures of the host strains 5 through 8 are established by adding a stock aliquot of each strain to separate 125 mL flasks containing 25 mL M9-MOPS, 0.8% glucose, 0.5% yeast extract, and antibiotics as detailed in Table 6, and by growing the cultures overnight. The seed cultures are used to inoculate at an initial $OD_{600}$ of approximately 0.05 separate 250 mL flasks containing 40 mL M9-MOPS, 45 ug/mL thiamine, micronutrients, 1.00E-5 mol/L FeSO4, 0.1 M MOPS, 2% glucose, 0.5% yeast extract, and antibiotics. Cultures are incubated at 30° C. in a humidified incubating shaker at 250 rpm until they reach an $OD_{600}$ of 0.2 to 0.3, at which point the production of the compound of interest in the host cells is induced by adding 40 uL of 1 M IPTG to the culture medium. The compound of interest is separated from the culture medium through solvent-solvent extraction, or by settling and decantation if the titer of the compound of interest is large enough to saturate the media and to form a second phase.

Example 10

This example describes the production of γ-terpinene, terpinolene, limonene, and β-phellandrene in *Saccharomyces cerevisiae* host strains.

Seed cultures of host strains 9 through 12 are established by adding stock aliquots to separate 125 mL flasks containing 25 mL SM-glu lacking leucine, and growing each culture overnight. The seed culture is used to inoculate at an initial $OD_{600}$ of approximately 0.05 a 250 mL baffled flask containing 40 mL of synthetic defined media containing 0.2% glucose and 1.8% galactose, and lacking leucine. The culture is incubated at 30° C. on a rotary shaker at 200 rpm. The compound of interest is separated from the culture medium through solvent-solvent extraction, or by settling and decantation if the titer of the compound of interest is large enough to saturate the media and to form a second phase.

Example 11

This example describes the hydrogenation of limonene to primarily limonane.

To a reaction vessel, limonene and 10% Pd/C catalyst [palladium, 10 wt. % on activated carbon, Aldrich #205699] are added at 6 g/L loading. The vessel is sealed and purged with nitrogen gas, then evacuated under vacuum. To begin the reaction, the vessel is stirred while adding compressed hydrogen gas at 80 psig. The mildly exothermic reaction proceeds at room temperature. Final conversion is 100%, marked by end of hydrogen consumption and verified by gas chromatography with flame ionization detection. The product-catalyst mixture is separated via gravity filtration through a 60 Å silica gel. The final product concentration is expected to be mostly limonane with less than 5% p-cymene.

Example 12

This example describes the hydrogenation of limonene to mostly limonane with some p-cymene.

To the reaction vessel, limonene and 10% Pd/C catalyst [palladium, 10 wt. % on activated carbon, Aldrich #205699] are added at 6 g/L loading. The vessel is sealed, purged with nitrogen gas, then evacuated under vacuum. The vessel is stirred while increasing the temperature to 105° C. An initial charge of compressed hydrogen gas is added at 80 psig and totaling approximately 0.05 mol hydrogen per mol limonene. Due to hydrogen consumption, pressure will drop to zero. After 12 hours reaction time, the temperature is decreased to 75° C. and continuously added compressed hydrogen at 80 psig. Final conversion is 100%, marked by end of hydrogen consumption and verified by gas chromatography with flame ionization detection. The product-catalyst mixture is separated via gravity filtration through a 60 Å silica gel. The final product concentration is expected to be between about 80% and about 90% limonane and between about 10% and about 20% p-cymene.

Example 13

This example describes the hydrogenation of limonene to limonane and p-cymene.

To the reaction vessel, limonene and 10% Pd/C catalyst [palladium, 10 wt. % on activated carbon, Aldrich #205699] are added at 6 g/L loading. The vessel is sealed, purged with nitrogen gas, then evacuated under vacuum. The vessel is stirred while increasing the temperature to 120° C. An initial charge of compressed hydrogen gas is added at 80 psig and totaling approximately 0.05 mol hydrogen per mol limonene. Due to hydrogen consumption, pressure will drop to zero. The initial charge of hydrogen allows for the formation of 4-isopropyl-1-methylcyclohex-1-ene which then is readily converted to p-cymene. After 12 hours reaction time, decrease the temperature to 75° C. and continuously add compressed hydrogen at 80 psig. Final conversion is 100%, marked by end of hydrogen consumption and verified by gas chromatography with flame ionization detection. The product-catalyst mixture is separated via gravity filtration through a 60 Å silica gel. Final product concentration is expected to be between about 70% and 80% limonane and between about 20% and about 30% p-cymene.

Example 14

A fuel composition (referred to as AMJ-300) comprising 97.1% limonane and 1.6% p-cymene is blended with various amounts of Jet A. The components of AMJ-300 were identified by gas chromatography/flame ionization detector (GC/FID). AMJ-300 includes 1.3% of unidentified compounds, of which 0.9% is believed to be 2,6-dimethyloctane.

The results of the various blends for their ability to meet ASTM D 1655 are shown in FIG. 8: Jet A, 100% AMJ-300, 50% AMJ-300 and 50% Jet A, and 20% AMJ-300 and 80% Jet A.

Example 15

A fuel composition (referred to as AMJ-310) comprising 81.0% limonane and 17.5% p-cymene is blended with various amounts of Jet A. The components of AMJ-310 were identified by gas chromatography/flame ionization detector (GC/FID). AMJ-310 includes 1.5% of unidentified compounds, of which 0.9% is believed to be 2,6-dimethyloctane.

Figure 9:
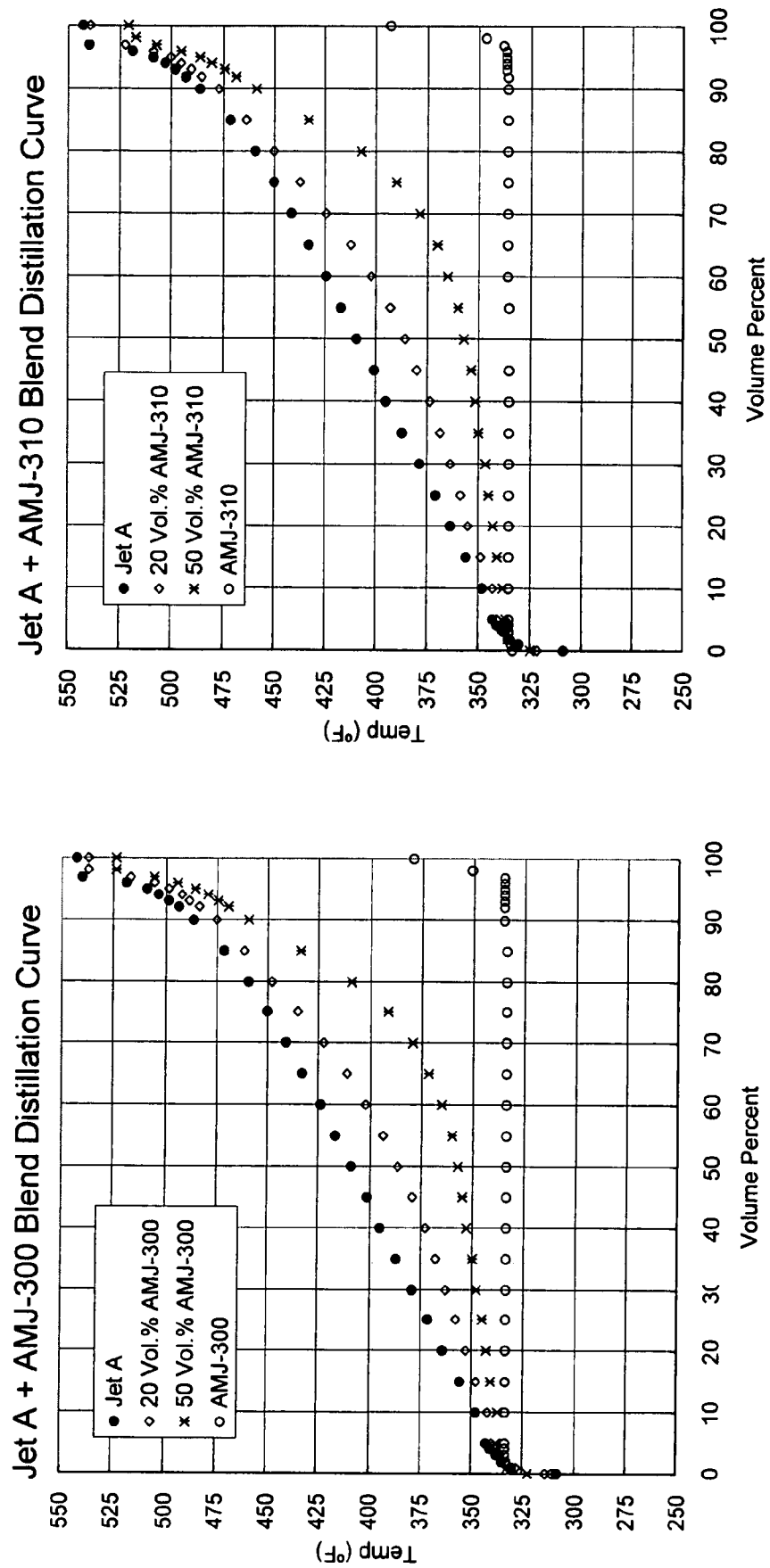
FIG. 9 shows the distillation curves for a Jet A and certain blends of Jet A, AMJ-300, and AMJ-310.

The results of the various blends for their ability to meet ASTM D 1655 are shown in FIG. 8: Jet A, 100% AMJ-310, 50% AMJ-310 and 50% Jet A, and 20% AMJ-310 and 80% Jet A. FIG. 9 shows the distillation curves for a Jet A and certain blends of Jet A, AMJ-300, and AMJ-310.

The fuel compositions described herein can be produced in a cost-effective and environmentally friendly manner. Advantageously, the isoprenoid compounds used in the fuel compositions herein can be produced by one or more microorganisms. These isoprenoid compounds can thus provide a renewable source of energy for diesel or jet fuels, in particularly the fuel compositions provided herein. Further, these isoprenoid compounds can decrease dependence on non-renewable sources of fuel, fuel components and/or fuel additives. In certain embodiments, the fuel composition provided herein comprises a bioengineered limonane.

While the invention has been described with respect to a limited number of embodiments, the specific features of one embodiment should not be attributed to other embodiments of the invention. No single embodiment is representative of all aspects of the claimed subject matter. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. It should be noted that the application of the jet fuel compositions disclosed herein is not limited to jet engines; they can be used in any equipment which requires a jet fuel. Although there are specifications for most jet fuels, not all jet fuel compositions disclosed herein need to meet all requirements in the specifications. It is noted that the methods for making and using the jet fuel compositions disclosed herein are described with reference to a number of steps. These steps can be practiced in any sequence. One or more steps may be omitted or combined but still achieve substantially the same results. The appended claims intend to cover all such variations and modifications as falling within the scope of the invention.

All publications and patent applications mentioned in this specification are herein incorporated by reference to the same extent as if each individual publication or patent application was specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A fuel composition comprising or obtainable from a mixture comprising:
   (a) limonane;
   (b) a petroleum-based fuel;
   (c) a fuel additive; and
   (d) p-cymene,
wherein the amount of the limonane compound is at least about 11 vol. %, the amount of the petroleum-based fuel is at least about 5 vol. %, and the amount of the p-cymene is from about 1 vol. % to about 25 vol. %, all amounts based on the total volume of the fuel composition, and wherein the fuel composition has a flash point equal to or greater than 38° C.

2. A jet fuel composition comprising:
   (a) limonane;
   (b) a petroleum-based fuel;
   (c) a jet fuel additive; and
   (d) p-cymene,
wherein the amount of the limonane compound is at least about 11 vol. %, the amount of the petroleum-based fuel is at least about 5 vol. %, and the amount of the p-cymene is from about 1 vol. % to about 25 vol. %, all amounts based on the total volume of the jet fuel composition, and wherein the fuel composition has a density from about 750 kg/m³ to about 850 kg/m³ at 15° C., a flash point equal to or greater than 38° C.

3. The fuel compositions of claim 1 or 2, wherein the limonane is

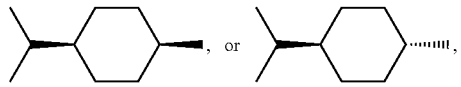

or a combination thereof.

4. The fuel compositions of claim 1 or 2, wherein the amount of the limonane is from about 11 vol. % to about 15 vol. %, based on the total volume of the fuel composition.

5. The fuel compositions of claim 1 or 2, wherein the amount of the limonane is from about 15 vol. % to about 80 vol. %, based on the total volume of the fuel composition.

6. The fuel compositions of claim 1 or 2, wherein the amount of the limonane is from about 20 vol. % to about 75 vol. %, based on the total volume of the fuel composition.

7. The fuel compositions of claim 1 or 2, wherein the amount of the limonane is from about 25 vol. % to about 75 vol. %, based on the total volume of the fuel composition.

8. The fuel composition of claim 1, wherein the amount of the p-cymene is at most about 25 vol. %, based on the total volume of the fuel composition.

9. The fuel composition of claim 1, wherein the petroleum-based fuel is kerosene.

10. The fuel composition of claim 1, wherein the fuel composition has a density from about 750 kg/m³ to about 850 kg/m³ at 15° C.

11. The fuel composition of claim 1 or 2, wherein the petroleum-based fuel is Jet A, Jet A-1 or Jet B.

12. The fuel composition of claim 11, wherein the fuel composition meets the ASTM D 1655 specification for Jet A.

13. The fuel composition of claim 11, wherein the fuel composition meets the ASTM D 1655 specification for Jet A-1.

14. The fuel composition of claim 11, wherein the fuel composition meets the ASTM D 1655 specification for Jet B.

15. The jet fuel composition of claim 2, wherein the fuel additive is at least one additive selected from the group consisting of an oxygenate, an antioxidant, a thermal stability improver, a stabilizer, a cold flow improver, a combustion improver, an anti-foam, an anti-haze additive, a corrosion inhibitor, a lubricity improver, an icing inhibitor, an injector cleanliness additive, a smoke suppressant, a drag reducing additive, a metal deactivator, a dispersant, a detergent, a de-emulsifier, a dye, a marker, a static dissipater, a biocide, and combinations thereof.

16. A method of making a fuel composition comprising:
   (a) contacting an isoprenoid starting material with hydrogen in the presence of a catalyst to form a limonane and p-cymene; and
   (b) mixing the limonane and p-cymene with a petroleum-based fuel to make the fuel composition;
wherein the amount of the limonane compound is at least about 11 vol. %, the amount of the petroleum-based fuel is at least about 5 vol. %, and the amount of the p-cymene is from about 1 vol. % to about 25 vol. %, all amounts based on the total volume of the fuel composition, and wherein the fuel composition has a flash point equal to or greater than 38° C.

17. The method of claim 16, wherein the isoprenoid starting material is limonene, β-phellandrene, γ-terpinene, terpinolene, or a combination thereof.

18. A method of making a fuel composition from a simple sugar comprising:
(a) contacting a cell capable of making an isoprenoid starting material with the simple sugar under conditions suitable for making the isoprenoid starting material;
(b) converting the isoprenoid starting material to limonane; and
(c) mixing the limonane with a petroleum-based fuel to make the fuel composition, wherein the amount of the limonane compound is at least about 11 vol. % and the amount of the petroleum-based fuel is at least about 5 vol. %, both amounts based on the total volume of the fuel composition, and wherein the fuel composition has a flash point equal to or greater than 38° C.

19. The method of claim 18, wherein the isoprenoid starting material is limonene, β-phellandrene, γ-terpinene, terpinolene, or a combination thereof.

20. A fuel composition made by the method of either of any of claims 16-19.

21. A vehicle comprising an internal combustion engine, a fuel tank connected to the internal combustion engine, and a fuel composition in the fuel tank, wherein the fuel composition is the fuel composition of claim 1 or 2, wherein the amount of the limonane compound is at least about 11 vol. %, the amount of the petroleum-based fuel is at least about 5 vol. %, and the amount of the p-cymene is from about 1 vol. % to about 25 vol. %, all amounts based on the total volume of the fuel composition, and wherein the fuel composition has a flash point equal to or greater than 38° C., and wherein the fuel composition is used to power the internal combustion engine.

22. A method of powering an engine comprising the step of combusting the fuel composition of claim 1 or 2 in the engine.

23. The method of claim 22, wherein the engine is a jet engine.

24. The fuel composition of claim 1, wherein the total amount of aromatic compounds in the fuel composition is from about 15% to about 35% by weight or volume, based on the total weight or volume of the fuel composition.

25. The fuel composition of claim 2, wherein the total amount of aromatic compounds in the fuel composition is from about 15% to about 35% by weight or volume, based on the total weight or volume of the fuel composition.

26. The method of claim 16, wherein the total amount of aromatic compounds in the fuel composition is from about 15% to about 35% by weight or volume, based on the total weight or volume of the fuel composition.

* * * * *

Disclaimer 7,935,156—Neil Stephen Renninger, Oakland, CA; Jason A. Ryder, Oakland, CA; Karl J. Fisher. JET FUEL COMPOSITIONS AND METHODS OF MAKING AND USING SAME. Patent dated May. 03, 2011. Disclaimer filed Jan. 31, 2011, by the assignee, Amyris Biotechnologies, Inc.

The term of this patent shall not extend beyond the expiration date of Pat. No. 7589243.

(*Official Gazette* May 24, 2011)